United States Patent
Gao et al.

(10) Patent No.: US 10,919,977 B2
(45) Date of Patent: Feb. 16, 2021

(54) BISPECIFIC TETRAVALENT ANTIBODIES AND METHODS OF MAKING AND USING THEREOF

(71) Applicant: SystImmune, Inc., Bellevue, WA (US)

(72) Inventors: Zeren Gao, Bellevue, WA (US); Phil Tan, Bellevue, WA (US); Brian R. Kovacevich, Bellevue, WA (US); Blair R. Renshaw, Bellevue, WA (US); Jeffrey B. Adamo, Bellevue, WA (US); Nga Sze Amanda Mak, Bellevue, WA (US); Shi Zhuo, Chengdu (CN); Lan Chen, Chengdu (CN); Yi Zhu, Chengdu (CN)

(73) Assignees: SYSTIMMUNE, INC., Bellevue, WA (US); Sichuan Baili Pharmaceutical Co. Ltd., Chengdu (CN)

( * ) Notice: Subject to any disclaimer, the term of this patent is extended or adjusted under 35 U.S.C. 154(b) by 0 days.

(21) Appl. No.: 15/119,694

(22) PCT Filed: Dec. 19, 2015

(86) PCT No.: PCT/US2015/066951
§ 371 (c)(1),
(2) Date: Aug. 17, 2016

(87) PCT Pub. No.: WO2016/106157
PCT Pub. Date: Jun. 30, 2016

(65) Prior Publication Data
US 2017/0073418 A1    Mar. 16, 2017

Related U.S. Application Data

(60) Provisional application No. 62/095,348, filed on Dec. 22, 2014.

(51) Int. Cl.
| | | |
|---|---|---|
| *C07K 16/30* | (2006.01) | |
| *C07K 16/32* | (2006.01) | |
| *A61K 47/68* | (2017.01) | |
| *C07K 16/28* | (2006.01) | |
| *A61K 39/395* | (2006.01) | |
| *A61K 45/06* | (2006.01) | |
| *C07K 16/46* | (2006.01) | |
| *A61K 39/00* | (2006.01) | |

(52) U.S. Cl.
CPC ...... *C07K 16/3015* (2013.01); *A61K 39/3955* (2013.01); *A61K 39/39558* (2013.01); *A61K 45/06* (2013.01); *A61K 47/6803* (2017.08); *A61K 47/6849* (2017.08); *A61K 47/6851* (2017.08); *C07K 16/2863* (2013.01); *C07K 16/32* (2013.01); *C07K 16/468* (2013.01); *A61K 2039/505* (2013.01); *A61K 2039/5152* (2013.01); *C07K 2317/21* (2013.01); *C07K 2317/24* (2013.01); *C07K 2317/31* (2013.01); *C07K 2317/35* (2013.01); *C07K 2317/622* (2013.01); *C07K 2317/64* (2013.01); *C07K 2317/73* (2013.01); *C07K 2317/732* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 2010/0256338 A1* | 10/2010 | Brinkmann | C07K 16/00 530/387.3 |
| 2012/0134993 A1 | 5/2012 | Pan et al. | |
| 2012/0270801 A1* | 10/2012 | Frejd | C07K 14/31 514/19.4 |
| 2014/0056895 A1 | 2/2014 | Baurin et al. | |
| 2014/0135482 A1 | 5/2014 | Bossenmaier et al. | |

FOREIGN PATENT DOCUMENTS

| | | | | |
|---|---|---|---|---|
| WO | WO 2007/147001 | * | 12/2007 | ........... A61K 39/395 |
| WO | WO2014144357 A1 | | 9/2014 | |

OTHER PUBLICATIONS

Dong et al. (mAbs, 3(3): 273-288, 2011).*
Hoet et al. (Nature Biotechnology, 23(3): 344-349, 2005).*
Chen et al. (Advanced Drug Delivery Reviews, 65: 1357-1369, Oct. 2013).*
Mariuzza (Annu. Rev. Biophys. Biophys. Chem., 16: 139-159, 1987).*

* cited by examiner

*Primary Examiner* — Nelson B Moseley, II
(74) *Attorney, Agent, or Firm* — Zhihua Han; Wen IP LLC

(57) ABSTRACT

A bispecific tetravalent antibody comprising an IgG having a pair of heavy chains and a pair of light chains, and two scFv components being connected to either C or N terminals of the heavy or light chains. The bispecific tetravalent antibody may have a binding specificity for two different members of EGFR family.

29 Claims, 35 Drawing Sheets
Specification includes a Sequence Listing.

SEQUENCE LISTING

<160> NUMBER OF SEQ ID NOS: 138

<210> SEQ ID NO 1
<211> LENGTH: 654
<212> TYPE: DNA
<213> ORGANISM: artificial sequence
<220> FEATURE:
<223> OTHER INFORMATION: Synthesized

<400> SEQUENCE: 1

```
cagtctgccc tgactcagcc tgcctccgtg tctgggtctc ctggacagtc gatcaccatc      60
tcctgcactg gaaccagcag tgacgttggt ggttataact ttgtctcctg gtaccaacaa     120
cacccaggca aagcccccaa actcatgatc tatgatgtca gtgatcggcc ctcaggggtg     180
tctgatcgct tctccggctc caagtctggc aacacggcct ccctgatcat ctctggcctc     240
caggctgacg acgaggctga ttattactgc agctcatatg ggagcagcag cactcatgtg     300
attttcggcg gagggaccaa gctgaccgtc ctacgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600
acccatcagg gcctgagctc gcccgtcaca aagagcttca caggggaga gtgt            654
```

<210> SEQ ID NO 2
<211> LENGTH: 333
<212> TYPE: DNA
<213> ORGANISM: artificial sequence
<220> FEATURE:
<223> OTHER INFORMATION: Synthesized

<400> SEQUENCE: 2

```
cagtctgccc tgactcagcc tgcctccgtg tctgggtctc ctggacagtc gatcaccatc      60
tcctgcactg gaaccagcag tgacgttggt ggttataact ttgtctcctg gtaccaacaa     120
cacccaggca aagcccccaa actcatgatc tatgatgtca gtgatcggcc ctcaggggtg     180
tctgatcgct tctccggctc caagtctggc aacacggcct ccctgatcat ctctggcctc     240
caggctgacg acgaggctga ttattactgc agctcatatg ggagcagcag cactcatgtg     300
attttcggcg gagggaccaa gctgaccgtc cta                                  333
```

<210> SEQ ID NO 3
<211> LENGTH: 218
<212> TYPE: PRT
<213> ORGANISM: artificial sequence
<220> FEATURE:
<223> OTHER INFORMATION: Synthesized

<400> SEQUENCE: 3

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
```

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 4
<211> LENGTH: 110
<212> TYPE: PRT
<213> ORGANISM: artificial sequence
<220> FEATURE:
<223> OTHER INFORMATION: Synthesized

<400> SEQUENCE: 4

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val
            100                 105                 110

<210> SEQ ID NO 5
<211> LENGTH: 1344
<212> TYPE: DNA
<213> ORGANISM: artificial sequence
<220> FEATURE:
<223> OTHER INFORMATION: Synthesized

<400> SEQUENCE: 5
caggtgcagc tgcaggagtc ggggggaggc ctggtcaagc ctggagggtc cctgagactc      60
tcctgtgcag cctctggatt caccttagt agttattgga tgagctgggt ccgccaggct     120
ccagggaagg ggctggagtg ggtggccaac ataaaccgcg atggaagtgc gagttactat    180
gtggactctg tgaagggccg attcaccatc tccagagacg acgccaagaa ctcactgtat    240
ctgcaaatga acagcctgag agctgaggac acggctgtgt attactgtgc gagagatcgt    300

```
ggggtgggct acttcgatct ctggggccgt ggcaccctgg tcaccgtctc gagcgctagc      360
accaagggcc catcggtctt ccccctggca cctcctcca agagcacctc tgggggcaca       420
gcggccctgg gctgcctggt caaggactac ttccccgaac cggtgacggt gtcgtggaac      480
tcaggcgccc tgaccagcgg cgtgcacacc ttccggctg tcctacagtc ctcaggactc       540
tactccctca gcagcgtggt gaccgtgccc tccagcagct gggcaccca gacctacatc       600 tgcaacgtga atcacaagcc cagcaacacc aaggtggaca gagagttga gcccaaatct       660 tgtgacaaaa ctcacacatg cccaccgtgc ccagcacctg aactcctggg ggaccgtca       720 gtcttcctct ccccccaaa acccaaggac accctcatga tctcccggac ccctgaggtc       780
acatgcgtgg tggtggacgt gagccacgaa gaccctgagg tcaagttcaa ctggtacgtg      840
gacggcgtgg aggtgcataa tgccaagaca agccgcggg aggagcagta caacagcacg       900
taccgtgtgg tcagcgtcct caccgtcctg caccaggact ggctgaatgg caaggagtac      960
aagtgcaagg tctccaacaa agccctccca gcccccatcg agaaaaccat ctccaaagcc     1020
aaagggcagc cccgagaacc acaggtgtac accctgcccc catcccggga ggagatgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctatagcaag ctcaccgtgg acaagagcag gtggcagcag     1260
gggaacgtct tctcatgctc cgtgatgcat gaggctctgc acaaccacta cacgcagaag     1320
agcctctccc tgtctccggg taaa                                            1344

<210> SEQ ID NO 6
<211> LENGTH: 354
<212> TYPE: DNA
<213> ORGANISM: artificial sequence
<220> FEATURE:
<223> OTHER INFORMATION: Synthesized

<400> SEQUENCE: 6
caggtgcagc tgcaggagtc gggggggaggc ctggtcaagc ctggagggtc cctgagactc       60
tcctgtgcag cctctggatt caccttagt agttattgga tgagctgggt ccgccaggct       120
ccagggaagg ggctgagtg ggtggccaac ataaaccgcg atggaagtgc gagttactat       180
gtggactctg tgaagggccg attcaccatc tccagagacg acgccaagaa ctcactgtat       240
ctgcaaatga acagcctgag agctgaggac acggctgtgt attactgtgc gagagatcgt       300
ggggtgggct acttcgatct ctggggccgt ggcaccctgg tcaccgtctc gagc             354

<210> SEQ ID NO 7
<211> LENGTH: 448
<212> TYPE: PRT
<213> ORGANISM: artificial sequence
<220> FEATURE:
<223> OTHER INFORMATION: Synthesized

<400> SEQUENCE: 7

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
```

```
            50                  55                  60
Lys Gly Arg Phe Thr Ile Ser Arg Asp Asp Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Val Gly Tyr Phe Asp Leu Trp Gly Arg Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 8
<211> LENGTH: 118
<212> TYPE: PRT
<213> ORGANISM: artificial sequence
```

```
<220> FEATURE:
<223> OTHER INFORMATION: Synthesized

<400> SEQUENCE: 8

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser
        115

<210> SEQ ID NO 9
<211> LENGTH: 642
<212> TYPE: PRT
<213> ORGANISM: artificial sequence
<220> FEATURE:
<223> OTHER INFORMATION: Synthesized

<400> SEQUENCE: 9

Gly Ala Cys Ala Thr Cys Cys Ala Gly Ala Thr Gly Ala Cys Cys Cys
1               5                   10                  15

Ala Gly Thr Cys Thr Cys Cys Ala Thr Cys Cys Thr Cys Cys Cys Thr
            20                  25                  30

Gly Thr Cys Thr Gly Cys Ala Thr Cys Thr Gly Thr Ala Gly Gly Ala
        35                  40                  45

Gly Ala Cys Ala Gly Ala Gly Thr Cys Ala Cys Cys Ala Thr Cys Ala
    50                  55                  60

Cys Thr Thr Gly Cys Cys Ala Gly Gly Cys Gly Ala Gly Thr Cys Ala
65                  70                  75                  80

Gly Gly Ala Cys Ala Thr Cys Ala Gly Cys Ala Ala Cys Thr Ala Thr
                85                  90                  95

Thr Thr Ala Ala Ala Thr Thr Gly Gly Thr Ala Thr Cys Ala Gly Cys
            100                 105                 110

Ala Gly Ala Ala Ala Cys Cys Ala Gly Gly Gly Ala Ala Ala Gly Cys
            115                 120                 125

Cys Cys Cys Thr Ala Ala Ala Cys Thr Cys Cys Thr Gly Ala Thr Cys
        130                 135                 140

Thr Ala Cys Gly Ala Thr Gly Cys Ala Thr Cys Cys Ala Ala Thr Thr
145                 150                 155                 160

Thr Gly Gly Ala Ala Ala Cys Ala Gly Gly Gly Gly Thr Cys Cys Cys
            165                 170                 175

Ala Thr Cys Ala Ala Gly Gly Thr Thr Cys Ala Gly Thr Gly Gly Ala
            180                 185                 190

Ala Gly Thr Gly Gly Ala Thr Cys Thr Gly Gly Gly Ala Cys Ala Gly
            195                 200                 205

Ala Thr Thr Thr Thr Ala Cys Thr Thr Thr Cys Ala Cys Cys Ala Thr
```

```
    210                 215                 220

Cys Ala Gly Cys Ala Gly Cys Cys Thr Gly Cys Ala Gly Cys Cys Thr
225                 230                 235                 240

Gly Ala Ala Gly Ala Thr Ala Thr Thr Gly Cys Ala Ala Cys Ala Thr
                245                 250                 255

Ala Thr Thr Thr Cys Thr Gly Thr Cys Ala Ala Cys Ala Cys Thr Thr
            260                 265                 270

Thr Gly Ala Thr Cys Ala Thr Cys Thr Cys Cys Cys Gly Cys Thr Cys
        275                 280                 285

Gly Cys Thr Thr Thr Cys Gly Gly Cys Gly Gly Ala Gly Gly Gly Ala
    290                 295                 300

Cys Cys Ala Ala Gly Gly Thr Gly Gly Ala Ala Ala Thr Thr Ala Ala
305                 310                 315                 320

Ala Cys Gly Thr Ala Cys Gly Gly Thr Gly Gly Cys Thr Gly Cys Ala
                325                 330                 335

Cys Cys Ala Thr Cys Thr Gly Thr Cys Thr Thr Cys Ala Thr Cys Thr
            340                 345                 350

Thr Cys Cys Cys Gly Cys Cys Ala Thr Cys Thr Gly Ala Thr Gly Ala
        355                 360                 365

Gly Cys Ala Gly Thr Thr Gly Ala Ala Ala Thr Cys Thr Gly Gly Ala
    370                 375                 380

Ala Cys Thr Gly Cys Cys Thr Cys Thr Gly Thr Thr Gly Thr Gly Thr
385                 390                 395                 400

Gly Cys Cys Thr Gly Cys Thr Gly Ala Ala Thr Ala Ala Cys Thr Thr
                405                 410                 415

Cys Thr Ala Thr Cys Cys Cys Ala Gly Ala Gly Ala Gly Gly Cys Cys
            420                 425                 430

Ala Ala Ala Gly Thr Ala Cys Ala Gly Thr Gly Gly Ala Ala Gly Gly
        435                 440                 445

Thr Gly Gly Ala Thr Ala Ala Cys Gly Cys Cys Cys Thr Cys Cys Ala
    450                 455                 460

Ala Thr Cys Gly Gly Gly Thr Ala Ala Cys Thr Cys Cys Cys Ala Gly
465                 470                 475                 480

Gly Ala Gly Ala Gly Thr Gly Thr Cys Ala Cys Ala Gly Ala Gly Cys
                485                 490                 495

Ala Gly Gly Ala Cys Ala Gly Cys Ala Ala Gly Gly Ala Cys Ala Gly
            500                 505                 510

Cys Ala Cys Cys Thr Ala Cys Ala Gly Cys Cys Thr Cys Ala Gly Cys
        515                 520                 525

Ala Gly Cys Ala Cys Cys Cys Thr Gly Ala Cys Gly Cys Thr Gly Ala
    530                 535                 540

Gly Cys Ala Ala Ala Gly Cys Ala Gly Ala Cys Thr Ala Cys Gly Ala
545                 550                 555                 560

Gly Ala Ala Ala Cys Ala Cys Ala Ala Ala Gly Thr Cys Thr Ala Cys
                565                 570                 575

Gly Cys Cys Thr Gly Cys Gly Ala Ala Gly Thr Cys Ala Cys Cys Cys
            580                 585                 590

Ala Thr Cys Ala Gly Gly Gly Cys Cys Thr Gly Ala Gly Cys Thr Cys
        595                 600                 605

Gly Cys Cys Cys Gly Thr Cys Ala Cys Ala Ala Ala Gly Ala Gly Cys
    610                 615                 620

Thr Thr Cys Ala Ala Cys Ala Gly Gly Gly Gly Ala Gly Ala Gly Thr
625                 630                 635                 640

```
<210> SEQ ID NO 10
<211> LENGTH: 321
<212> TYPE: DNA
<213> ORGANISM: artificial sequence
<220> FEATURE:
<223> OTHER INFORMATION: Synthesized

<400> SEQUENCE: 10
gacatccaga tgacccagtc tccatcctcc ctgtctgcat ctgtaggaga cagagtcacc      60
atcacttgcc aggcgagtca ggacatcagc aactatttaa attggtatca gcagaaacca     120
gggaaagccc ctaaactcct gatctacgat gcatccaatt tggaaacagg ggtcccatca     180
aggttcagtg aagtggatc tgggacagat tttactttca ccatcagcag cctgcagcct     240
gaagatattg caacatattt ctgtcaacac tttgatcatc tcccgctcgc tttcggcgga     300
gggaccaagg tggaaattaa a                                               321

<210> SEQ ID NO 11
<211> LENGTH: 214
<212> TYPE: PRT
<213> ORGANISM: artificial sequence
<220> FEATURE:
<223> OTHER INFORMATION: Synthesized

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
```

```
<211> LENGTH: 107
<212> TYPE: PRT
<213> ORGANISM: artificial sequence
<220> FEATURE:
<223> OTHER INFORMATION: Synthesized

<400> SEQUENCE: 12
```

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

```
<210> SEQ ID NO 13
<211> LENGTH: 1347
<212> TYPE: DNA
<213> ORGANISM: artificial sequence
<220> FEATURE:
<223> OTHER INFORMATION: Synthesized
<400> SEQUENCE: 13
caggtgcagc tgcaggagtc gggcccagga ctggtgaagc cttcggagac cctgtccctc      60
acctgcactg tctctggtgg ctccgtcagc agtggtgatt actactggac ctggatccgg     120
cagtccccag ggaagggact ggagtggatt ggacacatct attacagtgg aacaccaat     180
tataaccct cccctcaagag ccgactcacc atatcaattg acacgtccaa gactcagttc     240
tccctgaagc tgagttctgt gaccgctgcg gacacggcca tttattactg tgtgcgagat     300
cgagtgactg gtgcttttga tatctggggc aagggacaa tggtcaccgt ctcgagcgct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc cccatcccg ggaggagatg     1080
accaagaacc aggtcagcct gacctgcctg gtcaaaggct tctatccag cgacatcgcc    1140
gtggagtggg agagcaatgg gcagccggag aacaactaca agaccacgcc tcccgtgctg    1200
```

```
gactccgacg gctccttctt cctctatagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 14
<211> LENGTH: 357
<212> TYPE: DNA
<213> ORGANISM: artificial sequence
<220> FEATURE:
<223> OTHER INFORMATION: Synthesized

<400> SEQUENCE: 14

```
caggtgcagc tgcaggagtc gggcccagga ctggtgaagc cttcggagac cctgtccctc      60
acctgcactg tctctggtgg ctccgtcagc agtggtgatt actactggac ctggatccgg     120
cagtccccag ggaagggact ggagtggatt ggacacatct attacagtgg gaacaccaat     180
tataacccct ccctcaagag ccgactcacc atatcaattg acacgtccaa gactcagttc     240
tccctgaagc tgagttctgt gaccgctgcg gacacggcca tttattactg tgtgcgagat     300
cgagtgactg gtgcttttga tatctggggc caagggacaa tggtcaccgt ctcgagc       357
```

<210> SEQ ID NO 15
<211> LENGTH: 449
<212> TYPE: PRT
<213> ORGANISM: artificial sequence
<220> FEATURE:
<223> OTHER INFORMATION: Synthesized

<400> SEQUENCE: 15

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Val Ser Ser Gly
             20                  25                  30

Asp Tyr Tyr Trp Thr Trp Ile Arg Gln Ser Pro Gly Lys Gly Leu Glu
         35                  40                  45

Trp Ile Gly His Ile Tyr Tyr Ser Gly Asn Thr Asn Tyr Asn Pro Ser
     50                  55                  60

Leu Lys Ser Arg Leu Thr Ile Ser Ile Asp Thr Ser Lys Thr Gln Phe
 65                  70                  75                  80

Ser Leu Lys Leu Ser Ser Val Thr Ala Ala Asp Thr Ala Ile Tyr Tyr
                 85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 16
<211> LENGTH: 119
<212> TYPE: PRT
<213> ORGANISM: artificial sequence
<220> FEATURE:
<223> OTHER INFORMATION: Synthesized

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115
```

<210> SEQ ID NO 17
<211> LENGTH: 642
<212> TYPE: DNA
<213> ORGANISM: artificial sequence
<220> FEATURE:
<223> OTHER INFORMATION: Synthesized

<400> SEQUENCE: 17

```
gatatccaga tgacccagtc cccgagctcc ctgtccgcct ctgtgggcga tagggtcacc        60
atcacctgcc gtgccagtca gaatattgct actgatgtag cctggtatca acagaaacca       120
ggaaaagctc cgaagcttct gatttactcg gcatccttcc tctactctgg agtcccttct       180
cgcttctctg gtagcggttc cgggacggat ttcactctga ccatcagcag tctgcagccg       240
gaagacttcg caacttatta ctgtcagcaa agtgagccgg agccgtacac gttcggacag       300
ggtaccaagg tggagatcaa acgtacggtg ctgcaccat ctgtcttcat cttcccgcca        360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga aaacacaaa gtctacgcct gcgaagtcac ccatcagggc        600
ctgagctcgc ccgtcacaaa gagcttcaac aggggagagt gt                          642
```

<210> SEQ ID NO 18
<211> LENGTH: 321
<212> TYPE: DNA
<213> ORGANISM: artificial sequence
<220> FEATURE:
<223> OTHER INFORMATION: Synthesized

<400> SEQUENCE: 18

```
gatatccaga tgacccagtc cccgagctcc ctgtccgcct ctgtgggcga tagggtcacc        60
atcacctgcc gtgccagtca gaatattgct actgatgtag cctggtatca acagaaacca       120
ggaaaagctc cgaagcttct gatttactcg gcatccttcc tctactctgg agtcccttct       180
cgcttctctg gtagcggttc cgggacggat ttcactctga ccatcagcag tctgcagccg       240
gaagacttcg caacttatta ctgtcagcaa agtgagccgg agccgtacac gttcggacag       300
ggtaccaagg tggagatcaa a                                                 321
```

<210> SEQ ID NO 19
<211> LENGTH: 214
<212> TYPE: PRT
<213> ORGANISM: artificial sequence
<220> FEATURE:
<223> OTHER INFORMATION: Synthesized

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 20
<211> LENGTH: 107
<212> TYPE: PRT
<213> ORGANISM: artificial sequence
<220> FEATURE:
<223> OTHER INFORMATION: Synthesized

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys
            100                 105

<210> SEQ ID NO 21
<211> LENGTH: 1353
<212> TYPE: DNA
<213> ORGANISM: artificial sequence
<220> FEATURE:
<223> OTHER INFORMATION: Synthesized

<400> SEQUENCE: 21
gaggtgcagc tggtcgagtc tggcggcgga ctggtgcagc cggtggctc tctgcgactg      60 tcttgtgccg cctctggctt caccctcagt ggcgattgga tccactgggt gcgacaggct     120
cccggaaagg gcctggagtg ggtgggtgag atctctgctg ccggtggcta caccgattac     180
gccgactctg tgaagggccg attcaccatc tctgccgaca cctctaagaa caccgcctac     240
ctgcagatga actctctgcg agccgaggac accgctgtgt actactgtgc acgagaaagt     300
agagtttcct tcgaagccgc catggactac tggggccagg gcaccctggt gaccgtgtcc     360
```

-continued

```
tctgctagca ccaagggccc atcggtcttc ccctggcac cctcctccaa gagcacctct      420
gggggcacag cggccctggg ctgcctggtc aaggactact tccccgaacc ggtgacggtg      480
tcgtggaact caggcgccct gaccagcggc gtgcacacct tcccggctgt cctacagtcc      540
tcaggactct actccctcag cagcgtggtg accgtgccct ccagcagctt gggcacccag      600
acctacatct gcaacgtgaa tcacaagccc agcaacacca aggtggacaa gagagttgag      660
cccaaatctt gtgacaaaac tcacacatgc ccaccgtgcc cagcacctga actcctgggg      720
ggaccgtcag tcttcctctt ccccccaaaa cccaaggaca cctcatgat ctcccggacc       780 cctgaggtca catgcgtggt ggtggacgtg agccacgaag accctgaggt caagttcaac      840
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca agtgcaaggt ctccaacaaa gccctcccag cccccatcga gaaaaccatc    1020
tccaaagcca agggcagcc cgagaaccca caggtgtaca ccctgccccc atcccgggag     1080
gagatgacca agaaccaggt cagcctgacc tgcctggtca aaggcttcta tcccagcgac     1140
atcgccgtgg agtgggagag caatgggcag ccggagaaca actacaagac cacgcctccc    1200
gtgctggact ccgacggctc cttcttcctc tatagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                  1353
```

<210> SEQ ID NO 22
<211> LENGTH: 363
<212> TYPE: PRT
<213> ORGANISM: artificial sequence
<220> FEATURE:
<223> OTHER INFORMATION: Synthesized

<400> SEQUENCE: 22

```
Gly Ala Gly Gly Thr Gly Cys Ala Gly Cys Thr Gly Gly Thr Cys Gly
 1               5                  10                  15

Ala Gly Thr Cys Thr Gly Gly Cys Gly Gly Cys Gly Gly Ala Cys Thr
                20                  25                  30

Gly Gly Thr Gly Cys Ala Gly Cys Cys Gly Gly Thr Gly Gly Cys
            35                  40                  45

Thr Cys Thr Cys Thr Gly Cys Gly Ala Cys Gly Thr Cys Thr Thr
        50                  55                  60

Gly Thr Gly Cys Cys Gly Cys Cys Thr Cys Thr Gly Gly Cys Thr Thr
 65                  70                  75                  80

Cys Ala Cys Cys Cys Thr Cys Ala Gly Thr Gly Gly Cys Gly Ala Thr
                85                  90                  95

Thr Gly Gly Ala Thr Cys Cys Ala Cys Thr Gly Gly Gly Thr Gly Cys
                100                 105                 110

Gly Ala Cys Ala Gly Cys Thr Cys Cys Gly Gly Ala Ala Ala
            115                 120                 125

Gly Gly Gly Cys Cys Thr Gly Gly Ala Gly Thr Gly Gly Gly Thr Gly
                130                 135                 140

Gly Gly Thr Gly Ala Gly Ala Thr Cys Thr Gly Cys Thr Gly Thr Gly
145                 150                 155                 160

Cys Cys Gly Gly Thr Gly Gly Cys Thr Ala Cys Ala Cys Cys Gly Ala
                165                 170                 175

Thr Thr Ala Cys Gly Cys Cys Gly Ala Cys Thr Cys Thr Gly Thr Gly
```

```
            180                 185                 190
Ala Ala Gly Gly Gly Cys Cys Gly Ala Thr Thr Cys Ala Cys Cys Ala
        195                 200                 205

Thr Cys Thr Cys Thr Gly Cys Cys Gly Ala Cys Ala Cys Cys Thr Cys
    210                 215                 220

Thr Ala Ala Gly Ala Ala Cys Ala Cys Cys Gly Cys Cys Thr Ala Cys
225                 230                 235                 240

Cys Thr Gly Cys Ala Gly Ala Thr Gly Ala Ala Cys Thr Cys Thr Cys
                245                 250                 255

Thr Gly Cys Gly Ala Gly Cys Cys Gly Ala Gly Gly Ala Cys Ala Cys
            260                 265                 270

Cys Gly Cys Thr Gly Thr Gly Thr Ala Cys Thr Ala Cys Thr Gly Thr
        275                 280                 285

Gly Cys Ala Cys Gly Ala Gly Ala Ala Ala Gly Thr Ala Gly Ala Gly
    290                 295                 300

Thr Thr Thr Cys Cys Thr Thr C

```
              180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 24
<211> LENGTH: 121
<212> TYPE: PRT
<213> ORGANISM: artificial sequence
<220> FEATURE:
<223> OTHER INFORMATION: Synthesized

<400> SEQUENCE: 24

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Leu Ser Gly Asp
            20                  25                  30
Trp Ile His Trp Val Arg Gln Ala Pro Gly Lys Gly Leu Glu Trp Val
        35                  40                  45
Gly Glu Ile Ser Ala Ala Gly Gly Tyr Thr Asp Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
```

```
                    85                  90                  95
Ala Arg Glu Ser Arg Val Ser Phe Glu Ala Ala Met Asp Tyr Trp Gly
                100                 105                 110

Gln Gly Thr Leu Val Thr Val Ser Ser
        115                 120

<210> SEQ ID NO 25
<211> LENGTH: 657
<212> TYPE: DNA
<213> ORGANISM: artificial sequence
<220> FEATURE:
<223> OTHER INFORMATION: Synthesized

<400> SEQUENCE: 25
gatattcaaa tgactcaatc tccttcttct ctttctgctt ctgttggtga tcgtgttact      60
attacttgtc gttcttctca aaatattgtt cattctaatg gtaatactta tcttgattgg    120
tatcaacaaa ctcctggtaa agctcctaaa cttcttattt ataaagtttc taatcgtttt    180
tctggtgttc cttctcgttt ttctggttct ggttctggta ctgattttac ttttactatt    240
tcttctcttc aacctgaaga tattgctact tattattgtt ttcaatattc tcatgttcct    300
tggacttttg gtcaaggtac taaacttcaa attactcgta cggtggctgc accatctgtc    360
ttcatcttcc cgccatctga tgagcagttg aaatctggaa ctgcctctgt tgtgtgcctg    420
ctgaataact ctatcccaga gaggccaaa gtacagtgga aggtggataa cgccctccaa     480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657

<210> SEQ ID NO 26
<211> LENGTH: 336
<212> TYPE: DNA
<213> ORGANISM: artificial sequence
<220> FEATURE:
<223> OTHER INFORMATION: Synthesized

<400> SEQUENCE: 26
gatattcaaa tgactcaatc tccttcttct ctttctgctt ctgttggtga tcgtgttact      60
attacttgtc gttcttctca aaatattgtt cattctaatg gtaatactta tcttgattgg    120
tatcaacaaa ctcctggtaa agctcctaaa cttcttattt ataaagtttc taatcgtttt    180
tctggtgttc cttctcgttt ttctggttct ggttctggta ctgattttac ttttactatt    240
tcttctcttc aacctgaaga tattgctact tattattgtt ttcaatattc tcatgttcct    300
tggacttttg gtcaaggtac taaacttcaa attact                              336

<210> SEQ ID NO 27
<211> LENGTH: 219
<212> TYPE: PRT
<213> ORGANISM: artificial sequence
<220> FEATURE:
<223> OTHER INFORMATION: Synthesized

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
```

```
            35                  40                  45
Pro Lys Leu Leu Ile Tyr Lys Val Ser Asn Arg Phe Ser Gly Val Pro
 50                  55                  60

Ser Arg Phe Ser Gly Ser Gly Ser Gly Thr Asp Phe Thr Phe Thr Ile
 65                  70                  75                  80

Ser Ser Leu Gln Pro Glu Asp Ile Ala Thr Tyr Tyr Cys Phe Gln Tyr
                 85                  90                  95

Ser His Val Pro Trp Thr Phe Gly Gln Gly Thr Lys Leu Gln Ile Thr
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 28
<211> LENGTH: 112
<212> TYPE: PRT
<213> ORGANISM: artificial sequence
<220> FEATURE:
<223> OTHER INFORMATION: Synthesized

<400> SEQUENCE: 28

```
Asp Ile Gln Met Thr Gln Ser Pro Ser Ser Leu Ser Ala Ser Val Gly
 1                   5                  10                  15

Asp Arg Val Thr Ile Thr Cys Arg Ser Ser Gln Asn Ile Val His Ser
                 20                  25                  30

Asn Gly Asn Thr Tyr Leu Asp Trp Tyr Gln Gln Thr Pro Gly Lys Ala
             35                  40                  45

Pro Lys Leu Leu Ile Tyr Lys Val Ser Asn Arg Phe Ser Gly Val Pro
 50                  55                  60

Ser Arg Phe Ser Gly Ser Gly Ser Gly Thr Asp Phe Thr Phe Thr Ile
 65                  70                  75                  80

Ser Ser Leu Gln Pro Glu Asp Ile Ala Thr Tyr Tyr Cys Phe Gln Tyr
                 85                  90                  95

Ser His Val Pro Trp Thr Phe Gly Gln Gly Thr Lys Leu Gln Ile Thr
                100                 105                 110
```

<210> SEQ ID NO 29
<211> LENGTH: 1359
<212> TYPE: DNA
<213> ORGANISM: artificial sequence
<220> FEATURE:
<223> OTHER INFORMATION: Synthesized

<400> SEQUENCE: 29

```
caagttcaac ttcaacaatc tggtgctgaa gttaaaaaac ctggttcttc tgttaaagtt      60
tcttgtaaag cctctggtta tactttact aattattata tttattgggt tcgtcaagct     120
```

```
cctggtcaag gtcttgaatg gattggtggt attaatccta cttctggtgg ttctaatttt    180
aatgaaaaat ttaaaactcg tgttactatt actgttgatg aatctacgaa cactgcttat    240
atggaacttt cttctcttcg ttctgaagat actgcttttt attttgtgc gcgtcaaggt    300 ctttggtttg attctgatgg tcgtggtttt gattttggg gtcaaggttc cactgttact     360
gtctcgagcg ctagcaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaga    660
gttgagccca aatcttgtga caaaactcac acatgccac cgtgcccagc acctgaactc     720 ctgggggac cgtcagtctt cctcttcccc ccaaaaccca aggacaccct catgatctcc     780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
cgggaggaga tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctata gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaa                          1359

<210> SEQ ID NO 30
<211> LENGTH: 369
<212> TYPE: DNA
<213> ORGANISM: artificial sequence
<220> FEATURE:
<223> OTHER INFORMATION: Synthesized

<400> SEQUENCE: 30
caagttcaac ttcaacaatc tggtgctgaa gttaaaaaac tggttcttc tgttaaagtt      60 tcttgtaaag cctctggtta tacttttact aattattata tttattgggt tcgtcaagct    120
cctggtcaag gtcttgaatg gattggtggt attaatccta cttctggtgg ttctaatttt    180
aatgaaaaat ttaaaactcg tgttactatt actgttgatg aatctacgaa cactgcttat    240
atggaacttt cttctcttcg ttctgaagat actgcttttt attttgtgc gcgtcaaggt    300 ctttggtttg attctgatgg tcgtggtttt gattttggg gtcaaggttc cactgttact     360
gtctcgagc                                                            369

<210> SEQ ID NO 31
<211> LENGTH: 453
<212> TYPE: PRT
<213> ORGANISM: artificial sequence
<220> FEATURE:
<223> OTHER INFORMATION: Synthesized

<400> SEQUENCE: 31

Gln Val Gln Leu Gln Gln Ser Gly Ala Glu Val Lys Lys Pro Gly Ser
1               5                   10                  15
```

```
Ser Val Lys Val Ser Cys Lys Ala Ser Gly Tyr Thr Phe Thr Asn Tyr
         20                  25                  30

Tyr Ile Tyr Trp Val Arg Gln Ala Pro Gly Gln Gly Leu Glu Trp Ile
             35                  40                  45

Gly Gly Ile Asn Pro Thr Ser Gly Gly Ser Asn Phe Asn Glu Lys Phe
 50                  55                  60

Lys Thr Arg Val Thr Ile Thr Val Asp Glu Ser Thr Asn Thr Ala Tyr
 65                  70                  75                  80

Met Glu Leu Ser Ser Leu Arg Ser Glu Asp Thr Ala Phe Tyr Phe Cys
                 85                  90                  95

Ala Arg Gln Gly Leu Trp Phe Asp Ser Asp Gly Arg Gly Phe Asp Phe
             100                 105                 110

Trp Gly Gln Gly Ser Thr Val Thr Val Ser Ser Ala Ser Thr Lys Gly
             115                 120                 125

Pro Ser Val Phe Pro Leu Ala Pro Ser Ser Lys Ser Thr Ser Gly Gly
 130                 135                 140

Thr Ala Ala Leu Gly Cys Leu Val Lys Asp Tyr Phe Pro Glu Pro Val
 145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Gln Thr Tyr Ile Cys Asn Val
             195                 200                 205

Asn His Lys Pro Ser Asn Thr Lys Val Asp Lys Arg Val Glu Pro Lys
 210                 215                 220

Ser Cys Asp Lys Thr His Thr Cys Pro Pro Cys Pro Ala Pro Glu Leu
 225                 230                 235                 240

Leu Gly Gly Pro Ser Val Phe Leu Phe Pro Pro Lys Pro Lys Asp Thr
                 245                 250                 255

Leu Met Ile Ser Arg Thr Pro Glu Val Thr Cys Val Val Val Asp Val
             260                 265                 270

Ser His Glu Asp Pro Glu Val Lys Phe Asn Trp Tyr Val Asp Gly Val
             275                 280                 285

Glu Val His Asn Ala Lys Thr Lys Pro Arg Glu Glu Gln Tyr Asn Ser
 290                 295                 300

Thr Tyr Arg Val Val Ser Val Leu Thr Val Leu His Gln Asp Trp Leu
 305                 310                 315                 320

Asn Gly Lys Glu Tyr Lys Cys Lys Val Ser Asn Lys Ala Leu Pro Ala
                 325                 330                 335

Pro Ile Glu Lys Thr Ile Ser Lys Ala Lys Gly Gln Pro Arg Glu Pro
             340                 345                 350

Gln Val Tyr Thr Leu Pro Pro Ser Arg Glu Glu Met Thr Lys Asn Gln
             355                 360                 365

Val Ser Leu Thr Cys Leu Val Lys Gly Phe Tyr Pro Ser Asp Ile Ala
 370                 375                 380

Val Glu Trp Glu Ser Asn Gly Gln Pro Glu Asn Asn Tyr Lys Thr Thr
 385                 390                 395                 400

Pro Pro Val Leu Asp Ser Asp Gly Ser Phe Phe Leu Tyr Ser Lys Leu
                 405                 410                 415

Thr Val Asp Lys Ser Arg Trp Gln Gln Gly Asn Val Phe Ser Cys Ser
             420                 425                 430
```

```
Val Met His Glu Ala Leu His Asn His Tyr Thr Gln Lys Ser Leu Ser
        435                 440                 445

Leu Ser Pro Gly Lys
    450
```

<210> SEQ ID NO 32
<211> LENGTH: 123
<212> TYPE: PRT
<213> ORGANISM: artificial sequence
<220> FEATURE:
<223> OTHER INFORMATION: Synthesized

<400> SEQUENCE: 32

```
Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
            100                 105                 110

Trp Gly Gln Gly Ser Thr Val Thr Val Ser Ser
        115                 120
```

<210> SEQ ID NO 33
<211> LENGTH: 657
<212> TYPE: DNA
<213> ORGANISM: artificial sequence
<220> FEATURE:
<223> OTHER INFORMATION: Synthesized

<400> SEQUENCE: 33

```
gatattcaaa tgactcaatc tccttcttct ctttctgctt ctgttggtga tcgtgttact    60
attacttgtc gttcttctca aaatattgtt cattctaatg gtaatactta tcttgattgg   120
tatcaacaaa ctcctggtaa agctcctaaa cttcttattt ataaagtttc taatcgtttt   180
tctggtgttc cttctcgttt ttctggttct ggttctggta ctgattttac ttttactatt   240
tcttctcttc aacctgaaga tattgctact tattattgtt ttcaatattc tcatgttcct   300 tggactttg tcaaggtac taaacttcaa attactcgta cggtggctgc accatctgtc    360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt     657
```

<210> SEQ ID NO 34
<211> LENGTH: 336
<212> TYPE: DNA
<213> ORGANISM: artificial sequence
<220> FEATURE:
<223> OTHER INFORMATION: Synthesized

<400> SEQUENCE: 34

```
gatattcaaa tgactcaatc tccttcttct ctttctgctt ctgttggtga tcgtgttact    60
attacttgtc gttcttctca aaatattgtt cattctaatg gtaatactta tcttgattgg   120
tatcaacaaa ctcctggtaa agctcctaaa cttcttattt ataaagtttc taatcgtttt   180
tctggtgttc cttctcgttt ttctggttct ggttctggta ctgattttac ttttactatt   240
tcttctcttc aacctgaaga tattgctact tattattgtt ttcaatattc tcatgttcct   300
tggactttg gtcaaggtac taaacttcaa attact                              336
```

<210> SEQ ID NO 35
<211> LENGTH: 218
<212> TYPE: PRT
<213> ORGANISM: artificial sequence
<220> FEATURE:
<223> OTHER INFORMATION: Synthesized

<400> SEQUENCE: 35

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
             20                  25                  30

Asn Phe Val Ser Trp Tyr Gln Gln His Pro Gly Lys Ala Pro Lys Leu
         35                  40                  45

Met Ile Tyr Asp Val Ser Asp Arg Pro Ser Gly Val Ser Asp Arg Phe
     50                  55                  60

Ser Gly Ser Lys Ser Gly Asn Thr Ala Ser Leu Ile Ile Ser Gly Leu
 65                  70                  75                  80

Gln Ala Asp Asp Glu Ala Asp Tyr Tyr Cys Ser Ser Tyr Gly Ser Ser
                 85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 36
<211> LENGTH: 111
<212> TYPE: PRT
<213> ORGANISM: artificial sequence
<220> FEATURE:
<223> OTHER INFORMATION: Synthesized

<400> SEQUENCE: 36

```
Gln Ser Ala Leu Thr Gln Pro Ala Ser Val Ser Gly Ser Pro Gly Gln
 1               5                  10                  15
```

Ser Ile Thr Ile Ser Cys Thr Gly Thr Ser Ser Asp Val Gly Gly Tyr
        20                  25                  30

Asn Phe Val Ser Trp Tyr Gln Gln His Pro Gly Lys Ala Pro Lys Leu
    35                  40                  45

Met Ile Tyr Asp Val Ser Asp Arg Pro Ser Gly Val Ser Asp Arg Phe
50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
            100                 105                 110

<210> SEQ ID NO 37
<211> LENGTH: 1356
<212> TYPE: DNA
<213> ORGANISM: artificial sequence
<220> FEATURE:
<223> OTHER INFORMATION: Synthesized

<400> SEQUENCE: 37

```
caggtgcagc tgcagcagag cggcgccgag gtgaagaagc ccggcagcag cgtgaaggtg        60
agctgcaagg ccagcggcta caccttcacc aactactaca tctactgggt gcggcaggcc       120
cccggccagg gcctggagtg gatcggcggc atcaacccca ccagcggcgg cagcaacttc       180
aacgagaagt tcaagacccg ggtgaccatc accgccgacg agagcagcac caccgcctac       240
atggagctga gcagcctgcg gagcgaggac accgccttct acttctgcac ccggcagggc       300
ctgtggttcg acagcgacgg ccggggcttc gacttctggg gccagggcac caccgtgacc       360
gtgagcagcg ctagcaccaa gggcccatcg gtcttccccc tggcaccctc ctccaagagc       420
acctctgggg gcacagcggc cctgggctgc ctggtcaagg actacttccc cgaaccggtg       480
acggtgtcgt ggaactcagg cgccctgacc agcggcgtgc acaccttccc ggctgtccta       540
cagtcctcag gactctactc cctcagcagc gtggtgaccg tgccctccag cagcttgggc       600
acccagacct acatctgcaa cgtgaatcac aagcccagca caccaaggt ggacaagaga       660
gttgagccca aatcttgtga caaaactcac acatgcccac cgtgcccagc acctgaactc       720
ctggggggac cgtcagtctt cctcttcccc ccaaaaccca aggacaccct catgatctcc       780
cggacccctg aggtcacatg cgtggtggtg gacgtgagcc acgaagaccc tgaggtcaag       840
ttcaactggt acgtggacgg cgtggaggtg cataatgcca agacaaagcc gcgggaggag       900
cagtacaaca gcacgtaccg tgtggtcagc gtcctcaccg tcctgcacca ggactggctg       960
aatggcaagg agtacaagtg caaggtctcc aacaaagccc tcccagcccc catcgagaaa      1020
accatctcca aagccaaagg gcagccccga gaaccacagg tgtacaccct gcccccatcc      1080
cgggatgagc tgaccaagaa ccaggtcagc ctgacctgcc tggtcaaagg cttctatccc      1140
agcgacatcg ccgtggagtg ggagagcaat gggcagccgg agaacaacta caagaccacg      1200
cctcccgtgc tggactccga cggctccttc ttcctctata gcaagctcac cgtggacaag      1260
agcaggtggc agcaggggaa cgtcttctca tgctccgtga tgcatgaggc tctgcacaac      1320
cactacacgc agaagagcct ctccctgtct ccgggt                                1356
```

<210> SEQ ID NO 38
<211> LENGTH: 369
<212> TYPE: DNA

<213> ORGANISM: artificial sequence
<220> FEATURE:
<223> OTHER INFORMATION: Synthesized

<400> SEQUENCE: 38

```
caggtgcagc tgcagcagag cggcgccgag gtgaagaagc ccggcagcag cgtgaaggtg    60
agctgcaagg ccagcggcta caccttcacc aactactaca tctactgggt gcggcaggcc   120
cccggccagg gcctggagtg gatcggcggc atcaaccccc caagcggcgg cagcaacttc   180
aacgagaagt tcaagacccg ggtgaccatc accgccgacg agagcagcac caccgcctac   240
atggagctga gcagcctgcg gagcgaggac accgccttct acttctgcac ccggcagggc   300
ctgtggttcg acagcgacgg ccggggcttc gacttctggg gccagggcac caccgtgacc   360
gtgagcagc                                                           369
```

<210> SEQ ID NO 39
<211> LENGTH: 452
<212> TYPE: PRT
<213> ORGANISM: artificial sequence
<220> FEATURE:
<223> OTHER INFORMATION: Synthesized

<400> SEQUENCE: 39

```
Gln Val Gln Leu Gln Gln Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
```

```
              260                 265                 270
Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 40
<211> LENGTH: 123
<212> TYPE: PRT
<213> ORGANISM: artificial sequence
<220> FEATURE:
<223> OTHER INFORMATION: Synthesized

<400> SEQUENCE: 40

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser
        115                 120

<210> SEQ ID NO 41
<211> LENGTH: 642
<212> TYPE: DNA
<213> ORGANISM: artificial sequence
<220> FEATURE:
<223> OTHER INFORMATION: Synthesized
```

<400> SEQUENCE: 41

```
gacatcttgc tgactcagtc tccagtcatc ctgtctgtga gtccaggaga aagagtcagt     60
ttctcctgca gggccagtca gagtattggc acaaacatac actggtatca gcaaagaaca    120
aatggttctc caaggcttct cataaagtat gcttctgagt ctatctctgg gattccttcc    180
aggtttagtg gcagtggatc agggacagat tttactctta gcatcaacag tgtggagtct    240
gaagatattg cagattatta ctgtcaacaa aataataact ggccaaccac gttcggtgct    300
gggaccaagc tggagctgaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540
ctgagcaaag cagactacga aaacacaaa gtctacgcct gcgaagtcac ccatcagggc    600
ctgagctcgc ccgtcacaaa gagcttcaac aggggagagt gt                       642
```

<210> SEQ ID NO 42
<211> LENGTH: 321
<212> TYPE: DNA
<213> ORGANISM: artificial sequence
<220> FEATURE:
<223> OTHER INFORMATION: Synthesized

<400> SEQUENCE: 42

```
gacatcttgc tgactcagtc tccagtcatc ctgtctgtga gtccaggaga aagagtcagt     60
ttctcctgca gggccagtca gagtattggc acaaacatac actggtatca gcaaagaaca    120
aatggttctc caaggcttct cataaagtat gcttctgagt ctatctctgg gattccttcc    180
aggtttagtg gcagtggatc agggacagat tttactctta gcatcaacag tgtggagtct    240
gaagatattg cagattatta ctgtcaacaa aataataact ggccaaccac gttcggtgct    300
gggaccaagc tggagctgaa a                                              321
```

<210> SEQ ID NO 43
<211> LENGTH: 214
<212> TYPE: PRT
<213> ORGANISM: artificial sequence
<220> FEATURE:
<223> OTHER INFORMATION: Synthesized

<400> SEQUENCE: 43

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
```

```
                    115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
210

<210> SEQ ID NO 44
<211> LENGTH: 107
<212> TYPE: PRT
<213> ORGANISM: artificial sequence
<220> FEATURE:
<223> OTHER INFORMATION: Synthesized

<400> SEQUENCE: 44

Asp Ile Leu Leu Thr Gln Ser Pro Val Ile Leu Ser Val Ser Pro Gly
1               5                   10                  15
Glu Arg Val Ser Phe Ser Cys Arg Ala Ser Gln Ser Ile Gly Thr Asn
            20                  25                  30
Ile His Trp Tyr Gln Gln Arg Thr Asn Gly Ser Pro Arg Leu Leu Ile
        35                  40                  45
Lys Tyr Ala Ser Glu Ser Ile Ser Gly Ile Pro Ser Arg Phe Ser Gly
    50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Asn Asn Asn Trp Pro Thr
                85                  90                  95
Thr Phe Gly Ala Gly Thr Lys Leu Glu Leu Lys
            100                 105

<210> SEQ ID NO 45
<211> LENGTH: 1347
<212> TYPE: DNA
<213> ORGANISM: artificial sequence
<220> FEATURE:
<223> OTHER INFORMATION: Synthesized

<400> SEQUENCE: 45
caggtgcagc tgaagcagtc aggacctggc ctagtgcagc cctcacagag cctgtccatc      60
acctgcacag tctctggttt ctcattaact aactatggtg tacactgggt tcgccagtct     120
ccaggaaagg gtctggagtg gctgggagtg atatggagtg gtggaaacac agactataat     180
acacctttca catccagact gagcatcaac aaggacaatt ccaagagcca agttttcttt     240
aaaatgaaca gtctgcaatc taatgacaca gccatatatt actgtgccag agccctcacc     300
tactatgatt acgagtttgc ttactggggc caagggactc tggtcactgt ctctagcgct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
```

```
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gaccctgag    780 gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                        1347

<210> SEQ ID NO 46
<211> LENGTH: 357
<212> TYPE: DNA
<213> ORGANISM: artificial sequence
<220> FEATURE:
<223> OTHER INFORMATION: Synthesized

<400> SEQUENCE: 46
caggtgcagc tgaagcagtc aggacctggc ctagtgcagc cctcacagag cctgtccatc     60
acctgcacag tctctggttt ctcattaact aactatggtg tacactgggt tcgccagtct    120
ccaggaaagg gtctggagtg gctgggagtg atatggagtg gtggaaacac agactataat    180
acacctttca catccagact gagcatcaac aaggacaatt ccaagagcca agttttcttt    240
aaaatgaaca gtctgcaatc taatgacaca gccatatatt actgtgccag agccctcacc    300
tactatgatt acgagtttgc ttactggggc caagggactc tggtcactgt ctctagc       357

<210> SEQ ID NO 47
<211> LENGTH: 449
<212> TYPE: PRT
<213> ORGANISM: artificial sequence
<220> FEATURE:
<223> OTHER INFORMATION: Synthesized

<400> SEQUENCE: 47

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
```

```
                100             105             110
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135             140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 48
<211> LENGTH: 119
<212> TYPE: PRT
<213> ORGANISM: artificial sequence
<220> FEATURE:
<223> OTHER INFORMATION: Synthesized

<400> SEQUENCE: 48

Gln Val Gln Leu Lys Gln Ser Gly Pro Gly Leu Val Gln Pro Ser Gln
1               5                   10                  15
```

```
Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115
```

<210> SEQ ID NO 49
<211> LENGTH: 654
<212> TYPE: DNA
<213> ORGANISM: artificial sequence
<220> FEATURE:
<223> OTHER INFORMATION: Synthesized

<400> SEQUENCE: 49

```
cagtctgccc tgactcagcc tgcctccgtg tctgggtctc ctggacagtc gatcaccatc      60
tcctgcactg gaaccagcag tgacgttggt ggttataact tgtctcctg gtaccaacaa     120
cacccaggca aagcccccaa actcatgatc tatgatgtca gtgatcggcc ctcaggggtg    180
tctgatcgct tctccggctc caagtctggc aacacggcct ccctgatcat ctctggcctc    240
caggctgacg acgaggctga ttattactgc agctcatatg ggagcagcag cactcatgtg    300
attttcggcg agggaccaa gctgaccgtc ctacgtacgg tggctgcacc atctgtcttc     360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca aagtctacgc ctgcgaagtc    600
acccatcagg gcctgagctc gcccgtcaca aagagcttca caggggaga gtgt           654
```

<210> SEQ ID NO 50
<211> LENGTH: 333
<212> TYPE: DNA
<213> ORGANISM: artificial sequence
<220> FEATURE:
<223> OTHER INFORMATION: Synthesized

<400> SEQUENCE: 50

```
cagtctgccc tgactcagcc tgcctccgtg tctgggtctc ctggacagtc gatcaccatc      60
tcctgcactg gaaccagcag tgacgttggt ggttataact tgtctcctg gtaccaacaa     120
cacccaggca aagcccccaa actcatgatc tatgatgtca gtgatcggcc ctcaggggtg    180
tctgatcgct tctccggctc caagtctggc aacacggcct ccctgatcat ctctggcctc    240
caggctgacg acgaggctga ttattactgc agctcatatg ggagcagcag cactcatgtg    300
attttcggcg agggaccaa gctgaccgtc cta                                   333
```

<210> SEQ ID NO 51
<211> LENGTH: 218

```
<212> TYPE: PRT
<213> ORGANISM: artificial sequence
<220> FEATURE:
<223> OTHER INFORMATION: Synthesized

<400> SEQUENCE: 51

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 52
<211> LENGTH: 111
<212> TYPE: PRT
<213> ORGANISM: artificial sequence
<220> FEATURE:
<223> OTHER INFORMATION: Synthesized

<400> SEQUENCE: 52

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
            100                 105                 110
```

<210> SEQ ID NO 53
<211> LENGTH: 2100
<212> TYPE: DNA
<213> ORGANISM: artificial sequence
<220> FEATURE:
<223> OTHER INFORMATION: Synthesized

<400> SEQUENCE: 53

```
caggtgcagc tgcaggagtc gggggggaggc ctggtcaagc ctggagggtc cctgagactc        60
tcctgtgcag cctctggatt cacctttagt agttattgga tgagctgggt ccgccaggct       120
ccagggaagg ggctggagtg ggtggccaac ataaaccgcg atggaagtgc gagttactat       180
gtggactctg tgaagggccg attcaccatc tccagagacg acgccaagaa ctcactgtat       240
ctgcaaatga acagcctgag agctgaggac acggctgtgt attactgtgc gagagatcgt       300
ggggtgggct acttcgatct ctggggccgt ggcaccctgg tcaccgtctc gagcgctagc       360
accaagggcc catcggtctt ccccctggca ccctcctcca agagcacctc tgggggcaca       420
gcggccctgg gctgcctggt caaggactac ttccccgaac cggtgacggt gtcgtggaac       480
tcaggcgccc tgaccagcgg cgtgcacacc ttcccggctg tcctacagtc ctcaggactc       540
tactccctca gcagcgtggt gaccgtgccc tccagcagct gggcacccca gacctacatc       600
tgcaacgtga atcacaagcc cagcaacacc aaggtggaca gagagttgag cccaaatctt       660
tgtgacaaaa ctcacacatg cccaccgtgc ccagcacctg aactcctggg gggaccgtca       720
gtcttcctct tccccccaaa acccaaggac accctcatga tctcccggac ccctgaggtc       780
acatgcgtgg tggtggacgt gagccacgaa gaccctgagg tcaagttcaa ctggtacgtg       840
gacggcgtgg aggtgcataa tgccaagaca aagccgcggg aggagcagta caacagcacg       900
taccgtgtgg tcagcgtcct caccgtcctg caccaggact ggctgaatgg caaggagtac       960
aagtgcaagg tctccaacaa agccctccca gcccccatcg agaaaaccat ctccaaagcc      1020
aaagggcagc cccgagaacc acaggtgtac accctgcccc catcccggga ggagatgacc      1080
aagaaccagg tcagcctgac ctgcctggtc aaaggcttct atcccagcga catcgccgtg      1140
gagtgggaga gcaatgggca gccggagaac aactacaaga ccacgcctcc cgtgctggac      1200
tccgacggct ccttcttcct ctatagcaag ctcaccgtgg acaagagcag gtggcagcag      1260
gggaacgtct tctcatgctc cgtgatgcat gaggctctgc acaaccacta cacgcagaag      1320
agcctctccc tgtctccggg taaaggcggt ggaggatccg gcggtggtgg atcacaggtg      1380
cagctgcagg agtcgggccc aggactggtg aagccttcgg agaccctgtc cctcacctgc      1440
actgtctctg gtggctccgt cagcagtggt gattactact ggacctggat acggcagtcc      1500
ccagggaagg gactggagtg gattggacac atctattaca gtgggaacac caattataac      1560
ccctccctca gagccgact caccatatca attgacacgt ccaagactca gttctccctg      1620
aagctgagtt ctgtgaccgc tgcggacacg gccatttatt actgtgtgcg agatcgagtg      1680
actggtgctt ttgatatctg ggggccaaggg acaatggtca ccgtctcgag cggtggaggc      1740
ggttcaggcg gaggtggttc cggcggtggc ggctccgaca tccagatgac ccagtctcca      1800
tcctccctgt ctgcatctgt aggagacaga gtcaccatca cttgccaggc gagtcaggac      1860
atcagcaact attaaattg gtatcagcag aaaccaggga agcccctaa actcctgatc      1920
tacgatgcat ccaatttgga aacaggggtc ccatcaaggt tcagtggaag tggatctggg      1980
acagatttta ctttcaccat cagcagcctg cagcctgaag atattgcaac atatttctgt      2040
```
caacactttg atcatctccc gctcgctttc ggcggaggga ccaaggtgga aattaaacgt    2100

<210> SEQ ID NO 54
<211> LENGTH: 354
<212> TYPE: DNA
<213> ORGANISM: artificial sequence
<220> FEATURE:
<223> OTHER INFORMATION: Synthesized

<400> SEQUENCE: 54
caggtgcagc tgcaggagtc ggggggaggc ctggtcaagc ctggagggtc cctgagactc     60
tcctgtgcag cctctggatt caccttagt agttattgga tgagctgggt ccgccaggct    120
ccagggaagg ggctggagtg ggtggccaac ataaaccgcg atggaagtgc gagttactat    180
gtggactctg tgaagggccg attcaccatc tccagagacg acgccaagaa ctcactgtat    240
ctgcaaatga acagcctgag agctgaggac acggctgtgt attactgtgc gagagatcgt    300
ggggtgggct acttcgatct ctggggccgt ggcaccctgg tcaccgtctc gagc          354

<210> SEQ ID NO 55
<211> LENGTH: 726
<212> TYPE: DNA
<213> ORGANISM: artificial sequence
<220> FEATURE:
<223> OTHER INFORMATION: Synthesized

<400> SEQUENCE: 55
caggtgcagc tgcaggagtc gggcccagga ctggtgaagc cttcggagac cctgtccctc     60
acctgcactg tctctggtgg ctccgtcagc agtggtgatt actactggac ctggatacgg    120
cagtccccag ggaagggact ggagtggatt ggacacatct attacagtgg gaacaccaat    180
tataacccct ccctcaagag ccgactcacc atatcaattg acacgtccaa gactcagttc    240
tccctgaagc tgagttctgt gaccgctgcg gacacggcca tttattactg tgtgcgagat    300
cgagtgactg gtgcttttga tatctggggc caagggacaa tggtcaccgt ctcgagcggt    360
ggaggcggtt caggcggagg tggttccggc ggtggcggct ccgacatcca gatgacccag    420
tctccatcct ccctgtctgc atctgtagga gacagagtca ccatcacttg ccaggcgagt    480
caggacatca gcaactattt aaattggtat cagcagaaac agggaaaagc ccctaaactc    540
ctgatctacg atgcatccaa tttggaaaca ggggtcccat caaggttcag tggaagtgga    600
tctgggacag attttacttt caccatcagc agcctgcagc ctgaagatat tgcaacatat    660
ttctgtcaac actttgatca tctcccgctc gctttcggcg agggaccaa ggtggaaatt     720
aaacgt                                                               726

<210> SEQ ID NO 56
<211> LENGTH: 700
<212> TYPE: PRT
<213> ORGANISM: artificial sequence
<220> FEATURE:
<223> OTHER INFORMATION: Synthesized

<400> SEQUENCE: 56

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

-continued

```
Ala Asn Ile Asn Arg Asp Gly Ser Ala Ser Tyr Tyr Val Asp Ser Val
 50                  55                  60
Lys Gly Arg Phe Thr Ile Ser Arg Asp Asp Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Asp Arg Gly Val Gly Tyr Phe Asp Leu Trp Gly Arg Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
                180                 185                 190
Ser Leu Gly Thr Gln Thr Tyr Ile Cys Asn Val Asn His Lys Pro Ser
            195                 200                 205
Asn Thr Lys Val Asp Lys Arg Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445
Gly Gly Gly Gly Ser Gly Gly Gly Ser Gln Val Gln Leu Gln Glu
450                 455                 460
Ser Gly Pro Gly Leu Val Lys Pro Ser Glu Thr Leu Ser Leu Thr Cys
```

```
                465                 470                 475                 480
Thr Val Ser Gly Gly Ser Val Ser Ser Gly Asp Tyr Tyr Trp Thr Trp
                    485                 490                 495
Ile Arg Gln Ser Pro Gly Lys Gly Leu Glu Trp Ile Gly His Ile Tyr
                    500                 505                 510
Tyr Ser Gly Asn Thr Asn Tyr Asn Pro Ser Leu Lys Ser Arg Leu Thr
                    515                 520                 525
Ile Ser Ile Asp Thr Ser Lys Thr Gln Phe Ser Leu Lys Leu Ser Ser
                    530                 535                 540
Val Thr Ala Ala Asp Thr Ala Ile Tyr Tyr Cys Val Arg Asp Arg Val
545                 550                 555                 560
Thr Gly Ala Phe Asp Ile Trp Gly Gln Gly Thr Met Val Thr Val Ser
                    565                 570                 575
Ser Gly Gly Gly Gly Ser Gly Gly Gly Ser Gly Gly Gly Gly Ser
                    580                 585                 590
Asp Ile Gln Met Thr Gln Ser Pro Ser Ser Leu Ser Ala Ser Val Gly
                    595                 600                 605
Asp Arg Val Thr Ile Thr Cys Gln Ala Ser Gln Asp Ile Ser Asn Tyr
                    610                 615                 620
Leu Asn Trp Tyr Gln Gln Lys Pro Gly Lys Ala Pro Lys Leu Leu Ile
625                 630                 635                 640
Tyr Asp Ala Ser Asn Leu Glu Thr Gly Val Pro Ser Arg Phe Ser Gly
                    645                 650                 655
Ser Gly Ser Gly Thr Asp Phe Thr Phe Thr Ile Ser Ser Leu Gln Pro
                    660                 665                 670
Glu Asp Ile Ala Thr Tyr Phe Cys Gln His Phe Asp His Leu Pro Leu
                    675                 680                 685
Ala Phe Gly Gly Gly Thr Lys Val Glu Ile Lys Arg
                    690                 695                 700

<210> SEQ ID NO 57
<211> LENGTH: 118
<212> TYPE: PRT
<213> ORGANISM: artificial sequence
<220> FEATURE:
<223> OTHER INFORMATION: Synthesized

<400> SEQUENCE: 57

Gln Val Gln Leu Gln Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
                20                  25                  30
Trp Met Ser Trp Val Arg Gln Ala Pro Gly Lys Gly Leu Glu Trp Val
            35                  40                  45
Ala Asn Ile Asn Arg Asp Gly Ser Ala Ser Tyr Tyr Val Asp Ser Val
        50                  55                  60
Lys Gly Arg Phe Thr Ile Ser Arg Asp Asp Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Arg Gly Val Gly Tyr Phe Asp Leu Trp Gly Arg Gly Thr
                    100                 105                 110
Leu Val Thr Val Ser Ser
                115
```

<210> SEQ ID NO 58
<211> LENGTH: 242
<212> TYPE: PRT
<213> ORGANISM: artificial sequence
<220> FEATURE:
<223> OTHER INFORMATION: Synthesized

<400> SEQUENCE: 58

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Val Ser Ser Gly
            20                  25                  30
Asp Tyr Tyr Trp Thr Trp Ile Arg Gln Ser Pro Gly Lys Gly Leu Glu
        35                  40                  45
Trp Ile Gly His Ile Tyr Tyr Ser Gly Asn Thr Asn Tyr Asn Pro Ser
    50                  55                  60
Leu Lys Ser Arg Leu Thr Ile Ser Ile Asp Thr Ser Lys Thr Gln Phe
65                  70                  75                  80
Ser Leu Lys Leu Ser Ser Val Thr Ala Ala Asp Thr Ala Ile Tyr Tyr
                85                  90                  95
Cys Val Arg Asp Arg Val Thr Gly Ala Phe Asp Ile Trp Gly Gln Gly
            100                 105                 110
Thr Met Val Thr Val Ser Ser Gly Gly Gly Ser Gly Gly Gly Gly
        115                 120                 125
Ser Gly Gly Gly Gly Ser Asp Ile Gln Met Thr Gln Ser Pro Ser Ser
    130                 135                 140
Leu Ser Ala Ser Val Gly Asp Arg Val Thr Ile Thr Cys Gln Ala Ser
145                 150                 155                 160
Gln Asp Ile Ser Asn Tyr Leu Asn Trp Tyr Gln Gln Lys Pro Gly Lys
                165                 170                 175
Ala Pro Lys Leu Leu Ile Tyr Asp Ala Ser Asn Leu Glu Thr Gly Val
            180                 185                 190
Pro Ser Arg Phe Ser Gly Ser Gly Ser Gly Thr Asp Phe Thr Phe Thr
        195                 200                 205
Ile Ser Ser Leu Gln Pro Glu Asp Ile Ala Thr Tyr Phe Cys Gln His
    210                 215                 220
Phe Asp His Leu Pro Leu Ala Phe Gly Gly Gly Thr Lys Val Glu Ile
225                 230                 235                 240
Lys Arg
```

<210> SEQ ID NO 59
<211> LENGTH: 642
<212> TYPE: DNA
<213> ORGANISM: artificial sequence
<220> FEATURE:
<223> OTHER INFORMATION: Synthesized

<400> SEQUENCE: 59

```
gacatccaga tgacccagtc tccatcctcc ctgtctgcat ctgtaggaga cagagtcacc      60
atcacttgcc aggcgagtca ggacatcagc aactatttaa attggtatca gcagaaacca     120
gggaaagccc ctaaactcct gatctacgat gcatccaatt tggaaacagg gtcccatca     180 aggttcagtg gaagtggatc tgggacagat tttactttca ccatcagcag cctgcagcct     240
gaagatattg caacatattt ctgtcaacac tttgatcatc tcccgctcgc tttcggcgga     300
gggaccaagg tggaaattaa acgtacggtg gctgcaccat ctgtcttcat cttcccgcca     360
tctgatgagc agttgaaatc tggaactgcc tctgttgtgt gcctgctgaa taacttctat     420
```

```
cccagagagg ccaaagtaca gtggaaggtg gataacgccc tccaatcggg taactcccag    480
gagagtgtca cagagcagga cagcaaggac agcacctaca gcctcagcag cacccctgacg   540 ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 60
<211> LENGTH: 321
<212> TYPE: DNA
<213> ORGANISM: artificial sequence
<220> FEATURE:
<223> OTHER INFORMATION: Synthesized

<400> SEQUENCE: 60

```
gacatccaga tgacccagtc tccatcctcc ctgtctgcat ctgtaggaga cagagtcacc     60
atcacttgcc aggcgagtca ggacatcagc aactatttaa attggtatca gcagaaacca   120
gggaaagccc ctaaactcct gatctacgat gcatccaatt tggaaacagg ggtcccatca   180
aggttcagtg gaagtggatc tgggacagat tttactttca ccatcagcag cctgcagcct   240
gaagatattg caacatattt ctgtcaaaca tttgatcatc tcccgctcgc tttcggcgga   300
gggaccaagg tggaaattaa a                                              321
```

<210> SEQ ID NO 61
<211> LENGTH: 214
<212> TYPE: PRT
<213> ORGANISM: artificial sequence
<220> FEATURE:
<223> OTHER INFORMATION: Synthesized

<400> SEQUENCE: 61

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 62
<211> LENGTH: 107
<212> TYPE: PRT
<213> ORGANISM: artificial sequence
<220> FEATURE:
<223> OTHER INFORMATION: Synthesized

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 63
<211> LENGTH: 2109
<212> TYPE: DNA
<213> ORGANISM: artificial sequence
<220> FEATURE:
<223> OTHER INFORMATION: Synthesized

<400> SEQUENCE: 63
caggtgcagc tgcaggagtc gggcccagga ctggtgaagc cttcggagac cctgtccctc      60
acctgcactg tctctggtgg ctccgtcagc agtggtgatt actactggac ctggatccgg     120
cagtccccag ggaagggact ggagtggatt ggacacatct attacagtgg gaacaccaat     180
tataaccccc tccctcaagag ccgactcacc atatcaattg acacgtccaa gactcagttc    240
tccctgaagc tgagttctgt gaccgctgcg gacacggcca tttattactg tgcgagat      300 cgagtgactg gtgcttttga tatctgggc aagggacaa tggtcaccgt ctcgagcgct       360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gaccctgag    780 gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa   1020

```
gccaaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctatagc aagctcaccg tggacaagag caggtggcag    1260
caggggaacg tcttctcatg ctccgtgatg catgaggctc tgcacaacca ctacacgcag    1320
aagagcctct ccctgtctcc gggtaaaggc ggtggaggat ccggcggtgg tggatcacag    1380
gtgcagctgc aggagtcggg gggaggcctg gtcaagcctg agggtccct  gagactctcc    1440 tgtgcagcct ctggattcac ctttagtagt tattggatga gctgggtccg ccaggctcca    1500 gggaagggc tggagtgggt ggccaacata aaccgcgatg gaagtgcgag ttactatgtg    1560
gactctgtga agggccgatt caccatctcc agagacgacg ccaagaactc actgtatctg    1620
caaatgaaca gcctgagagc tgaggacacg gctgtgtatt actgtgcgag agatcgtggg    1680
gtgggctact tcgatctctg gggccgtggc accctggtca ccgtctcgag cggtggaggc    1740
ggttcaggcg gaggtggttc cggcggtggc ggctcccagt ctgccctgac tcagcctgcc    1800
tccgtgtctg gtctcctgg  acagtcgatc accatctcct gcactggaac cagcagtgac    1860
gttggtggtt ataactttgt ctcctggtac caacaacacc caggcaaagc ccccaaactc    1920
atgatctatg atgtcagtga tcggccctca ggggtgtctg atcgcttctc cggctccaag    1980
tctggcaaca cggcctccct gatcatctct ggcctccagg ctgacgacga ggctgattat    2040
tactgcagct catatgggag cagcagcact catgtgattt tcggcggagg gaccaaggtg    2100
accgtccta                                                            2109

<210> SEQ ID NO 64
<211> LENGTH: 357
<212> TYPE: DNA
<213> ORGANISM: artificial sequence
<220> FEATURE:
<223> OTHER INFORMATION: Synthesized

<400> SEQUENCE: 64
caggtgcagc tgcaggagtc gggcccagga ctggtgaagc cttcggagac cctgtccctc     60
acctgcactg tctctggtgg ctccgtcagc agtggtgatt actactggac ctggatccgg    120
cagtccccag ggaagggact ggagtggatt ggacacatct attacagtgg gaacaccaat    180 tataaccct  ccctcaagag ccgactcacc atatcaattg acacgtccaa gactcagttc    240
tccctgaagc tgagttctgt gaccgctgcg gacacggcca tttattactg tgtgcgagat    300
cgagtgactg gtgcttttga tatctgggc  caagggacaa tggtcaccgt ctcgagc      357

<210> SEQ ID NO 65
<211> LENGTH: 732
<212> TYPE: DNA
<213> ORGANISM: artificial sequence
<220> FEATURE:
<223> OTHER INFORMATION: Synthesized

<400> SEQUENCE: 65
caggtgcagc tgcaggagtc ggggggaggc ctggtcaagc ctggagggtc cctgagactc     60
tcctgtgcag cctctggatt cacctttagt agttattgga tgagctgggt ccgccaggct    120
ccagggaagg gctggagtg  gtggccaac ataaaccgcg atggaagtgc gagttactat    180
gtggactctg tgaagggccg attcaccatc tccagagacg acgccaagaa ctcactgtat    240
ctgcaaatga acagcctgag agctgaggac acggctgtgt attactgtgc gagagatcgt    300
```

```
ggggtgggct acttcgatct ctggggccgt ggcaccctgg tcaccgtctc gagcggtgga       360
ggcggttcag gcggaggtgg ttccggcggt ggcggctccc agtctgccct gactcagcct       420
gcctccgtgt ctgggtctcc tggacagtcg atcaccatct cctgcactgg aaccagcagt       480
gacgttggtg gttataactt tgtctcctgg taccaacaac acccaggcaa agcccccaaa       540
ctcatgatct atgatgtcag tgatcggccc tcaggggtgt ctgatcgctt ctccggctcc       600
aagtctggca acacggcctc cctgatcatc tctggcctcc aggctgacga cgaggctgat       660
tattactgca gctcatatgg gagcagcagc actcatgtga ttttcggcgg agggaccaag       720
gtgaccgtcc ta                                                           732
```

<210> SEQ ID NO 66
<211> LENGTH: 703
<212> TYPE: PRT
<213> ORGANISM: artificial sequence
<220> FEATURE:
<223> OTHER INFORMATION: Synthesized

<400> SEQUENCE: 66

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
            275                 280                 285
Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Ser Gly Gly Gly Ser Gln Val Gln Leu Gln
450                 455                 460

Glu Ser Gly Gly Gly Leu Val Lys Pro Gly Gly Ser Leu Arg Leu Ser
465                 470                 475                 480

Cys Ala Ala Ser Gly Phe Thr Phe Ser Ser Tyr Trp Met Ser Trp Val
                485                 490                 495

Arg Gln Ala Pro Gly Lys Gly Leu Glu Trp Val Ala Asn Ile Asn Arg
            500                 505                 510

Asp Gly Ser Ala Ser Tyr Tyr Val Asp Ser Val Lys Gly Arg Phe Thr
        515                 520                 525

Ile Ser Arg Asp Asp Ala Lys Asn Ser Leu Tyr Leu Gln Met Asn Ser
    530                 535                 540

Leu Arg Ala Glu Asp Thr Ala Val Tyr Tyr Cys Ala Arg Asp Arg Gly
545                 550                 555                 560

Val Gly Tyr Phe Asp Leu Trp Gly Arg Gly Thr Leu Val Thr Val Ser
                565                 570                 575

Ser Gly Gly Gly Gly Ser Gly Gly Gly Gly Ser Gly Gly Gly Gly Ser
            580                 585                 590

Gln Ser Ala Leu Thr Gln Pro Ala Ser Val Ser Gly Ser Pro Gly Gln
        595                 600                 605

Ser Ile Thr Ile Ser Cys Thr Gly Thr Ser Ser Asp Val Gly Gly Tyr
    610                 615                 620

Asn Phe Val Ser Trp Tyr Gln Gln His Pro Gly Lys Ala Pro Lys Leu
625                 630                 635                 640

Met Ile Tyr Asp Val Ser Asp Arg Pro Ser Gly Val Ser Asp Arg Phe
                645                 650                 655

Ser Gly Ser Lys Ser Gly Asn Thr Ala Ser Leu Ile Ile Ser Gly Leu
            660                 665                 670

Gln Ala Asp Asp Glu Ala Asp Tyr Tyr Cys Ser Ser Tyr Gly Ser Ser
        675                 680                 685

Ser Thr His Val Ile Phe Gly Gly Gly Thr Lys Val Thr Val Leu
    690                 695                 700
```

<210> SEQ ID NO 67
<211> LENGTH: 119
<212> TYPE: PRT
<213> ORGANISM: artificial sequence
<220> FEATURE:
<223> OTHER INFORMATION: Synthesized

<400> SEQUENCE: 67

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115
```

<210> SEQ ID NO 68
<211> LENGTH: 243
<212> TYPE: PRT
<213> ORGANISM: artificial sequence
<220> FEATURE:
<223> OTHER INFORMATION: Synthesized

<400> SEQUENCE: 68

```
Gln Val Gln Leu Gln Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Ser Gly Gly Gly Gly Ser
        115                 120                 125

Gly Gly Gly Gly Ser Gln Ser Ala Leu Thr Gln Pro Ala Ser Val Ser
130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
```

180                 185                 190
Val Ser Asp Arg Phe Ser Gly Ser Lys Ser Gly Asn Thr Ala Ser Leu
            195                 200                 205

Ile Ile Ser Gly Leu Gln Ala Asp Asp Glu Ala Asp Tyr Tyr Cys Ser
        210                 215                 220

Ser Tyr Gly Ser Ser Ser Thr His Val Ile Phe Gly Gly Gly Thr Lys
225                 230                 235                 240

Val Thr Val

<210> SEQ ID NO 69
<211> LENGTH: 654
<212> TYPE: DNA
<213> ORGANISM: artificial sequence
<220> FEATURE:
<223> OTHER INFORMATION: Synthesized

<400> SEQUENCE: 69
cagtctgccc tgactcagcc tgcctccgtg tctgggtctc ctggacagtc gatcaccatc      60
tcctgcactg gaaccagcag tgacgttggt ggttataact ttgtctcctg gtaccaacaa     120
cacccaggca aagcccccaa actcatgatc tatgatgtca gtgatcggcc ctcaggggtg     180
tctgatcgct tctccggctc caagtctggc aacacggcct ccctgatcat ctctggcctc     240
caggctgacg acgaggctga ttattactgc agctcatatg ggagcagcag cactcatgtg     300
attttcggcg agggaccaa gctgaccgtc ctacgtacgg tggctgcacc atctgtcttc      360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600 acccatcagg gcctgagctc gcccgtcaca aagagcttca caggggaga gtgt            654

<210> SEQ ID NO 70
<211> LENGTH: 333
<212> TYPE: DNA
<213> ORGANISM: artificial sequence
<220> FEATURE:
<223> OTHER INFORMATION: Synthesized

<400> SEQUENCE: 70
cagtctgccc tgactcagcc tgcctccgtg tctgggtctc ctggacagtc gatcaccatc      60
tcctgcactg gaaccagcag tgacgttggt ggttataact ttgtctcctg gtaccaacaa     120
cacccaggca aagcccccaa actcatgatc tatgatgtca gtgatcggcc ctcaggggtg     180
tctgatcgct tctccggctc caagtctggc aacacggcct ccctgatcat ctctggcctc     240
caggctgacg acgaggctga ttattactgc agctcatatg ggagcagcag cactcatgtg     300
attttcggcg agggaccaa gctgaccgtc cta                                    333

<210> SEQ ID NO 71
<211> LENGTH: 218
<212> TYPE: PRT
<213> ORGANISM: artificial sequence
<220> FEATURE:
<223> OTHER INFORMATION: Synthesized

<400> SEQUENCE: 71

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
            35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Thr Lys Leu Thr Val Leu Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 72
<211> LENGTH: 111
<212> TYPE: PRT
<213> ORGANISM: artificial sequence
<220> FEATURE:
<223> OTHER INFORMATION: Synthesized

<400> SEQUENCE: 72

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
            35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
            100                 105                 110

<210> SEQ ID NO 73
<211> LENGTH: 2127
<212> TYPE: DNA
<213> ORGANISM: artificial sequence
<220> FEATURE:
<223> OTHER INFORMATION: Synthesized

<400> SEQUENCE: 73

```
caggtgcagc tgcaggagtc gggggaggc ctggtcaagc ctggagggtc cctgagactc      60
tcctgtgcag cctctggatt cacctttagt agttattgga tgagctgggt ccgccaggct    120
ccagggaagg gctggagtg gtggccaac ataaaccgcg atggaagtgc gagttactat      180
gtggactctg tgaagggccg attcaccatc tccagagacg acgccaagaa ctcactgtat    240
ctgcaaatga acagcctgag agctgaggac acggctgtgt attactgtgc gagagatcgt    300
ggggtgggct acttcgatct ctggggccgt ggcaccctgg tcaccgtctc gagcgctagc    360
accaagggcc catcggtctt ccccctggca cctcctcca agagcacctc tgggggcaca     420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc     600
tgcaacgtga atcacaagcc cagcaacacc aaggtggaca gagagttga gcccaaatct     660
tgtgacaaaa ctcacacatg cccaccgtgc ccagcacctg aactcctggg gggaccgtca    720
gtcttcctct ccccccaaa acccaaggac accctcatga tctcccggac ccctgaggtc     780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga ggagatgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctatagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaaggcggt ggaggatccg gcggtggtgg atcacaagtt   1380
caacttcaac aatctggtgc tgaagttaaa aaacctggtt cttctgttaa agtttcttgt   1440
aaagcctctg gttatacttt tactaattat tatatttatt gggttcgtca agctcctggt   1500
caaggtcttg aatggattgg tggtattaat cctacttctg gtggttctaa ttttaatgaa   1560
aaatttaaaa ctcgtgttac tattactgtt gatgaatcta cgaacactgc ttatatggaa   1620
ctttcttctc ttcgttctga agatactgct ttttattttt gtgcgcgtca aggtctttgg   1680
tttgattctg atggtcgtgg ttttgatttt tggggtcaag gttccactgt tactgtctcg   1740
agcggtggag gcggttcagg cggaggtggt tccggcggtg gcggctccga tattcaaatg   1800
actcaatctc cttcttctct ttctgcttct gttggtgatc gtgttactat tacttgtcgt   1860
tcttctcaaa atattgttca ttctaatggt aatacttatc ttgattggta tcaacaaact   1920
cctggtaaag ctcctaaact tcttatttat aaagtttcta atcgttttc tggtgttcct   1980
tctcgttttt ctggttctgg ttctggtact gattttactt ttactatttc ttctcttcaa   2040
cctgaagata ttgctactta ttattgtttt caatattctc atgttccttg gactttggt   2100
caaggtacta aacttcaaat tactcgt                                       2127
```

<210> SEQ ID NO 74
<211> LENGTH: 354
<212> TYPE: DNA
<213> ORGANISM: artificial sequence
<220> FEATURE:
<223> OTHER INFORMATION: Synthesized

<400> SEQUENCE: 74

```
caggtgcagc tgcaggagtc gggggaggc ctggtcaagc ctggagggtc cctgagactc      60
tcctgtgcag cctctggatt cacctttagt agttattgga tgagctgggt ccgccaggct    120
ccagggaagg gctggagtg gtggccaac ataaaccgcg atggaagtgc gagttactat      180
gtggactctg tgaagggccg attcaccatc tccagacg acgccaagaa ctcactgtat      240
ctgcaaatga acagcctgag agctgaggac acggctgtgt attactgtgc gagagatcgt    300
ggggtgggct acttcgatct ctggggccgt ggcaccctgg tcaccgtctc gagc          354
```

<210> SEQ ID NO 75
<211> LENGTH: 753
<212> TYPE: DNA
<213> ORGANISM: artificial sequence
<220> FEATURE:
<223> OTHER INFORMATION: Synthesized

<400> SEQUENCE: 75

```
caagttcaac ttcaacaatc tggtgctgaa gttaaaaaac ctggttcttc tgttaaagtt     60
tcttgtaaag cctctggtta tactttact aattattata tttattgggt tcgtcaagct    120
cctggtcaag gtcttgaatg gattggtggt attaatccta cttctggtgg ttctaatttt   180
aatgaaaaat ttaaaactcg tgttactatt actgttgatg aatctacgaa cactgcttat   240
atggaacttt cttctcttcg ttctgaagat actgcttttt attttgtgc gcgtcaaggt    300
ctttggtttg attctgatgg tcgtggtttt gattttggg gtcaaggttc cactgttact    360
gtctcgagcg gtggaggcgg ttcaggcgga ggtggttccg gcggtggcgg ctccgatatt   420
caaatgactc aatctccttc ttctctttct gcttctgttg gtgatcgtgt tactattact   480
tgtcgttctt ctcaaaatat tgttcattct aatggtaata cttatcttga ttggtatcaa   540
caaactcctg gtaaagctcc taaacttctt atttataaag tttctaatcg ttttttctggt  600
gttccttctc gtttttctgg ttctggttct ggtactgatt ttactttac tattcttct    660
cttcaacctg aagatattgc tacttatat tgttttcaat attctcatgt tccttggact   720
tttggtcaag gtactaaact tcaaattact cgt                                 753
```

<210> SEQ ID NO 76
<211> LENGTH: 709
<212> TYPE: PRT
<213> ORGANISM: artificial sequence
<220> FEATURE:
<223> OTHER INFORMATION: Synthesized

<400> SEQUENCE: 76

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
```

-continued

```
                85                  90                  95
Ala Arg Asp Arg Gly Val Gly Tyr Phe Asp Leu Trp Gly Arg Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Arg Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445
Gly Gly Gly Gly Ser Gly Gly Gly Ser Gln Val Gln Leu Gln Gln
        450                 455                 460
Ser Gly Ala Glu Val Lys Lys Pro Gly Ser Ser Val Lys Val Ser Cys
465                 470                 475                 480
Lys Ala Ser Gly Tyr Thr Phe Thr Asn Tyr Tyr Ile Tyr Trp Val Arg
                485                 490                 495
Gln Ala Pro Gly Gln Gly Leu Glu Trp Ile Gly Gly Ile Asn Pro Thr
            500                 505                 510
```

```
Ser Gly Gly Ser Asn Phe Asn Glu Lys Phe Lys Thr Arg Val Thr Ile
        515                 520                 525

Thr Val Asp Glu Ser Thr Asn Thr Ala Tyr Met Glu Leu Ser Ser Leu
        530                 535                 540

Arg Ser Glu Asp Thr Ala Phe Tyr Phe Cys Ala Arg Gln Gly Leu Trp
545                 550                 555                 560

Phe Asp Ser Asp Gly Arg Gly Phe Asp Phe Trp Gly Gln Gly Ser Thr
                565                 570                 575

Val Thr Val Ser Ser Gly Gly Gly Ser Gly Gly Gly Ser Gly
            580                 585                 590

Gly Gly Gly Ser Asp Ile Gln Met Thr Gln Ser Pro Ser Ser Leu Ser
        595                 600                 605

Ala Ser Val Gly Asp Arg Val Thr Ile Thr Cys Arg Ser Ser Gln Asn
        610                 615                 620

Ile Val His Ser Asn Gly Asn Thr Tyr Leu Asp Trp Tyr Gln Gln Thr
625                 630                 635                 640

Pro Gly Lys Ala Pro Lys Leu Leu Ile Tyr Lys Val Ser Asn Arg Phe
                645                 650                 655

Ser Gly Val Pro Ser Arg Phe Ser Gly Ser Gly Ser Gly Thr Asp Phe
                660                 665                 670

Thr Phe Thr Ile Ser Ser Leu Gln Pro Glu Asp Ile Ala Thr Tyr Tyr
                675                 680                 685

Cys Phe Gln Tyr Ser His Val Pro Trp Thr Phe Gly Gln Gly Thr Lys
                690                 695                 700

Leu Gln Ile Thr Arg
705

<210> SEQ ID NO 77
<211> LENGTH: 118
<212> TYPE: PRT
<213> ORGANISM: artificial sequence
<220> FEATURE:
<223> OTHER INFORMATION: Synthesized

<400> SEQUENCE: 77

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser
        115

<210> SEQ ID NO 78
<211> LENGTH: 251
<212> TYPE: PRT
<213> ORGANISM: artificial sequence
```

<220> FEATURE:
<223> OTHER INFORMATION: Synthesized

<400> SEQUENCE: 78

Gln Val Gln Leu Gln Gln Ser Gly Ala Glu Val Lys Pro Gly Ser
1               5                   10                  15

Ser Val Lys Val Ser Cys Lys Ala Ser Gly Tyr Thr Phe Thr Asn Tyr
                20                  25                  30

Tyr Ile Tyr Trp Val Arg Gln Ala Pro Gly Gln Gly Leu Glu Trp Ile
            35                  40                  45

Gly Gly Ile Asn Pro Thr Ser Gly Gly Ser Asn Phe Asn Glu Lys Phe
        50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
            100                 105                 110

Trp Gly Gln Gly Ser Thr Val Thr Val Ser Ser Gly Gly Gly Gly Ser
        115                 120                 125

Gly Gly Gly Gly Ser Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ser Ser Gln Asn Ile Val His Ser Asn Gly Asn Thr Tyr Leu
                165                 170                 175

Asp Trp Tyr Gln Gln Thr Pro Gly Lys Ala Pro Lys Leu Leu Ile Tyr
            180                 185                 190

Lys Val Ser Asn Arg Phe Ser Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Phe Gln Tyr Ser His Val Pro Trp Thr
225                 230                 235                 240

Phe Gly Gln Gly Thr Lys Leu Gln Ile Thr Arg
                245                 250

<210> SEQ ID NO 79
<211> LENGTH: 657
<212> TYPE: DNA
<213> ORGANISM: artificial sequence
<220> FEATURE:
<223> OTHER INFORMATION: Synthesized

<400> SEQUENCE: 79
gatattcaaa tgactcaatc tccttcttct ctttctgctt ctgttggtga tcgtgttact      60
attacttgtc gttcttctca aaatattgtt cattctaatg gtaatactta tcttgattgg    120
tatcaacaaa ctcctggtaa agctcctaaa cttcttattt ataaagtttc taatcgtttt    180
tctggtgttc cttctcgttt ttctggttct ggttctggta ctgattttac ttttactatt    240
tcttctcttc aacctgaaga tattgctact tattattgtt tccaatattc tcatgttcct    300
tggacttttg gtcaaggtac taaacttcaa attactcgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg agagtgt       657

<210> SEQ ID NO 80
<211> LENGTH: 336
<212> TYPE: DNA
<213> ORGANISM: artificial sequence
<220> FEATURE:
<223> OTHER INFORMATION: Synthesized

<400> SEQUENCE: 80
gatattcaaa tgactcaatc tccttcttct ctttctgctt ctgttggtga tcgtgttact     60
attacttgtc gttcttctca aaatattgtt cattctaatg gtaatactta tcttgattgg    120
tatcaacaaa ctcctggtaa agctcctaaa cttcttattt ataaagtttc taatcgtttt    180
tctggtgttc cttctcgttt ttctggttct ggttctggta ctgattttac ttttactatt    240
tcttctcttc aacctgaaga tattgctact tattattgtt ttcaatattc tcatgttcct    300
tggacttttg gtcaaggtac taaacttcaa attact                             336

<210> SEQ ID NO 81
<211> LENGTH: 219
<212> TYPE: PRT
<213> ORGANISM: artificial sequence
<220> FEATURE:
<223> OTHER INFORMATION: Synthesized

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 82
<211> LENGTH: 112
<212> TYPE: PRT
<213> ORGANISM: artificial sequence
<220> FEATURE:
<223> OTHER INFORMATION: Synthesized

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110

<210> SEQ ID NO 83
<211> LENGTH: 2121
<212> TYPE: DNA
<213> ORGANISM: artificial sequence
<220> FEATURE:
<223> OTHER INFORMATION: Synthesized

<400> SEQUENCE: 83
caagttcaac ttcaacaatc tggtgctgaa gttaaaaaac ctggttcttc tgttaaagtt      60
tcttgtaaag cctctggtta tactttttact aattattata tttattgggt tcgtcaagct    120
cctggtcaag gtcttgaatg gattggtggt attaatccta cttctggtgg ttctaatttt    180
aatgaaaaat ttaaaactcg tgttactatt actgttgatg aatctacgaa cactgcttat    240 atggaactt cttctcttcg ttctgaagat actgcttttt attttttgtgc gcgtcaaggt    300 ctttggtttg attctgatgg tcgtggtttt gatttttggg gtcaaggttc cactgttact    360
gtctcgagcg ctagcaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca caccaaggt ggacaagaga    660 gttgagccca atcttgtga caaaactcac acatgcccac cgtgcccagc acctgaactc    720 ctgggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
cgggaggaga tgaccaagaa ccaggtcagc ctgacctgcc tggtcaaagg cttctatccc   1140

| | |
|---|---|
| agcgacatcg ccgtggagtg ggagagcaat gggcagccgg agaacaacta caagaccacg | 1200 |
| cctcccgtgc tggactccga cggctccttc ttcctctata gcaagctcac cgtggacaag | 1260 |
| agcaggtggc agcaggggaa cgtcttctca tgctccgtga tgcatgaggc tctgcacaac | 1320 |
| cactacacgc agaagagcct ctccctgtct ccgggtaaag gcggtggagg atccggcggt | 1380 |
| ggtggatcac aggtgcagct gcaggagtcg gggggaggcc tggtcaagcc tggagggtcc | 1440 |
| ctgagactct cctgtgcagc ctctggattc acctttagta gttattggat gagctgggtc | 1500 |
| cgccaggctc cagggaaggg gctggagtgg gtggccaaca taaaccgcga tggaagtgcg | 1560 |
| agttactatg tggactctgt gaagggccga ttcaccatct ccagagacga cgccaagaac | 1620 |
| tcactgtatc tgcaaatgaa cagcctgaga gctgaggaca cggctgtgta ttactgtgcg | 1680 |
| agagatcgtg gggtgggcta cttcgatctc tggggccgtg gcaccctggt caccgtctcg | 1740 |
| agcggtggag gcggttcagg cggaggtggt tccggcggtg cggctcccag gtctgccctg | 1800 |
| actcagcctg cctccgtgtc tgggtctcct ggacagtcga tcaccatctc tgcactgga | 1860 |
| accagcagtg acgttggtgg ttataacttt gtctcctggt accaacaaca cccaggcaaa | 1920 |
| gcccccaaac tcatgatcta tgatgtcagt gatcggccct caggggtgtc tgatcgcttc | 1980 |
| tccggctcca agtctggcaa cacggcctcc ctgatcatct ctggcctcca ggctgacgac | 2040 |
| gaggctgatt attactgcag ctcatatggg agcagcagca ctcatgtgat tttcggcgga | 2100 |
| gggaccaagg tgaccgtcct a | 2121 |

<210> SEQ ID NO 84
<211> LENGTH: 369
<212> TYPE: DNA
<213> ORGANISM: artificial sequence
<220> FEATURE:
<223> OTHER INFORMATION: Synthesized

<400> SEQUENCE: 84

| | |
|---|---|
| caagttcaac ttcaacaatc tggtgctgaa gttaaaaaac tggttcttc tgttaaagtt | 60 |
| tcttgtaaag cctctggtta tacttttact aattattata tttattgggt tcgtcaagct | 120 |
| cctggtcaag gtcttgaatg gattggtggt attaatccta cttctggtgg ttctaatttt | 180 |
| aatgaaaaat ttaaaactcg tgttactatt actgttgatg aatctacgaa cactgcttat | 240 |
| atggaactt cttctcttcg ttctgaagat actgctttt attttgtgc gcgtcaaggt | 300 |
| ctttggtttg attctgatgg tcgtggtttt gattttggg gtcaaggttc cactgttact | 360 |
| gtctcgagc | 369 |

<210> SEQ ID NO 85
<211> LENGTH: 732
<212> TYPE: DNA
<213> ORGANISM: artificial sequence
<220> FEATURE:
<223> OTHER INFORMATION: Synthesized

<400> SEQUENCE: 85

| | |
|---|---|
| caggtgcagc tgcaggagtc ggggggaggc ctggtcaagc ctggagggtc cctgagactc | 60 |
| tcctgtgcag cctctggatt cacctttagt agttattgga tgagctgggt ccgccaggct | 120 |
| ccagggaagg gctggagtg gtggccaac ataaaccgcg atggaagtgc gagttactat | 180 |
| gtggactctg tgaagggccg attcaccatc tccagagacg acgccaagaa ctcactgtat | 240 |
| ctgcaaatga acagcctgag agctgaggac acggctgtgt attactgtgc gagagatcgt | 300 |

-continued

```
ggggtgggct acttcgatct ctggggccgt ggcaccctgg tcaccgtctc gagcggtgga    360
ggcggttcag gcggaggtgg ttccggcggt ggcggctccc agtctgccct gactcagcct    420
gcctccgtgt ctgggtctcc tggacagtcg atcaccatct cctgcactgg aaccagcagt    480
gacgttggtg gttataactt tgtctcctgg taccaacaac acccaggcaa agcccccaaa    540
ctcatgatct atgatgtcag tgatcggccc tcagggggtgt ctgatcgctt ctccggctcc    600
aagtctggca cacggcctc cctgatcatc tctggcctcc aggctgacga cgaggctgat    660
tattactgca gctcatatgg gagcagcagc actcatgtga ttttcggcgg agggaccaag    720
gtgaccgtcc ta                                                         732
```

```
<210> SEQ ID NO 86
<211> LENGTH: 707
<212> TYPE: PRT
<213> ORGANISM: artificial sequence
<220> FEATURE:
<223> OTHER INFORMATION: Synthesized

<400> SEQUENCE: 86
```

| | | | | | | | | | | | | | | |
|---|---|---|---|---|---|---|---|---|---|---|---|---|---|---|
| Gln | Val | Gln | Leu | Gln | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Tyr | Thr | Phe | Thr | Asn | Tyr |
| | | | 20 | | | | | 25 | | | | | 30 | | |
| Tyr | Ile | Tyr | Trp | Val | Arg | Gln | Ala | Pro | Gly | Gln | Gly | Leu | Glu | Trp | Ile |
| | | 35 | | | | | 40 | | | | | 45 | | | |
| Gly | Gly | Ile | Asn | Pro | Thr | Ser | Gly | Gly | Ser | Asn | Phe | Asn | Glu | Lys | Phe |
| | 50 | | | | | 55 | | | | | 60 | | | | |
| Lys | Thr | Arg | Val | Thr | Ile | Thr | Val | Asp | Glu | Ser | Thr | Asn | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Phe | Tyr | Phe | Cys |
| | | | | 85 | | | | | 90 | | | | | 95 | |
| Ala | Arg | Gln | Gly | Leu | Trp | Phe | Asp | Ser | Asp | Gly | Arg | Gly | Phe | Asp | Phe |
| | | | 100 | | | | | 105 | | | | | 110 | | |
| Trp | Gly | Gln | Gly | Ser | Thr | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Ser | Ser | Lys | Ser | Thr | Ser | Gly | Gly |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | 195 | | | | | 200 | | | | | 205 | | | |
| Asn | His | Lys | Pro | Ser | Asn | Thr | Lys | Val | Asp | Lys | Arg | Val | Glu | Pro | Lys |
| | 210 | | | | | 215 | | | | | 220 | | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | 275 | | | | | 280 | | | | | 285 | | | |

```
Glu Val His Asn Ala Lys Thr Lys Pro Arg Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                    325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys Gly Gly Gly Gly Ser Gly Gly Gly Gly Ser Gln
450                 455                 460

Val Gln Leu Gln Glu Ser Gly Gly Gly Leu Val Lys Pro Gly Gly Ser
465                 470                 475                 480

Leu Arg Leu Ser Cys Ala Ala Ser Gly Phe Thr Phe Ser Ser Tyr Trp
                485                 490                 495

Met Ser Trp Val Arg Gln Ala Pro Gly Lys Gly Leu Glu Trp Val Ala
                500                 505                 510

Asn Ile Asn Arg Asp Gly Ser Ala Ser Tyr Tyr Val Asp Ser Val Lys
            515                 520                 525

Gly Arg Phe Thr Ile Ser Arg Asp Asp Ala Lys Asn Ser Leu Tyr Leu
            530                 535                 540

Gln Met Asn Ser Leu Arg Ala Glu Asp Thr Ala Val Tyr Tyr Cys Ala
545                 550                 555                 560

Arg Asp Arg Gly Val Gly Tyr Phe Asp Leu Trp Gly Arg Gly Thr Leu
                565                 570                 575

Val Thr Val Ser Ser Gly Gly Gly Ser Gly Gly Gly Gly Ser Gly
                580                 585                 590

Gly Gly Gly Ser Gln Ser Ala Leu Thr Gln Pro Ala Ser Val Ser Gly
            595                 600                 605

Ser Pro Gly Gln Ser Ile Thr Ile Ser Cys Thr Gly Thr Ser Ser Asp
610                 615                 620

Val Gly Gly Tyr Asn Phe Val Ser Trp Tyr Gln Gln His Pro Gly Lys
625                 630                 635                 640

Ala Pro Lys Leu Met Ile Tyr Asp Val Ser Asp Arg Pro Ser Gly Val
                645                 650                 655

Ser Asp Arg Phe Ser Gly Ser Lys Ser Gly Asn Thr Ala Ser Leu Ile
                660                 665                 670

Ile Ser Gly Leu Gln Ala Asp Asp Glu Ala Asp Tyr Tyr Cys Ser Ser
            675                 680                 685

Tyr Gly Ser Ser Ser Thr His Val Ile Phe Gly Gly Gly Thr Lys Val
            690                 695                 700
```

Thr Val Leu
705

<210> SEQ ID NO 87
<211> LENGTH: 123
<212> TYPE: PRT
<213> ORGANISM: artificial sequence
<220> FEATURE:
<223> OTHER INFORMATION: Synthesized

<400> SEQUENCE: 87

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
            100                 105                 110

Trp Gly Gln Gly Ser Thr Val Thr Val Ser Ser
        115                 120

<210> SEQ ID NO 88
<211> LENGTH: 244
<212> TYPE: PRT
<213> ORGANISM: artificial sequence
<220> FEATURE:
<223> OTHER INFORMATION: Synthesized

<400> SEQUENCE: 88

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
                180                 185                 190

Val Ser Asp Arg Phe Ser Gly Ser Lys Ser Gly Asn Thr Ala Ser Leu
            195                 200                 205

Ile Ile Ser Gly Leu Gln Ala Asp Asp Glu Ala Asp Tyr Tyr Cys Ser
210                 215                 220

Ser Tyr Gly Ser Ser Ser Thr His Val Ile Phe Gly Gly Gly Thr Lys
225                 230                 235                 240

Val Thr Val Leu

<210> SEQ ID NO 89
<211> LENGTH: 657
<212> TYPE: DNA
<213> ORGANISM: artificial sequence
<220> FEATURE:
<223> OTHER INFORMATION: Synthesized

<400> SEQUENCE: 89
gatattcaaa tgactcaatc tccttcttct ctttctgctt ctgttggtga tcgtgttact     60
attacttgtc gttcttctca aaatattgtt cattctaatg gtaatactta tcttgattgg    120
tatcaacaaa ctcctggtaa agctcctaaa cttcttattt ataaagtttc taatcgtttt    180
tctggtgttc cttctcgttt ttctggttct ggttctggta ctgatttac ttttactatt     240 tcttctcttc aacctgaaga tattgctact tattattgtt ttcaatattc tcatgttcct    300 tggactttg gtcaaggtac taaacttcaa attactcgta cggtggctgc accatctgtc     360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657

<210> SEQ ID NO 90
<211> LENGTH: 336
<212> TYPE: DNA
<213> ORGANISM: artificial sequence
<220> FEATURE:
<223> OTHER INFORMATION: Synthesized

<400> SEQUENCE: 90
gatattcaaa tgactcaatc tccttcttct ctttctgctt ctgttggtga tcgtgttact     60
attacttgtc gttcttctca aaatattgtt cattctaatg gtaatactta tcttgattgg    120
tatcaacaaa ctcctggtaa agctcctaaa cttcttattt ataaagtttc taatcgtttt    180
tctggtgttc cttctcgttt ttctggttct ggttctggta ctgatttac ttttactatt     240 tcttctcttc aacctgaaga tattgctact tattattgtt ttcaatattc tcatgttcct    300 tggactttg gtcaaggtac taaacttcaa attact                              336

<210> SEQ ID NO 91
<211> LENGTH: 336
<212> TYPE: DNA
<213> ORGANISM: artificial sequence
<220> FEATURE:
<223> OTHER INFORMATION: Synthesized

<400> SEQUENCE: 91

```
gacatccaga tgacccagtc cccttccagc ctgtccgctt ccgtgggcga cagggtgacc      60
atcacctgca ggtcctccca gaacatcgtg cactccaacg caataccta cctggactgg     120 taccagcaga cccccggcaa ggcccctaag ctgctgatct acaaggtgag caaccggttc     180
agcggcgtgc cttcccggtt ttccggatcc ggctccggca cagacttcac cttcaccatc    240
tcctccctgc aacccgagga catcgccacc tactactgct tccagtactc ccatgtgccc    300
tggaccttcg gcagggcac caagctgcag atcacc                              336
```

`<210>` SEQ ID NO 92
`<211>` LENGTH: 218
`<212>` TYPE: PRT
`<213>` ORGANISM: artificial sequence
`<220>` FEATURE:
`<223>` OTHER INFORMATION: Synthesized

`<400>` SEQUENCE: 92

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asp Arg Pro Ser Gly Val Ser Asp Arg Phe
    50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

`<210>` SEQ ID NO 93
`<211>` LENGTH: 111
`<212>` TYPE: PRT
`<213>` ORGANISM: artificial sequence
`<220>` FEATURE:
`<223>` OTHER INFORMATION: Synthesized

`<400>` SEQUENCE: 93

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30
```

Asn Phe Val Ser Trp Tyr Gln Gln His Pro Gly Lys Ala Pro Lys Leu
            35                  40                  45

Met Ile Tyr Asp Val Ser Asp Arg Pro Ser Gly Val Ser Asp Arg Phe
        50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Leu Thr Val Leu
                100                 105                 110

<210> SEQ ID NO 94
<211> LENGTH: 2118
<212> TYPE: DNA
<213> ORGANISM: artificial sequence
<220> FEATURE:
<223> OTHER INFORMATION: Synthesized

<400> SEQUENCE: 94
caggtgcagc tgcagcagag cggcgccgag gtgaagaagc ccggcagcag cgtgaaggtg      60
agctgcaagg ccagcggcta caccttcacc aactactaca tctactgggt gcggcaggcc     120
cccggccagg gcctggagtg gatcggcggc atcaacccca ccagcggcgg cagcaacttc     180
aacgagaagt tcaagacccg ggtgaccatc accgccgacg agagcagcac caccgcctac     240
atggagctga gcagcctgcg gagcgaggac accgccttct acttctgcac ccggcagggc     300
ctgtggttcg acgccgacgg ccggggcttc gacttctggg gccagggcac caccgtgacc     360
gtgagcagcg ctagcaccaa gggcccatcg gtcttccccc tggcaccctc ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca acaccaaggt ggacaagaga     660
gttgagccca aatcttgtga caaaactcac acatgcccac cgtgcccagc acctgaactc     720
ctggggggac cgtcagtctt cctcttcccc ccaaaaccca aggacaccct catgatctcc     780
cggacccctg aggtcacatg cgtggtggtg gacgtgagcc acgaagaccc tgaggtcaag     840
ttcaactggt acgtggacgg cgtggaggtg cataatgcca agacaaagcc gcgggaggag     900
cagtacaaca gcacgtaccg tgtggtcagc gtcctcaccg tcctgcacca ggactggctg     960
aatggcaagg agtacaagtg caaggtctcc aacaaagccc tcccagcccc catcgagaaa    1020
accatctcca aagccaaagg gcagccccga gaaccacagg tgtacaccct gcccccatcc    1080
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctata gcaagctcac cgtggacaag    1260
agcaggtggc agcaggggaa cgtcttctca tgctccgtga tgcatgaggc tctgcacaac    1320
cactacacgc agaagagcct ctccctgtct ccgggtggcg gtgagggtc cggcggtggt    1380 ggatcacagg tgcaattgca ggagtcgggg ggaggcctgg tcaagcctgg agggtccctg    1440
agactctcct gtgcagcctc tggattcacc tttagtagtt attggatgag ctgggtccgc    1500
caggctccag ggaaggggct ggagtgggtg gccaacataa accgcgatgg aagtgcgagt    1560
tactatgtgg actctgtgaa gggccgattc accatctcca gagacgacgc caagaactca    1620

```
ctgtatctgc aaatgaacag cctgagagct gaggacacgg ctgtgtatta ctgtgcgaga    1680
gatcgtgggg tgggctactt cgatctctgg ggccgtggca ccctggtcac cgtctcgagc    1740
ggtggaggcg gttcaggcgg aggtggttcc ggcggtggcg gctcccagtc tgccctgact    1800
cagcctgcct ccgtgtctgg gtctcctgga cagtcgatca ccatctcctg cactggaacc    1860
agcagtgacg ttggtggtta aactttgtc tcctggtacc aacaacaccc aggcaaagcc    1920
cccaaactca tgatctatga tgtcagtgat cggccctcag gggtgtctga tcgcttctcc    1980
ggctccaagt ctggcaacac ggcctccctg atcatctctg gcctccaggc tgacgacgag    2040
gctgattatt actgcagctc atatgggagc agcagcactc atgtgatttt cggcggaggg    2100
accaaggtga ccgtccta                                                  2118

<210> SEQ ID NO 95
<211> LENGTH: 369
<212> TYPE: DNA
<213> ORGANISM: artificial sequence
<220> FEATURE:
<223> OTHER INFORMATION: Synthesized

<400> SEQUENCE: 95
caggtgcagc tgcagcagag cggcgccgag gtgaagaagc ccggcagcag cgtgaaggtg     60
agctgcaagg ccagcggcta caccttcacc aactactaca tctactgggt gcggcaggcc    120
cccggccagg gcctggagtg gatcggcggc atcaacccca ccagcggcgg cagcaacttc    180
aacgagaagt tcaagacccg ggtgaccatc accgccgacg agagcagcac caccgcctac    240
atggagctga gcagcctgcg gagcgaggac accgccttct acttctgcac ccggcagggc    300
ctgtggttcg acagcgacgg ccggggcttc gacttctggg gccagggcac caccgtgacc    360
gtgagcagc                                                            369

<210> SEQ ID NO 96
<211> LENGTH: 369
<212> TYPE: DNA
<213> ORGANISM: artificial sequence
<220> FEATURE:
<223> OTHER INFORMATION: Synthesized

<400> SEQUENCE: 96
caggtgcagc tgcagcaatc cggcgccgag gtgaagaagc ctggctccag cgtgaaggtg     60
tcctgcaagg cctccggcta caccttcacc aactactaca tctactgggt gaggcaggct    120
cctggccagg gactggagtg gatcggcggc atcaacccta cctccggcgg ctccaacttc    180
aacgagaagt tcaagacccg ggtgaccatc accgccgatg agagctccac caccgcctac    240
atggagctgt cctccctgag gtccgaggac accgcctttt acttctgcac caggcaggga    300
ctgtggttcg actccgacgg ccggggcttc gattttggg gccagggcac cacagtgacc    360
gtgtcctcc                                                            369

<210> SEQ ID NO 97
<211> LENGTH: 732
<212> TYPE: DNA
<213> ORGANISM: artificial sequence
<220> FEATURE:
<223> OTHER INFORMATION: Synthesized

<400> SEQUENCE: 97
caggtgcaat tgcaggagtc gggggggaggc ctggtcaagc ctggagggtc cctgagactc     60
```

```
tcctgtgcag cctctggatt cacctttagt agttattgga tgagctgggt ccgccaggct    120
ccagggaagg ggctggagtg ggtggccaac ataaaccgcg atggaagtgc gagttactat    180
gtggactctg tgaagggccg attcaccatc tccagagacg acgccaagaa ctcactgtat    240
ctgcaaatga acagcctgag agctgaggac acggctgtgt attactgtgc gagagatcgt    300
ggggtgggct acttcgatct ctggggccgt ggcaccctgg tcaccgtctc gagcggtgga    360
ggcggttcag gcggaggtgg ttccggcggt ggcggctccc agtctgccct gactcagcct    420
gcctccgtgt ctgggtctcc tggacagtcg atcaccatct cctgcactgg aaccagcagt    480
gacgttggtg gttataactt tgtctcctgg taccaacaac cccaggcaa agcccccaaa    540 ctcatgatct atgatgtcag tgatcggccc tcagggtgt ctgatcgctt ctccggctcc    600
aagtctggca cacggcctc cctgatcatc tctggcctcc aggctgacga cgaggctgat    660
tattactgca gctcatatgg gagcagcagc actcatgtga ttttcggcgg agggaccaag    720
gtgaccgtcc ta                                                        732
```

<210> SEQ ID NO 98
<211> LENGTH: 706
<212> TYPE: PRT
<213> ORGANISM: artificial sequence
<220> FEATURE:
<223> OTHER INFORMATION: Synthesized

<400> SEQUENCE: 98

```
Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240
```

-continued

Leu Gly Gly Pro Ser Val Phe Leu Phe Pro Pro Lys Pro Lys Asp Thr
                    245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Gly Gly Gly Ser Gly Gly Gly Ser Gln Val
    450                 455                 460
Gln Leu Gln Glu Ser Gly Gly Gly Leu Val Lys Pro Gly Gly Ser Leu
465                 470                 475                 480
Arg Leu Ser Cys Ala Ala Ser Gly Phe Thr Phe Ser Ser Tyr Trp Met
                485                 490                 495
Ser Trp Val Arg Gln Ala Pro Gly Lys Gly Leu Glu Trp Val Ala Asn
            500                 505                 510
Ile Asn Arg Asp Gly Ser Ala Ser Tyr Tyr Val Asp Ser Val Lys Gly
        515                 520                 525
Arg Phe Thr Ile Ser Arg Asp Asp Ala Lys Asn Ser Leu Tyr Leu Gln
    530                 535                 540
Met Asn Ser Leu Arg Ala Glu Asp Thr Ala Val Tyr Tyr Cys Ala Arg
545                 550                 555                 560
Asp Arg Gly Val Gly Tyr Phe Asp Leu Trp Gly Arg Gly Thr Leu Val
                565                 570                 575
Thr Val Ser Ser Gly Gly Gly Ser Gly Gly Gly Ser Gly Gly
            580                 585                 590
Gly Gly Ser Gln Ser Ala Leu Thr Gln Pro Ala Ser Val Ser Gly Ser
        595                 600                 605
Pro Gly Gln Ser Ile Thr Ile Ser Cys Thr Gly Thr Ser Ser Asp Val
    610                 615                 620
Gly Gly Tyr Asn Phe Val Ser Trp Tyr Gln Gln His Pro Gly Lys Ala
625                 630                 635                 640
Pro Lys Leu Met Ile Tyr Asp Val Ser Asp Arg Pro Ser Gly Val Ser
                645                 650                 655
Asp Arg Phe Ser Gly Ser Lys Ser Gly Asn Thr Ala Ser Leu Ile Ile

```
                     660                 665                 670
Ser Gly Leu Gln Ala Asp Asp Glu Ala Asp Tyr Tyr Cys Ser Ser Tyr
            675                 680                 685

Gly Ser Ser Ser Thr His Val Ile Phe Gly Gly Gly Thr Lys Val Thr
            690                 695                 700

Val Leu
705

<210> SEQ ID NO 99
<211> LENGTH: 123
<212> TYPE: PRT
<213> ORGANISM: artificial sequence
<220> FEATURE:
<223> OTHER INFORMATION: Synthesized

<400> SEQUENCE: 99

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser
        115                 120

<210> SEQ ID NO 100
<211> LENGTH: 244
<212> TYPE: PRT
<213> ORGANISM: artificial sequence
<220> FEATURE:
<223> OTHER INFORMATION: Synthesized

<400> SEQUENCE: 100

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Ser Gly Gly Gly Ser
        115                 120                 125
```

Gly Gly Gly Gly Ser Gln Ser Ala Leu Thr Gln Pro Ala Ser Val Ser
            130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu

<210> SEQ ID NO 101
<211> LENGTH: 654
<212> TYPE: DNA
<213> ORGANISM: artificial sequence
<220> FEATURE:
<223> OTHER INFORMATION: Synthesized

<400> SEQUENCE: 101
cagtctgccc tgactcagcc tgcctccgtg tctgggtctc ctggacagtc gatcaccatc     60
tcctgcactg gaaccagcag tgacgttggt ggttataact ttgtctcctg gtaccaacaa    120
cacccaggca aagcccccaa actcatgatc tatgatgtca gtgatcggcc ctcaggggtg    180
tctgatcgct tctccggctc caagtctggc aacacggcct ccctgatcat ctctggcctc    240
caggctgacg acgaggctga ttattactgc agctcatatg ggagcagcag cactcatgtg    300
attttcggcg gagggaccaa gctgaccgtc ctacgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttca caggggaga gtgt          654

<210> SEQ ID NO 102
<211> LENGTH: 333
<212> TYPE: DNA
<213> ORGANISM: artificial sequence
<220> FEATURE:
<223> OTHER INFORMATION: Synthesized

<400> SEQUENCE: 102
cagtctgccc tgactcagcc tgcctccgtg tctgggtctc ctggacagtc gatcaccatc     60
tcctgcactg gaaccagcag tgacgttggt ggttataact ttgtctcctg gtaccaacaa    120
cacccaggca aagcccccaa actcatgatc tatgatgtca gtgatcggcc ctcaggggtg    180
tctgatcgct tctccggctc caagtctggc aacacggcct ccctgatcat ctctggcctc    240
caggctgacg acgaggctga ttattactgc agctcatatg ggagcagcag cactcatgtg    300
attttcggcg gagggaccaa gctgaccgtc cta                                 333

<210> SEQ ID NO 103

<211> LENGTH: 218
<212> TYPE: PRT
<213> ORGANISM: artificial sequence
<220> FEATURE:
<223> OTHER INFORMATION: Synthesized

<400> SEQUENCE: 103

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Phe Val Ser Trp Tyr Gln Gln His Pro Gly Lys Ala Pro Lys Leu
        35                  40                  45
Met Ile Tyr Asp Val Ser Asp Arg Pro Ser Gly Val Ser Asp Arg Phe
    50                  55                  60
Ser Gly Ser Lys Ser Gly Asn Thr Ala Ser Leu Ile Ile Ser Gly Leu
65                  70                  75                  80
Gln Ala Asp Asp Glu Ala Asp Tyr Tyr Cys Ser Ser Tyr Gly Ser Ser
                85                  90                  95
Ser Thr His Val Ile Phe Gly Gly Gly Thr Lys Leu Thr Val Leu Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 104
<211> LENGTH: 111
<212> TYPE: PRT
<213> ORGANISM: artificial sequence
<220> FEATURE:
<223> OTHER INFORMATION: Synthesized

<400> SEQUENCE: 104

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Phe Val Ser Trp Tyr Gln Gln His Pro Gly Lys Ala Pro Lys Leu
        35                  40                  45
Met Ile Tyr Asp Val Ser Asp Arg Pro Ser Gly Val Ser Asp Arg Phe
    50                  55                  60
Ser Gly Ser Lys Ser Gly Asn Thr Ala Ser Leu Ile Ile Ser Gly Leu
65                  70                  75                  80
Gln Ala Asp Asp Glu Ala Asp Tyr Tyr Cys Ser Ser Tyr Gly Ser Ser
                85                  90                  95
Ser Thr His Val Ile Phe Gly Gly Gly Thr Lys Leu Thr Val Leu
```

<210> SEQ ID NO 105
<211> LENGTH: 2100
<212> TYPE: DNA
<213> ORGANISM: artificial sequence
<220> FEATURE:
<223> OTHER INFORMATION: Synthesized

<400> SEQUENCE: 105

```
caggtgcagc tgcaggagtc gggggaggc ctggtcaagc ctggagggtc cctgagactc      60
tcctgtgcag cctctggatt cacctttagt agttattgga tgagctgggt ccgccaggct     120
ccagggaagg ggctggagtg ggtggccaac ataaaccgcg atggaagtgc gagttactat     180
gtggactctg tgaagggccg attcaccatc tccagagacg acgccaagaa ctcactgtat     240
ctgcaaatga acagcctgag agctgaggac acggctgtgt attactgtgc gagagatcgt     300
ggggtgggct acttcgatct ctggggccgt ggcaccctgg tcaccgtctc gagcgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc      600
tgcaacgtga atcacaagcc cagcaacacc aaggtggaca gagagttga gcccaaatct      660
tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtga aggtgcataa tgccaagaca agccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccggga ggagatgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaaggcggt ggaggatccg gcggtggtgg atcacaggtg    1380
cagctgaagc agtcaggacc tggcctagtg cagccctcac agagcctgtc catcacctgc    1440
acagtctctg gtttctcatt aactaactat ggtgtacact gggttcgcca gtctccagga    1500
aagggtctgg agtggctggg agtgatatgg agtggtggaa acacagacta taatacacct    1560
ttcacatcca gactgagcat caacaaggac aattccaaga gccaagtttt ctttaaaatg    1620
aacagtctgc aatctaatga cacagccata tattactgtg ccagagccct cacctactat    1680
gattacgagt ttgcttactg gggccaaggg actctggtca ctgtctctag cggtggaggc    1740
ggttcaggcg gaggtggttc cggcggtggc ggctccgaca tcttgctgac tcagtctcca    1800
gtcatcctgt ctgtgagtcc aggagaaaga gtcagtttct cctgcagggc cagtcagagt    1860
attggcacaa acatacactg gtatcagcaa agaacaaatg gttctccaag gcttctcata    1920
aagtatgctt ctgagtctat ctctgggatt ccttccaggt ttagtggcag tggatcaggg    1980
acagatttta ctcttagcat caacagtgtg gagtctgaag atattgcaga ttattactgt    2040
```

```
caacaaaata ataactggcc aaccacgttc ggtgctggga ccaagctgga gctgaaacgt    2100
```

<210> SEQ ID NO 106
<211> LENGTH: 354
<212> TYPE: DNA
<213> ORGANISM: artificial sequence
<220> FEATURE:
<223> OTHER INFORMATION: Synthesized

<400> SEQUENCE: 106

```
caggtgcagc tgcaggagtc gggggagggc ctggtcaagc ctggagggtc cctgagactc      60
tcctgtgcag cctctggatt cacctttagt agttattgga tgagctgggt ccgccaggct     120
ccagggaagg ggctggagtg ggtggccaac ataaaccgcg atggaagtgc gagttactat     180
gtggactctg tgaagggccg attcaccatc tccagagacg acgccaagaa ctcactgtat     240
ctgcaaatga acagcctgag agctgaggac acggctgtgt attactgtgc gagagatcgt     300
ggggtgggct acttcgatct ctggggccgt ggcaccctgg tcaccgtctc gagc           354
```

<210> SEQ ID NO 107
<211> LENGTH: 726
<212> TYPE: DNA
<213> ORGANISM: artificial sequence
<220> FEATURE:
<223> OTHER INFORMATION: Synthesized

<400> SEQUENCE: 107

```
caggtgcagc tgaagcagtc aggacctggc ctagtgcagc cctcacagag cctgtccatc      60
acctgcacag tctctggttt ctcattaact aactatggtg tacactgggt tcgccagtct     120
ccaggaaagg gtctggagtg gctgggagtg atatggagtg gtggaaacac agactataat     180
acacctttca catccagact gagcatcaac aaggacaatt ccaagagcca gttttctttt     240
aaaatgaaca gtctgcaatc taatgacaca gccatatatt actgtgccag agccctcacc     300
tactatgatt acgagtttgc ttactggggc caagggactc tggtcactgt ctctagcggt     360
ggaggcggtt caggcggagg tggttccggc ggtggcggct ccgacatctt gctgactcag     420
tctccagtca tcctgtctgt gagtccagga gaaagagtca gtttctcctg cagggccagt     480
cagagtattg gcacaaacat acactggtat cagcaaagaa caaatggttc tccaaggctt     540
ctcataaagt atgcttctga gtctatctct gggattcctt ccaggtttag tggcagtgga     600
tcagggacag attttactct tagcatcaac agtgtggagt ctgaagatat tgcagattat     660
tactgtcaac aaaataataa ctggccaacc acgttcggtg ctgggaccaa gctggagctg     720
aaacgt                                                               726
```

<210> SEQ ID NO 108
<211> LENGTH: 700
<212> TYPE: PRT
<213> ORGANISM: artificial sequence
<220> FEATURE:
<223> OTHER INFORMATION: Synthesized

<400> SEQUENCE: 108

```
Gln Val Gln Leu Gln Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45
```

Ala Asn Ile Asn Arg Asp Gly Ser Ala Ser Tyr Tyr Val Asp Ser Val
            50                  55                  60
Lys Gly Arg Phe Thr Ile Ser Arg Asp Asp Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Arg Gly Val Gly Tyr Phe Asp Leu Trp Gly Arg Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Arg Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445
Gly Gly Gly Gly Ser Gly Gly Gly Ser Gln Val Gln Leu Lys Gln
450                 455                 460

```
Ser Gly Pro Gly Leu Val Gln Pro Ser Gln Ser Leu Ser Ile Thr Cys
465                 470                 475                 480

Thr Val Ser Gly Phe Ser Leu Thr Asn Tyr Gly Val His Trp Val Arg
            485                 490                 495

Gln Ser Pro Gly Lys Gly Leu Glu Trp Leu Gly Val Ile Trp Ser Gly
        500                 505                 510

Gly Asn Thr Asp Tyr Asn Thr Pro Phe Thr Ser Arg Leu Ser Ile Asn
    515                 520                 525

Lys Asp Asn Ser Lys Ser Gln Val Phe Phe Lys Met Asn Ser Leu Gln
530                 535                 540

Ser Asn Asp Thr Ala Ile Tyr Tyr Cys Ala Arg Ala Leu Thr Tyr Tyr
545                 550                 555                 560

Asp Tyr Glu Phe Ala Tyr Trp Gly Gln Gly Thr Leu Val Thr Val Ser
            565                 570                 575

Ser Gly Gly Gly Gly Ser Gly Gly Gly Gly Ser Gly Gly Gly Gly Ser
        580                 585                 590

Asp Ile Leu Leu Thr Gln Ser Pro Val Ile Leu Ser Val Ser Pro Gly
    595                 600                 605

Glu Arg Val Ser Phe Ser Cys Arg Ala Ser Gln Ser Ile Gly Thr Asn
610                 615                 620

Ile His Trp Tyr Gln Gln Arg Thr Asn Gly Ser Pro Arg Leu Leu Ile
625                 630                 635                 640

Lys Tyr Ala Ser Glu Ser Ile Ser Gly Ile Pro Ser Arg Phe Ser Gly
            645                 650                 655

Ser Gly Ser Gly Thr Asp Phe Thr Leu Ser Ile Asn Ser Val Glu Ser
        660                 665                 670

Glu Asp Ile Ala Asp Tyr Tyr Cys Gln Gln Asn Asn Asn Trp Pro Thr
    675                 680                 685

Thr Phe Gly Ala Gly Thr Lys Leu Glu Leu Lys Arg
            690                 695                 700

<210> SEQ ID NO 109
<211> LENGTH: 118
<212> TYPE: PRT
<213> ORGANISM: artificial sequence
<220> FEATURE:
<223> OTHER INFORMATION: Synthesized

<400> SEQUENCE: 109

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Gly Val Gly Tyr Phe Asp Leu Trp Gly Arg Gly Thr
        100                 105                 110

Leu Val Thr Val Ser Ser
            115
```

<210> SEQ ID NO 110
<211> LENGTH: 242
<212> TYPE: PRT
<213> ORGANISM: artificial sequence
<220> FEATURE:
<223> OTHER INFORMATION: Synthesized

<400> SEQUENCE: 110

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Leu Leu Thr Gln Ser Pro Val Ile
    130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Ser Pro Arg Leu Leu Ile Lys Tyr Ala Ser Glu Ser Ile Ser Gly Ile
            180                 185                 190

Pro Ser Arg Phe Ser Gly Ser Gly Ser Gly Thr Asp Phe Thr Leu Ser
        195                 200                 205

Ile Asn Ser Val Glu Ser Glu Asp Ile Ala Asp Tyr Tyr Cys Gln Gln
    210                 215                 220

Asn Asn Asn Trp Pro Thr Thr Phe Gly Ala Gly Thr Lys Leu Glu Leu
225                 230                 235                 240

Lys Arg
```

<210> SEQ ID NO 111
<211> LENGTH: 642
<212> TYPE: DNA
<213> ORGANISM: artificial sequence
<220> FEATURE:
<223> OTHER INFORMATION: Synthesized

<400> SEQUENCE: 111

```
gacatcttgc tgactcagtc tccagtcatc ctgtctgtga gtccaggaga aagagtcagt    60
ttctcctgca gggccagtca gagtattggc acaaacatac actggtatca gcaagaaca   120 aatggttctc caaggcttct cataaagtat gcttctgagt ctatctctgg gattccttcc   180
aggtttagtg gcagtggatc aggacagat tttactctta gcatcaacag tgtggagtct   240
gaagatattg cagattatta ctgtcaacaa aataataact ggccaaccac gttcggtgct   300
gggaccaagc tggagctgaa acgtacggtg gctgcaccat ctgtcttcat cttcccgcca   360
```

```
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac agggagagt gt                        642
```

<210> SEQ ID NO 112
<211> LENGTH: 321
<212> TYPE: DNA
<213> ORGANISM: artificial sequence
<220> FEATURE:
<223> OTHER INFORMATION: Synthesized

<400> SEQUENCE: 112

```
gacatcttgc tgactcagtc tccagtcatc ctgtctgtga gtccaggaga aagagtcagt     60
ttctcctgca gggccagtca gagtattggc acaaacatac actggtatca gcaaagaaca    120
aatggttctc caaggcttct cataaagtat gcttctgagt ctatctctgg gattccttcc    180
aggtttagtg gcagtggatc agggacagat tttactctta gcatcaacag tgtggagtct    240
gaagatattg cagattatta ctgtcaacaa aataataact ggccaaccac gttcggtgct    300
gggaccaagc tggagctgaa a                                              321
```

<210> SEQ ID NO 113
<211> LENGTH: 214
<212> TYPE: PRT
<213> ORGANISM: artificial sequence
<220> FEATURE:
<223> OTHER INFORMATION: Synthesized

<400> SEQUENCE: 113

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser

Phe Asn Arg Gly Glu Cys
    210

<210> SEQ ID NO 114
<211> LENGTH: 107
<212> TYPE: PRT
<213> ORGANISM: artificial sequence
<220> FEATURE:
<223> OTHER INFORMATION: Synthesized

<400> SEQUENCE: 114

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 115
<211> LENGTH: 2109
<212> TYPE: DNA
<213> ORGANISM: artificial sequence
<220> FEATURE:
<223> OTHER INFORMATION: Synthesized

<400> SEQUENCE: 115
caggtgcagc tgaagcagtc aggacctggc ctagtgcagc cctcacagag cctgtccatc      60
acctgcacag tctctggttt ctcattaact aactatggtg tacactgggt tcgccagtct     120
ccaggaaagg gtctggagtg gctgggagtg atatggagtg gtggaaacac agactataat     180
acacctttca catccagact gagcatcaac aaggacaatt ccaagagcca agttttcttt     240
aaaatgaaca gtctgcaatc taatgacaca gccatatatt actgtgccag agccctcacc     300
tactatgatt acgagtttgc ttactggggc caagggactc tggtcactgt ctctagcgct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020

```
gccaaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctatagc aagctcaccg tggacaagag caggtggcag    1260
caggggaacg tcttctcatg ctccgtgatg catgaggctc tgcacaacca ctacacgcag    1320
aagagcctct ccctgtctcc gggtaaaggc ggtggaggat ccggcggtgg tggatcacag    1380
gtgcagctgc aggagtcggg gggaggcctg gtcaagcctg agggtccct gagactctcc    1440 tgtgcagcct ctggattcac ctttagtagt tattggatga gctgggtccg ccaggctcca    1500 gggaagggc tggagtgggt ggccaacata aaccgcgatg gaagtgcgag ttactatgtg    1560
gactctgtga agggccgatt caccatctcc agagacgacg ccaagaactc actgtatctg    1620
caaatgaaca gcctgagagc tgaggacacg gctgtgtatt actgtgcgag agatcgtggg    1680
gtgggctact cgatctctg gggccgtggc accctggtca ccgtctcgag cggtggaggc    1740
ggttcaggcg gaggtggttc cggcggtggc ggctcccagt ctgccctgac tcagcctgcc    1800
tccgtgtctg gtctcctgg acagtcgatc accatctcct gcactggaac cagcagtgac    1860
gttggtggtt ataactttgt ctcctggtac caacaacacc caggcaaagc ccccaaactc    1920
atgatctatg atgtcagtga tcggccctca ggggtgtctg atcgcttctc cggctccaag    1980
tctggcaaca cggcctccct gatcatctct ggcctccagg ctgacgacga ggctgattat    2040
tactgcagct catatgggag cagcagcact catgtgattt tcggcggagg gaccaaggtg    2100
accgtcctg                                                            2109

<210> SEQ ID NO 116
<211> LENGTH: 357
<212> TYPE: DNA
<213> ORGANISM: artificial sequence
<220> FEATURE:
<223> OTHER INFORMATION: Synthesized

<400> SEQUENCE: 116
caggtgcagc tgaagcagtc aggacctggc ctagtgcagc cctcacagag cctgtccatc     60
acctgcacag tctctggttt ctcattaact aactatggtg tacactgggt tcgccagtct    120
ccaggaaagg gtctggagtg gctgggagtg atatggagtg gtggaaacac agactataat    180
acacctttca catccagact gagcatcaac aaggacaatt ccaagagcca gttttctttt    240
aaaatgaaca gtctgcaatc taatgacaca gccatatatt actgtgccag agccctcacc    300
tactatgatt acgagtttgc ttactggggc caagggactc tggtcactgt ctctagc       357

<210> SEQ ID NO 117
<211> LENGTH: 732
<212> TYPE: DNA
<213> ORGANISM: artificial sequence
<220> FEATURE:
<223> OTHER INFORMATION: Synthesized

<400> SEQUENCE: 117
caggtgcagc tgcaggagtc ggggggaggc ctggtcaagc ctggagggtc cctgagactc     60
tcctgtgcag cctctggatt cacctttagt agttattgga tgagctgggt ccgccaggct    120
ccagggaagg gctggagtg gtggccaac ataaaccgcg atggaagtgc gagttactat    180
gtggactctg tgaagggccg attcaccatc tccagagacg acgccaagaa ctcactgtat    240
```

```
ctgcaaatga acagcctgag agctgaggac acggctgtgt attactgtgc gagagatcgt    300
ggggtgggct acttcgatct ctggggccgt ggcaccctgg tcaccgtctc gagcggtgga    360
ggcggttcag gcggaggtgg ttccggcggt ggcggctccc agtctgccct gactcagcct    420
gcctccgtgt ctgggtctcc tggacagtcg atcaccatct cctgcactgg aaccagcagt    480
gacgttggtg gttataactt tgtctcctgg taccaacaac acccaggcaa agcccccaaa    540
ctcatgatct atgatgtcag tgatcggccc tcaggggtgt ctgatcgctt ctccggctcc    600
aagtctggca acacggcctc cctgatcatc tctggcctcc aggctgacga cgaggctgat    660
tattactgca gctcatatgg gagcagcagc actcatgtga ttttcggcgg agggaccaag    720
gtgaccgtcc ta                                                        732
```

<210> SEQ ID NO 118
<211> LENGTH: 703
<212> TYPE: PRT
<213> ORGANISM: artificial sequence
<220> FEATURE:
<223> OTHER INFORMATION: Synthesized

<400> SEQUENCE: 118

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Gly Gly Gly Ser Gly Gly Gly Ser Gln Val Gln Leu Gln
450                 455                 460
Glu Ser Gly Gly Gly Leu Val Lys Pro Gly Gly Ser Leu Arg Leu Ser
465                 470                 475                 480
Cys Ala Ala Ser Gly Phe Thr Phe Ser Ser Tyr Trp Met Ser Trp Val
                485                 490                 495
Arg Gln Ala Pro Gly Lys Gly Leu Glu Trp Val Ala Asn Ile Asn Arg
            500                 505                 510
Asp Gly Ser Ala Ser Tyr Tyr Val Asp Ser Val Lys Gly Arg Phe Thr
        515                 520                 525
Ile Ser Arg Asp Asp Ala Lys Asn Ser Leu Tyr Leu Gln Met Asn Ser
530                 535                 540
Leu Arg Ala Glu Asp Thr Ala Val Tyr Tyr Cys Ala Arg Asp Arg Gly
545                 550                 555                 560
Val Gly Tyr Phe Asp Leu Trp Gly Arg Gly Thr Leu Val Thr Val Ser
                565                 570                 575
Ser Gly Gly Gly Gly Ser Gly Gly Gly Gly Ser Gly Gly Gly Gly Ser
            580                 585                 590
Gln Ser Ala Leu Thr Gln Pro Ala Ser Val Ser Gly Ser Pro Gly Gln
        595                 600                 605
Ser Ile Thr Ile Ser Cys Thr Gly Thr Ser Ser Asp Val Gly Gly Tyr
610                 615                 620
Asn Phe Val Ser Trp Tyr Gln Gln His Pro Gly Lys Ala Pro Lys Leu
625                 630                 635                 640
Met Ile Tyr Asp Val Ser Asp Arg Pro Ser Gly Val Ser Asp Arg Phe
                645                 650                 655
Ser Gly Ser Lys Ser Gly Asn Thr Ala Ser Leu Ile Ile Ser Gly Leu
            660                 665                 670
Gln Ala Asp Asp Glu Ala Asp Tyr Tyr Cys Ser Ser Tyr Gly Ser Ser
        675                 680                 685
Ser Thr His Val Ile Phe Gly Gly Gly Thr Lys Val Thr Val Leu
```

690                 695                 700

<210> SEQ ID NO 119
<211> LENGTH: 119
<212> TYPE: PRT
<213> ORGANISM: artificial sequence
<220> FEATURE:
<223> OTHER INFORMATION: Synthesized

<400> SEQUENCE: 119

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 120
<211> LENGTH: 244
<212> TYPE: PRT
<213> ORGANISM: artificial sequence
<220> FEATURE:
<223> OTHER INFORMATION: Synthesized

<400> SEQUENCE: 120

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
    130                 135                 140

Gly Ser Pro Gly Gln Ser Ile Thr Ile Ser Cys Thr Gly Thr Ser Ser
145                 150                 155                 160

Asp Val Gly Gly Tyr Asn Phe Val Ser Trp Tyr Gln Gln His Pro Gly
                165                 170                 175

Lys Ala Pro Lys Leu Met Ile Tyr Asp Val Ser Asp Arg Pro Ser Gly
            180                 185                 190

Val Ser Asp Arg Phe Ser Gly Ser Lys Ser Gly Asn Thr Ala Ser Leu
        195                 200                 205

Ile Ile Ser Gly Leu Gln Ala Asp Asp Glu Ala Asp Tyr Tyr Cys Ser
    210                 215                 220

Ser Tyr Gly Ser Ser Ser Thr His Val Ile Phe Gly Gly Gly Thr Lys
225                 230                 235                 240

Val Thr Val Leu

<210> SEQ ID NO 121
<211> LENGTH: 642
<212> TYPE: DNA
<213> ORGANISM: artificial sequence
<220> FEATURE:
<223> OTHER INFORMATION: Synthesized

<400> SEQUENCE: 121
gacatcttgc tgactcagtc tccagtcatc ctgtctgtga gtccaggaga aagagtcagt       60
ttctcctgca gggccagtca gagtattggc acaaacatac actggtatca gcaaagaaca      120
aatggttctc caaggcttct cataaagtat gcttctgagt ctatctctgg gattccttcc      180
aggtttagtg gcagtggatc agggacagat tttactctta gcatcaacag tgtggagtct      240
gaagatattg cagattatta ctgtcaacaa aataataact ggccaaccac gttcggtgct      300
gggaccaagc tggagctgaa acgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                         642

<210> SEQ ID NO 122
<211> LENGTH: 321
<212> TYPE: DNA
<213> ORGANISM: artificial sequence
<220> FEATURE:
<223> OTHER INFORMATION: Synthesized

<400> SEQUENCE: 122
gacatcttgc tgactcagtc tccagtcatc ctgtctgtga gtccaggaga aagagtcagt       60
ttctcctgca gggccagtca gagtattggc acaaacatac actggtatca gcaaagaaca      120
aatggttctc caaggcttct cataaagtat gcttctgagt ctatctctgg gattccttcc      180
aggtttagtg gcagtggatc agggacagat tttactctta gcatcaacag tgtggagtct      240
gaagatattg cagattatta ctgtcaacaa aataataact ggccaaccac gttcggtgct      300
gggaccaagc tggagctgaa a                                                 321

<210> SEQ ID NO 123
<211> LENGTH: 214
<212> TYPE: PRT
<213> ORGANISM: artificial sequence
<220> FEATURE:
<223> OTHER INFORMATION: Synthesized

<400> SEQUENCE: 123

Asp Ile Leu Leu Thr Gln Ser Pro Val Ile Leu Ser Val Ser Pro Gly

```
            1               5                  10                 15
          Glu Arg Val Ser Phe Ser Cys Arg Ala Ser Gln Ser Ile Gly Thr Asn
                           20                  25                 30

Ile His Trp Tyr Gln Gln Arg Thr Asn Gly Ser Pro Arg Leu Leu Ile
                       35                  40                  45

Lys Tyr Ala Ser Glu Ser Ile Ser Gly Ile Pro Ser Arg Phe Ser Gly
                   50                  55                  60

Ser Gly Ser Gly Thr Asp Phe Thr Leu Ser Ile Asn Ser Val Glu Ser
          65                  70                  75                  80

Glu Asp Ile Ala Asp Tyr Tyr Cys Gln Gln Asn Asn Asn Trp Pro Thr
                           85                  90                  95

Thr Phe Gly Ala Gly Thr Lys Leu Glu Leu Lys Arg Thr Val Ala Ala
                          100                 105                 110

Pro Ser Val Phe Ile Phe Pro Pro Ser Asp Glu Gln Leu Lys Ser Gly
                          115                 120                 125

Thr Ala Ser Val Val Cys Leu Leu Asn Asn Phe Tyr Pro Arg Glu Ala
                          130                 135                 140

Lys Val Gln Trp Lys Val Asp Asn Ala Leu Gln Ser Gly Asn Ser Gln
          145                 150                 155                 160

Glu Ser Val Thr Glu Gln Asp Ser Lys Asp Ser Thr Tyr Ser Leu Ser
                          165                 170                 175

Ser Thr Leu Thr Leu Ser Lys Ala Asp Tyr Glu Lys His Lys Val Tyr
                          180                 185                 190

Ala Cys Glu Val Thr His Gln Gly Leu Ser Ser Pro Val Thr Lys Ser
                          195                 200                 205

Phe Asn Arg Gly Glu Cys
                          210

<210> SEQ ID NO 124
<211> LENGTH: 107
<212> TYPE: PRT
<213> ORGANISM: artificial sequence
<220> FEATURE:
<223> OTHER INFORMATION: Synthesized

<400> SEQUENCE: 124

Asp Ile Leu Leu Thr Gln Ser Pro Val Ile Leu Ser Val Ser Pro Gly
          1               5                  10                  15

Glu Arg Val Ser Phe Ser Cys Arg Ala Ser Gln Ser Ile Gly Thr Asn
                           20                  25                 30

Ile His Trp Tyr Gln Gln Arg Thr Asn Gly Ser Pro Arg Leu Leu Ile
                       35                  40                  45

Lys Tyr Ala Ser Glu Ser Ile Ser Gly Ile Pro Ser Arg Phe Ser Gly
                   50                  55                  60

Ser Gly Ser Gly Thr Asp Phe Thr Leu Ser Ile Asn Ser Val Glu Ser
          65                  70                  75                  80

Glu Asp Ile Ala Asp Tyr Tyr Cys Gln Gln Asn Asn Asn Trp Pro Thr
                           85                  90                  95

Thr Phe Gly Ala Gly Thr Lys Leu Glu Leu Lys
                          100                 105

<210> SEQ ID NO 125
<211> LENGTH: 1344
<212> TYPE: DNA
<213> ORGANISM: artificial sequence
<220> FEATURE:
<223> OTHER INFORMATION: Synthesized
```

<400> SEQUENCE: 125

```
caggtgcagc tgaagcagtc aggacctggc ctagtgcagc cctcacagag cctgtccatc      60
acctgcacag tctctggttt ctcattaact aactatggtg tacactgggt tcgccagtct     120
ccaggaaagg gtctggagtg gctgggagtg atatggagtg gtggaaacac agactataat     180
acacctttca catccagact gagcatcaac aaggacaatt ccaagagcca agttttcttt     240
aaaatgaaca gtctgcaatc taatgacaca gccatatatt actgtgccag agccctcacc     300
tactatgatt acgagtttgc ttactggggc caagggactc tggtcactgt ctctagcgct     360
agcaccaagg gcccatcggt cttccccctg gcacctcct ccaagagcac ctctgggggc       420
acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaactcct ggggggaccg     720
tcagtcttcc tcttccccc aaaacccaag gacaccctca tgatctcccg gacccctgag       780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagcccca tcgagaaaac catctccaaa     1020
gccaaagggc agccccgaga accacaggtg tacaccctgc ccccatcccg ggatgagctg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctatagc aagctcaccg tggacaagag caggtggcag     1260
caggggaacg tcttctcatg ctccgtgatg catgaggctc tgcacaacca ctacacgcag     1320
aagagcctct ccctgtctcc gggt                                           1344
```

<210> SEQ ID NO 126
<211> LENGTH: 357
<212> TYPE: DNA
<213> ORGANISM: artificial sequence
<220> FEATURE:
<223> OTHER INFORMATION: Synthesized

<400> SEQUENCE: 126

```
caggtgcagc tgaagcagtc aggacctggc ctagtgcagc cctcacagag cctgtccatc      60
acctgcacag tctctggttt ctcattaact aactatggtg tacactgggt tcgccagtct     120
ccaggaaagg gtctggagtg gctgggagtg atatggagtg gtggaaacac agactataat     180
acacctttca catccagact gagcatcaac aaggacaatt ccaagagcca agttttcttt     240
aaaatgaaca gtctgcaatc taatgacaca gccatatatt actgtgccag agccctcacc     300
tactatgatt acgagtttgc ttactggggc caagggactc tggtcactgt ctctagc         357
```

<210> SEQ ID NO 127
<211> LENGTH: 448
<212> TYPE: PRT
<213> ORGANISM: artificial sequence
<220> FEATURE:
<223> OTHER INFORMATION: Synthesized

```
<400> SEQUENCE: 127

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
          420                 425                 430

Ala Leu His Asn His Tyr Thr Gln Lys Ser Leu Ser Leu Ser Pro Gly
          435                 440                 445

<210> SEQ ID NO 128
<211> LENGTH: 119
<212> TYPE: PRT
<213> ORGANISM: artificial sequence
<220> FEATURE:
<223> OTHER INFORMATION: Synthesized

<400> SEQUENCE: 128

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 129
<211> LENGTH: 642
<212> TYPE: DNA
<213> ORGANISM: artificial sequence
<220> FEATURE:
<223> OTHER INFORMATION: Synthesized

<400> SEQUENCE: 129
gacatcttgc tgactcagtc tccagtcatc ctgtctgtga gtccaggaga aagagtcagt    60
ttctcctgca gggccagtca gagtattggc acaaacatac actggtatca gcaagaaca   120 aatggttctc caaggcttct cataaagtat gcttctgagt ctatctctgg gattccttcc   180
aggtttagtg gcagtggatc aggacagat tttactctta gcatcaacag tgtggagtct   240
gaagatattg cagattatta ctgtcaacaa aataataact ggccaaccac gttcggtgct   300
gggaccaagc tggagctgaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac agggagagt gt                       642

<210> SEQ ID NO 130
<211> LENGTH: 321
<212> TYPE: DNA
<213> ORGANISM: artificial sequence
<220> FEATURE:

<223> OTHER INFORMATION: Synthesized

<400> SEQUENCE: 130

```
gacatcttgc tgactcagtc tccagtcatc ctgtctgtga gtccaggaga aagagtcagt      60
ttctcctgca gggccagtca gagtattggc acaaacatac actggtatca gcaaagaaca     120
aatggttctc caaggcttct cataaagtat gcttctgagt ctatctctgg gattccttcc     180
aggtttagtg gcagtggatc agggacagat tttactctta gcatcaacag tgtggagtct     240
gaagatattg cagattatta ctgtcaacaa aataataact ggccaaccac gttcggtgct     300
gggaccaagc tggagctgaa a                                               321
```

<210> SEQ ID NO 131
<211> LENGTH: 214
<212> TYPE: PRT
<213> ORGANISM: artificial sequence
<220> FEATURE:
<223> OTHER INFORMATION: Synthesized

<400> SEQUENCE: 131

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 132
<211> LENGTH: 107
<212> TYPE: PRT
<213> ORGANISM: artificial sequence
<220> FEATURE:
<223> OTHER INFORMATION: Synthesized

<400> SEQUENCE: 132

Asp Ile Leu Leu Thr Gln Ser Pro Val Ile Leu Ser Val Ser Pro Gly

```
              1               5              10              15
            Glu Arg Val Ser Phe Ser Cys Arg Ala Ser Gln Ser Ile Gly Thr Asn
                             20                  25                  30

Ile His Trp Tyr Gln Gln Arg Thr Asn Gly Ser Pro Arg Leu Leu Ile
                     35                  40                  45

Lys Tyr Ala Ser Glu Ser Ile Ser Gly Ile Pro Ser Arg Phe Ser Gly
                     50                  55                  60

Ser Gly Ser Gly Thr Asp Phe Thr Leu Ser Ile Asn Ser Val Glu Ser
             65                  70                  75                  80

Glu Asp Ile Ala Asp Tyr Tyr Cys Gln Gln Asn Asn Asn Trp Pro Thr
                             85                  90                  95

Thr Phe Gly Ala Gly Thr Lys Leu Glu Leu Lys
                            100                 105
```

<210> SEQ ID NO 133
<211> LENGTH: 2106
<212> TYPE: DNA
<213> ORGANISM: artificial sequence
<220> FEATURE:
<223> OTHER INFORMATION: Synthesized

<400> SEQUENCE: 133

```
caggtgcagc tgaagcagtc aggacctggc ctagtgcagc cctcacagag cctgtccatc      60
acctgcacag tctctggttt ctcattaact aactatggtg tacactgggt tcgccagtct     120
ccaggaaagg gtctggagtg gctgggagtg atatggagtg gtggaaacac agactataat     180
acacctttca catccagact gagcatcaac aaggacaatt ccaagagcca agttttcttt     240
aaaatgaaca gtctgcaatc taatgacaca gccatatatt actgtgccag agccctcacc     300
tactatgatt acgagtttgc ttactggggc caagggactc tggtcactgt ctctagcgct     360
agcaccaagg gcccatcggt cttccccctg gcaccctcct ccaagagcac ctctggggc      420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctatagc aagctcaccg tggacaagag caggtggcag    1260
caggggaacg tcttctcatg ctccgtgatg catgaggctc tgcacaacca ctacacgcag    1320
aagagcctct ccctgtctcc gggtggcggt ggagggtccg gcggtggtgg atcacaggtg    1380
caattgcagg agtcgggggg aggcctggtc aagcctggag ggtccctgag actctcctgt    1440
gcagcctctg gattcacctt tagtagttat tggatgagct gggtccgcca ggctccaggg    1500
```

| | |
|---|---|
| aaggggctgg agtgggtggc aacataaac cgcgatggaa gtgcgagtta ctatgtggac | 1560 |
| tctgtgaagg gccgattcac catctccaga gacgacgcca agaactcact gtatctgcaa | 1620 |
| atgaacagcc tgagagctga ggacacggct gtgtattact gtgcgagaga tcgtggggtg | 1680 |
| ggctacttcg atctctgggg ccgtggcacc ctggtcaccg tctcgagcgg tggaggcggt | 1740 |
| tcaggcggag gtggttccgg cggtggcggc tcccagtctg ccctgactca gcctgcctcc | 1800 |
| gtgtctgggt ctcctggaca gtcgatcacc atctcctgca ctggaaccag cagtgacgtt | 1860 |
| ggtggttata actttgtctc ctggtaccaa caacccag gcaaagcccc caaactcatg | 1920 |
| atctatgatg tcagtgatcg gccctcaggg gtgtctgatc gcttctccgg ctccaagtct | 1980 |
| ggcaacacgg cctccctgat catctctggc ctccaggctg acgacgaggc tgattattac | 2040 |
| tgcagctcat atgggagcag cagcactcat gtgattttcg gcggagggac caaggtgacc | 2100 |
| gtccta | 2106 |

<210> SEQ ID NO 134
<211> LENGTH: 357
<212> TYPE: DNA
<213> ORGANISM: artificial sequence
<220> FEATURE:
<223> OTHER INFORMATION: Synthesized

<400> SEQUENCE: 134

| | |
|---|---|
| caggtgcagc tgaagcagtc aggacctggc ctagtgcagc cctcacagag cctgtccatc | 60 |
| acctgcacag tctctggttt ctcattaact aactatggtg tacactgggt tcgccagtct | 120 |
| ccaggaaagg gtctggagtg gctgggagtg atatggagtg gtggaaacac agactataat | 180 |
| acacctttca catccagact gagcatcaac aaggacaatt ccaagagcca agttttcttt | 240 |
| aaaatgaaca gtctgcaatc taatgacaca gccatatatt actgtgccag agccctcacc | 300 |
| tactatgatt acgagtttgc ttactggggc caagggactc tggtcactgt ctctagc | 357 |

<210> SEQ ID NO 135
<211> LENGTH: 732
<212> TYPE: DNA
<213> ORGANISM: artificial sequence
<220> FEATURE:
<223> OTHER INFORMATION: Synthesized

<400> SEQUENCE: 135

| | |
|---|---|
| caggtgcagc tgcaggagtc gggggagggc ctggtcaagc ctggagggtc cctgagactc | 60 |
| tcctgtgcag cctctggatt cacctttagt agttattgga tgagctgggt ccgccaggct | 120 |
| ccagggaagg ggctggagtg ggtggccaac ataaaccgcg atggaagtgc gagttactat | 180 |
| gtggactctg tgaagggccg attcaccatc tccagagacg acgccaagaa ctcactgtat | 240 |
| ctgcaaatga acagcctgag agctgaggac acggctgtgt attactgtgc gagagatcgt | 300 |
| ggggtgggct acttcgatct ctggggccgt ggcaccctgg tcaccgtctc gagcggtgga | 360 |
| ggcggttcag gcggaggtgg ttccggcggt ggcggctccc agtctgccct gactcagcct | 420 |
| gcctccgtgt ctgggtctcc tggacagtcg atcaccatct cctgcactgg aaccagcagt | 480 |
| gacgttggtg gttataactt tgtctcctgg taccaacaac ccaggcaa agccccaaa | 540 |
| ctcatgatct atgatgtcag tgatcggccc tcaggggtgt ctgatcgctt ctccggctcc | 600 |
| aagtctggca acacggcctc cctgatcatc tctggcctcc aggctgacga cgaggctgat | 660 |
| tattactgca gctcatatgg gagcagcagc actcatgtga ttttcggcgg agggaccaag | 720 |

-continued

```
gtgaccgtcc ta                                                        732
```

<210> SEQ ID NO 136
<211> LENGTH: 702
<212> TYPE: PRT
<213> ORGANISM: artificial sequence
<220> FEATURE:
<223> OTHER INFORMATION: Synthesized

<400> SEQUENCE: 136

```
Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Asn Tyr
             20                  25                  30

Gly Val His Trp Val Arg Gln Ser Pro Gly Lys Gly Leu Glu Trp Leu
         35                  40                  45

Gly Val Ile Trp Ser Gly Gly Asn Thr Asp Tyr Asn Thr Pro Phe Thr
     50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
                    355                 360                 365
Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Gly Ser Gly Gly Gly Ser Gln Val Gln Leu Gln Glu
    450                 455                 460

Ser Gly Gly Gly Leu Val Lys Pro Gly Gly Ser Leu Arg Leu Ser Cys
465                 470                 475                 480

Ala Ala Ser Gly Phe Thr Phe Ser Ser Tyr Trp Met Ser Trp Val Arg
                485                 490                 495

Gln Ala Pro Gly Lys Gly Leu Glu Trp Val Ala Asn Ile Asn Arg Asp
            500                 505                 510

Gly Ser Ala Ser Tyr Tyr Val Asp Ser Val Lys Gly Arg Phe Thr Ile
        515                 520                 525

Ser Arg Asp Asp Ala Lys Asn Ser Leu Tyr Leu Gln Met Asn Ser Leu
530                 535                 540

Arg Ala Glu Asp Thr Ala Val Tyr Tyr Cys Ala Arg Asp Arg Gly Val
545                 550                 555                 560

Gly Tyr Phe Asp Leu Trp Gly Arg Gly Thr Leu Val Thr Val Ser Ser
                565                 570                 575

Gly Gly Gly Gly Ser Gly Gly Gly Ser Gly Gly Gly Gly Ser Gln
            580                 585                 590

Ser Ala Leu Thr Gln Pro Ala Ser Val Ser Gly Ser Pro Gly Gln Ser
        595                 600                 605

Ile Thr Ile Ser Cys Thr Gly Thr Ser Ser Asp Val Gly Gly Tyr Asn
    610                 615                 620

Phe Val Ser Trp Tyr Gln Gln His Pro Gly Lys Ala Pro Lys Leu Met
625                 630                 635                 640

Ile Tyr Asp Val Ser Asp Arg Pro Ser Gly Val Ser Asp Arg Phe Ser
                645                 650                 655

Gly Ser Lys Ser Gly Asn Thr Ala Ser Leu Ile Ile Ser Gly Leu Gln
            660                 665                 670

Ala Asp Asp Glu Ala Asp Tyr Tyr Cys Ser Ser Tyr Gly Ser Ser Ser
        675                 680                 685

Thr His Val Ile Phe Gly Gly Gly Thr Lys Val Thr Val Leu
    690                 695                 700

<210> SEQ ID NO 137
<211> LENGTH: 119
<212> TYPE: PRT
<213> ORGANISM: artificial sequence
<220> FEATURE:
<223> OTHER INFORMATION: Synthesized

<400> SEQUENCE: 137

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
```

```
                    20                  25                  30
Gly Val His Trp Val Arg Gln Ser Pro Gly Lys Gly Leu Glu Trp Leu
                35                  40                  45
Gly Val Ile Trp Ser Gly Gly Asn Thr Asp Tyr Asn Thr Pro Phe Thr
            50                  55                  60
Ser Arg Leu Ser Ile Asn Lys Asp Asn Ser Lys Ser Gln Val Phe Phe
65                  70                  75                  80
Lys Met Asn Ser Leu Gln Ser Asn Asp Thr Ala Ile Tyr Tyr Cys Ala
                85                  90                  95
Arg Ala Leu Thr Tyr Tyr Asp Tyr Glu Phe Ala Tyr Trp Gly Gln Gly
                100                 105                 110
Thr Leu Val Thr Val Ser Ser
            115

<210> SEQ ID NO 138
<211> LENGTH: 244
<212> TYPE: PRT
<213> ORGANISM: artificial sequence
<220> FEATURE:
<223> OTHER INFORMATION: Synthesized

<400> SEQUENCE: 138

Gln Val Gln Leu Gln Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
                20                  25                  30
Trp Met Ser Trp Val Arg Gln Ala Pro Gly Lys Gly Leu Glu Trp Val
                35                  40                  45
Ala Asn Ile Asn Arg Asp Gly Ser Ala Ser Tyr Tyr Val Asp Ser Val
            50                  55                  60
Lys Gly Arg Phe Thr Ile Ser Arg Asp Asp Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Arg Gly Val Gly Tyr Phe Asp Leu Trp Gly Arg Gly Thr
                100                 105                 110
Leu Val Thr Val Ser Ser Gly Gly Gly Gly Ser Gly Gly Gly Gly Ser
            115                 120                 125
Gly Gly Gly Gly Ser Gln Ser Ala Leu Thr Gln Pro Ala Ser Val Ser
        130                 135                 140
Gly Ser Pro Gly Gln Ser Ile Thr Ile Ser Cys Thr Gly Thr Ser Ser
145                 150                 155                 160
Asp Val Gly Gly Tyr Asn Phe Val Ser Trp Tyr Gln Gln His Pro Gly
                165                 170                 175
Lys Ala Pro Lys Leu Met Ile Tyr Asp Val Ser Asp Arg Pro Ser Gly
                180                 185                 190
Val Ser Asp Arg Phe Ser Gly Ser Lys Ser Gly Asn Thr Ala Ser Leu
            195                 200                 205
Ile Ile Ser Gly Leu Gln Ala Asp Asp Glu Ala Asp Tyr Tyr Cys Ser
        210                 215                 220
Ser Tyr Gly Ser Ser Ser Thr His Val Ile Phe Gly Gly Gly Thr Lys
225                 230                 235                 240
Val Thr Val Leu
```

BISPECIFIC TETRAVALENT ANTIBODIES AND METHODS OF MAKING AND USING THEREOF

CROSS REFERENCE TO RELATED PATENT APPLICATIONS

This application is a national stage application of International Application No. PCT/US15/66951, filed Dec. 19, 2015, titled "bispecific tetravalent antibodies and methods of making and using thereof," which claims priority over U.S. Provisional Application No. 62/095,348, filed Dec. 22, 2014, titled "BISPECIFIC ANTIBODIES," which is hereby incorporated by reference in its entirety.

SEQUENCE LISTING

The Sequence Listing associated with this application is provided in text format in lieu of a paper copy, and is hereby incorporated by reference into the specification. The name of the text file containing the Sequence Listing is Sequence Listing_ST25_0003PCT2.txt. The text file is about 227 KB, was created on Dec. 18, 2015, and is being submitted electronically via EFS-Web.

TECHNICAL FIELD

The present disclosure generally relates to the technical field of antibody therapeutic agents, and more particularly relates to bispecific tetravalent antibodies against two different members of EGFR family.

BACKGROUND

Overexpression and/or deregulation of members of the ErbB/HER receptor family such as EGFR, HER2, HER3, HER4 have been shown to play an important role in tumorigenesis in cancers. Mutation and amplification of EGFR or HER2 produce aberrant growth signal which activates downstream signaling pathway contributing to tumorigenesis. Therapeutic antibodies and small-molecule inhibitors directed against EGFR and HER2 have been approved for use in the treatment of cancer (Arteaga et al., *Nature Reviews Clinical Oncology* 9 16-32, January 2012). Monoclonal antibodies against members of EGFR family such as EGFR and HER2, have demonstrated good clinical responses in colon cancer (Price et al., *The Lancet Oncology* 15(6), Pages 569-579, May 2014), squamous cell carcinoma of head and neck (Cohen, *Cancer Treatment Reviews* 40 (2014) 567-577), breast and gastric cancers (Arteaga et al., *Nature Reviews Clinical Oncology* 9 16-32, January 2012). Several therapeutic anti-EGFR antibodies, including cetuximab, panitumumab and nimotuzumab are approved therapeutics for several cancers including metastatic colorectal cancer, head and neck squamous cell carcinoma and glioma (Price and Cohen, *Curr Treat Options Oncol.* 2012 March; 13(1): 35-46; Bode et al., *Expert Opin Biol Ther.* 2012 December; 12 (12):1649-59). Unfortunately, many tumors that initially respond to these therapeutic agents eventually progress due to an acquired resistance to the agents (Jackman et al. *J Clin Oncol* 2010; 28:357-60). Therefore, there exists a need for better cancer therapeutics.

SUMMARY

The disclosure provides bispecific tetravalent antibodies. The bispecific tetravalent antibodies may include an immunoglobulin G (IgG) moiety with two heavy chains and two light chains, and two scFv moieties being covalently connected to either C or N terminals of the heavy or light chains. The IgG moiety may have a binding specificity to a first member of EGFR family. The scFv moiety may have a binding specificity to a second member of the EGFR family. The IgG moiety and two scFv moieties are covalently connected to be functional as a bispecific tetravalent antibody. The objectives and advantages of the disclosure will become apparent from the following detailed description of preferred embodiments thereof in connection with the accompanying drawings.

BRIEF DESCRIPTION OF THE DRAWINGS

Preferred embodiments according to the present disclosure will now be described with reference to the FIGs, in which like reference numerals denote like elements.

DETAILED DESCRIPTION

Figure 1:
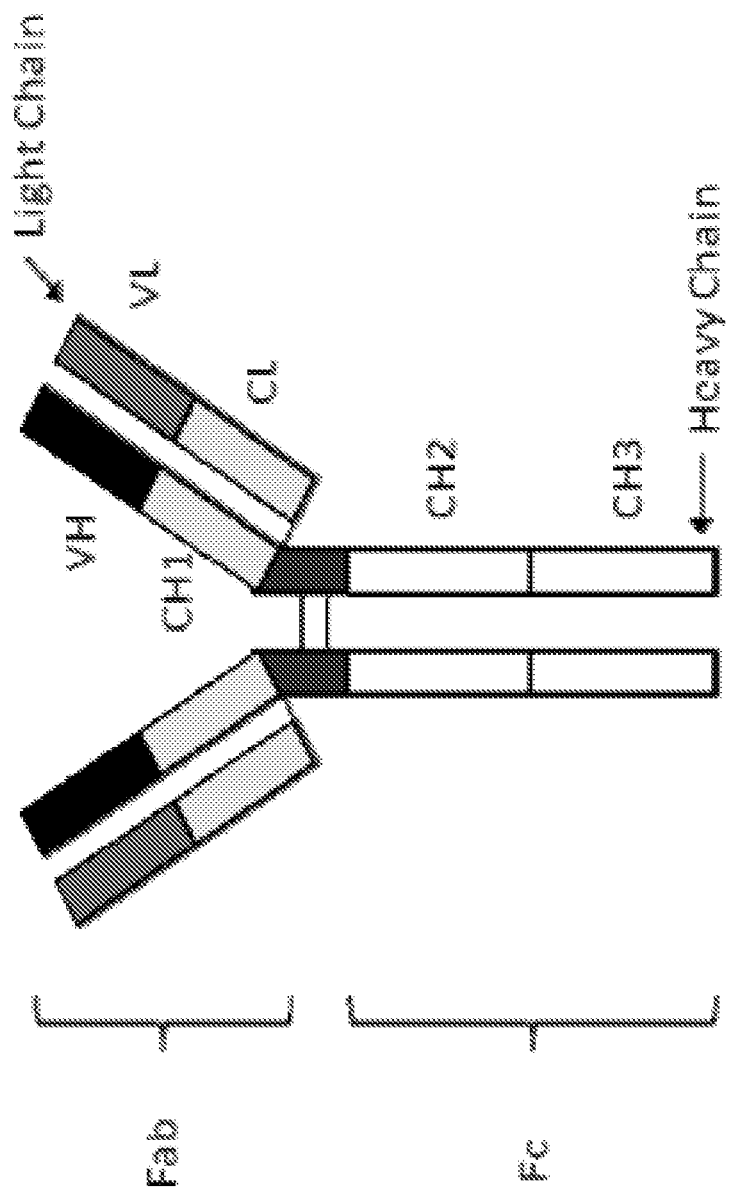
FIG. 1 is a diagram showing the domain structures of an example bivalent monospecific immunoglobulin G (IgG) antibody.

The present disclosure This disclosure provides bispecific tetravalent antibodies with superior therapeutic properties or efficacies over the currently known anti-EGFR antibodies. In one embodiment, the antibodies target two members of EGFR family including, without limitation, EFFR and HER3. The bispecific tetravalent antibodies may inhibit both EGFR and HER3 mediated signaling simultaneously therefore overcome resistance in EGFR inhibitor or monoclonal antibody treatment.

It must be noted that as used herein and in the appended claims, the singular forms "a", "and", and "the" in Throughout this specification and claims, the word "comprise," or variations such as "comprises" or "comprising," will be understood to imply the inclusion of a stated integer or group of integers but not the exclusion of any other integer or group of integers include plural referents unless the context clearly dictates otherwise.

"Antibody fragments" comprise a portion of an intact antibody, preferably the antigen-binding or variable region of the intact antibody. Examples of antibody fragments include Fv, Fab, Fab', F(ab')2, Fab'-SH; diabodies; linear antibodies (see U.S. Pat. No. 5,641,870, Example 2; Zapata et al., Protein Eng. 8(10): 1057-1062 (1995)); single-chain antibody molecules (e.g. scFv). While in the present description, and throughout the specification, reference is made to antibodies and various properties of antibodies, the same disclosure also applies to functional antibody fragments, e.g. dual action Fab fragments.

In one aspect, the bispecific tetravalent antibodies may include an immunoglobulin G (IgG) moiety with two heavy chains and two light chains, and two scFv moieties being covalently connected to either C or N terminals of the heavy or light chains. The IgG moiety may have a binding specificity to a first member of EGFR family. The scFv moiety may have a binding specificity to a second member of the EGFR family. The IgG moiety may provide stability to the scFv moiety. The bispecific tetravalent antibody may block signalling for both AKT and MAPK/ERK pathways and may mediate antibody dependent cell-mediated cytotoxicity (ADCC) towards cells expressing either one or both antigens. In one embodiment, the bispecific tetravalent antibody is capable of binding both antigens simultaneously. In some embodiments, the bispecific tetravalent antibody provides stronger tumour inhibition in proliferation assays in vitro and in vivo than the mono-specific antibody parental control or combination of the mono-specific antibody parental controls.

In one embodiment, the disclosure provides a bispecific tetravalent antibody having two IgG1 heavy chains, two kappa light chains, and two single chain Fv (scFv) domains. The two IgG1 heavy chains and kappa light chains form an IgG moiety with a binding specificity to a first member of the EGFR family. The two scFv domains have a binding specificity to a second member of the EGFR family, and each scFv domain is connected to the C-terminus of either of the IgG1 heavy chains by a connector with an amino acid sequence (gly-gly-gly-gly-ser)$_n$, also known as (G$_4$S)$_n$, to provide a IgG1-connector connection. n is an integral of at least 1. For example, n may be 2, 3, 4, 5, 6, 7, 8, 9, 10, or 17. Each scFv domain has a structure order of N terminus—variable heavy—linker—variable light—C terminus. The linker may have an amino acid sequence of (gly-gly-gly-gly-ser)$_m$, also known as (G$_4$S)$_m$. m may be an integral of at least 2 or at least 3. For example, m may be 3, 4, 5, 6, 11, or12. In some embodiments, at least one or both of the IgG1 heavy chains are humanized or human. In some embodiments, at least one or both of the kappa light chains are humanized or human.

The EGFR family members may include EGFR, HER2, HER3, a fragment or a derivative thereof. In some embodiments, the first member of the EGFR family may be EGFR, HER2, a fragment or a derivative thereof. In some embodiments, the second member of the EGFR family may be HER3, a fragment or a derivative thereof. In one embodiment, the IgG moiety may have a binding specificity for HER3. In one embodiment, the scFv domains may have a binding specificity for EGFR. In one embodiment, the IgG moiety may have a binding specificity for HER3, and the scFv domains may have a binding specificity for EGFR. In one embodiment, the IgG moiety may have a binding specificity for EGFR. In one embodiment, the scFv domains may have a binding specificity for HER3. In one embodiment, the IgG moiety may a binding specificity for EGFR, and the scFv domains may have a binding specificity for HER3.

In some embodiments, the C terminus of one or both of the IgG1 heavy chains misses an amino acid residue. For example, the lysine reside may be deleted from the C terminus of the IgG1 chain before the connector is fused onto the C-terminus. The deletion of the lysine residue makes the IgG1-connector connection resistant to protease activity.

In some embodiments, one or both of the IgG1 heavy chains contain two mutations in the CH3 domain. For example, the two mutations may be reversion to the common residues in human CH3 domain.

In some embodiments, the IgG1 heavy chains may an amino acid sequences of or with at least 95%, 98% or 99% similarity to SEQ ID NO 7, 15, 23, 31, 39, 47, and 127. In some embodiments, the IgG1 heavy chain, connector, and scFv domain may have an amino acid sequence of or with at least 95%, 98% or 99% similarity to SEQ ID NO 56, 66, 76, 86, 98, 108, 118, and 136. In some embodiments, the kappa light chains may have an amino acid sequence of or with at least 95%, 98% or 99% similarity to SEQ ID NO 3, 11, 19, 27, 35, 43, 51, 61, 71, 81, 92, 103, 113, 123, and 131. In some embodiments, the variable light chain may an amino acid sequence of or with at least 95%, 98% or 99% similarity to SEQ ID NO 4, 12, 20, 28, 36, 44, 52, 62, 72, 82, 93, 104, 114, 124, and 132. In some embodiment, the variable heavy chain may have an amino acid sequence of or with at least 95%, 98% or 99% similarity to SEQ ID NO 8, 16, 24, 32, 40, 48, 57, 67, 77, 87, 99, 109, 119, 128, and 137.

In some embodiments, the IgG moiety has a binding specificity for HER3, and the scFv domains have a binding specificity for EGFR. In one embodiment, the IgG1 heavy chain, connector, and scFv domain have an amino acid sequence of SEQ ID NO 56, and the kappa light chain has an amino acid sequence of SEQ ID NO 51. In one embodiment, the IgG1 heavy chain, connector, and scFv domain have an amino acid sequence of SEQ ID NO 76, and the kappa light chain has an amino acid sequence of SEQ ID NO 71. In one embodiment, the IgG1 heavy chain, connector, and scFv domain have an amino acid sequence of SEQ ID NO 108, and the kappa light chain has an amino acid sequence of SEQ ID NO 103.

In some embodiments, the IgG moiety has a binding specificity for EGFR, and the scFv domains have a binding specificity for HER3. In one embodiment, the IgG1 heavy chain, connector, and scFv domain have an amino acid sequence of SEQ ID NO 66, and the kappa light chain has an amino acid sequence of SEQ ID NO 61. In one embodiment, the IgG1 heavy chain, connector, and scFv domain have an amino acid sequence of SEQ ID NO 86, and the kappa light chain has an amino acid sequence of SEQ ID NO 81. In one embodiment, the IgG1 heavy chain, connector, and scFv domain have an amino acid sequence of SEQ ID NO 98, and the kappa light chain has an amino acid sequence of SEQ ID NO 92. In one embodiment, the IgG1 heavy chain, connector, and scFv domain have an amino acid sequence of SEQ ID NO 118, and the kappa light chain has an amino acid sequence of SEQ ID NO 113. In one embodiment, the IgG1 heavy chain, connector, and scFv domain have an amino acid sequence of SEQ ID NO 136, and the kappa light chain has an amino acid sequence of SEQ ID NO 131.

The bispecific tetravalent antibodies have the activity of inhibiting cancer cell growth. In certain embodiments, an antibody of the invention has a dissociation constant (Kd) of ≤80 nM, ≤50 nM, ≤30 nM, ≤20 nM, ≤10 nM, or ≤0.1 nM for its target EGRF or HER3. The antibody may bind to both targets simultaneously. In some embodiments, the antibody binds to EGRF and HER3 with a Kd less than 50 nM. In some embodiments, the antibody binds to EGRF and/or HER3 with a Kd less than 40, 30, 25, 20, 19, 18 or 10 nM. In one embodiment, the antibody binds to EGRF with a Kd less than 30 nM and binds to HER3 with a Kd less than 30 nM. In one embodiment, the antibody binds to EGRF with a Kd less than 50 nM and binds to HER3 with a Kd less than 50 nM simultaneously.

In another aspect, the disclosure provides isolated nucleic acids encoding the bispecific tetravalent antibodies or its sub-component disclosed herein. The sub-component may be the IgG1 heavy chain, the kappa light chain, the variable light chain, or the variable heavy chain.

In a further aspect, the disclosure provides expression vectors having the isolated nucleic acids encoding the bispecific tetravalent antibody or its sub-component disclosed herein. The vectors may be expressible in a host cell. The host cell may be prokaryotic or eukaryotic.

In a further aspect, the disclosure provides host cells having the isolated nucleic acids encoding the bispecific tetravalent antibodies disclosed herein or the expression vectors including such nucleic acid sequences.

In a further aspect, the disclosure provides methods for producing bispecific tetravalent antibodies. In one embodiment, the method may include culturing the above-described host cells so that the antibody is produced.

In a further aspect, the disclosure provides immunoconjugates including the bispecific tetravalent antibodies described herein and a cytotoxic agent.

In a further aspect, the disclosure provides pharmaceutical compositions. The pharmaceutical composition may include the bispecific tetravalent antibodies or the immunoconjugates described herein and a pharmaceutically acceptable carrier. In some embodiments, the composition may further include radioisotope, radionuclide, a toxin, a therapeutic agent, a chemotherapeutic agent or a combination thereof.

In a further aspect, the disclosure provides methods of treating a subject with a cancer. In one embodiment, the method includes the step of administering to the subject an effective amount of a bispecific tetravalent antibody described herein. The cancer may include cells expressing at least two members of EGFR family including, for example, EGFR, HER2, HER3, a fragment or a derivative thereof. The cancer may be breast cancer, colorectal cancer, pancreatic cancer, head and neck cancer, melanoma, ovarian cancer, prostate cancer, and non-small lung cell cancer, glioma, esophageal cancer, nasopharyngeal cancer, anal cancer, rectal cancer, gastric cancer, bladder cancer, cervical cancer and brain cancer.

In one embodiment, the method may further include co-administering an effective amount of a therapeutic agent. The therapeutic agent may be, for example, an antibody, a chemotherapy agent, a cytotoxic agent, an enzyme, or a combination thereof. In some embodiments, the therapeutic agent may be an anti-estrogen agent, a receptor tyrosine inhibitor, or a combination thereof. In some embodiments, the therapeutic agent may be biologics. In one embodiment, the therapeutic agent may be a checkpoint inhibitor. In some embodiments, the therapeutic agent may include PD1, PDL1, CTLA4, 4-1BB, OX40, GITR, TIM3, LAG3, TIGIT, CD40, CD27, HVEM, BTLA, VISTA, B7H4, a derivative, a conjugate, or a fragment thereof. In some embodiments, the therapeutic agent may be capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, or a derivative thereof. In some embodiments, the subject in need of such treatment is a human.

In one embodiment, the disclosure provides methods for treating a subject by administering to the subject an effective amount of the bispecific tetravalent antibody to inhibit a biological activity of a HER receptor.

In one embodiment, the disclosure provides solutions having an effective concentration of the bispecific tetravalent antibody. In one embodiment, the solution is blood plasma in a subject.

A diagram of the general structure of IgG is shown in FIG. 1.

Figure 2:
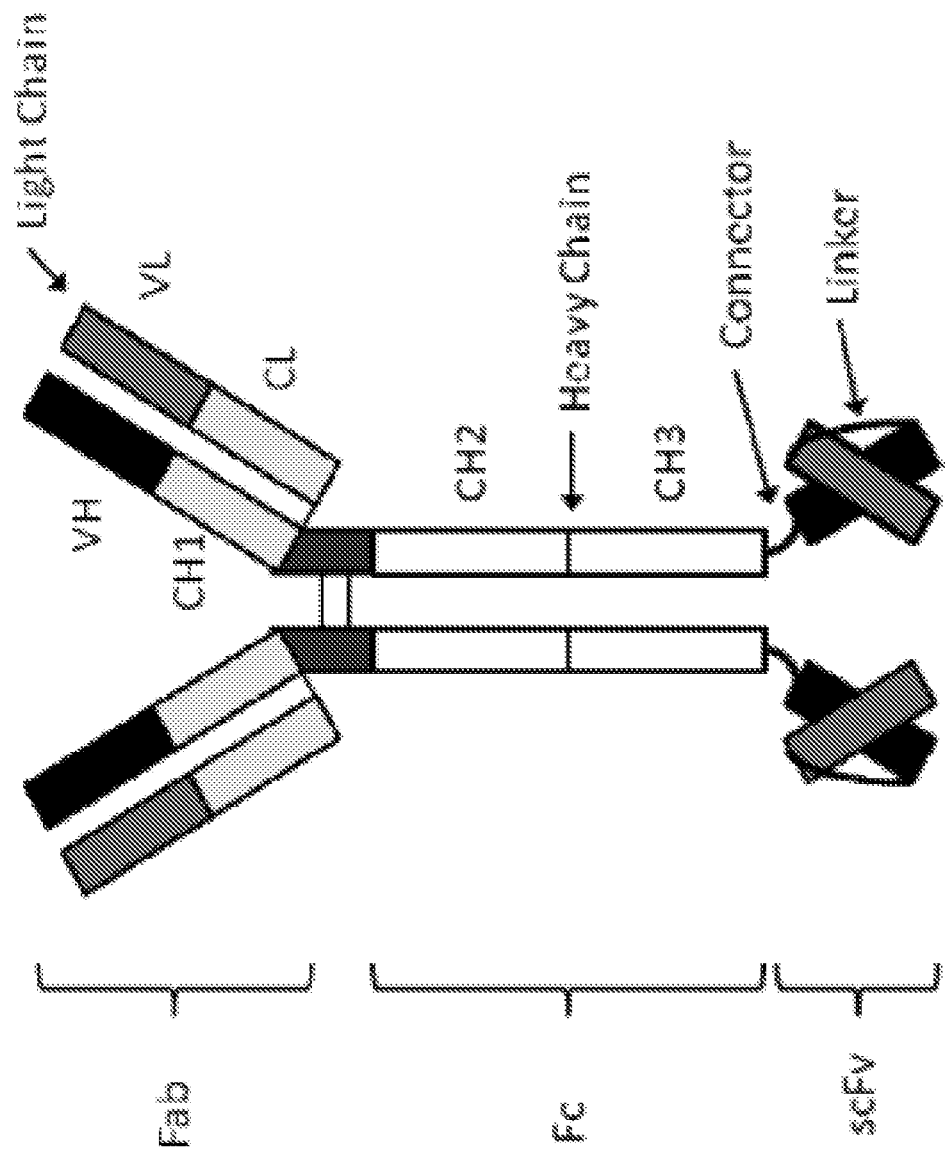
FIG. 2 is a diagram showing the domain structure of an example tetravalent bispecific antibody comprising an IgG moiety and two scFv moieties in accordance with one embodiment of the present invention.
Figure 3:
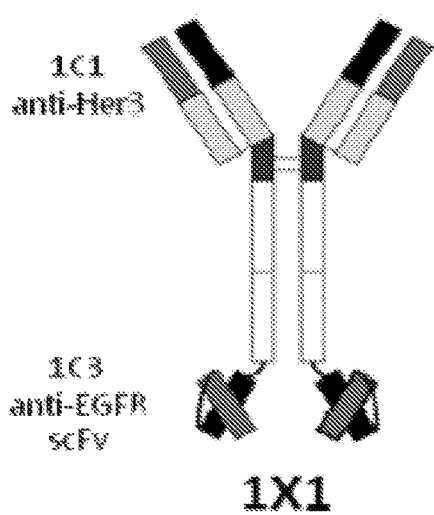
FIG. 3 shows the domain structure diagrams of example tetravalent bispecific antibodies 1X1, 1X2, 1X3, 1X4, 1X4.2, 1X5 and 1X6.
Figure 3:
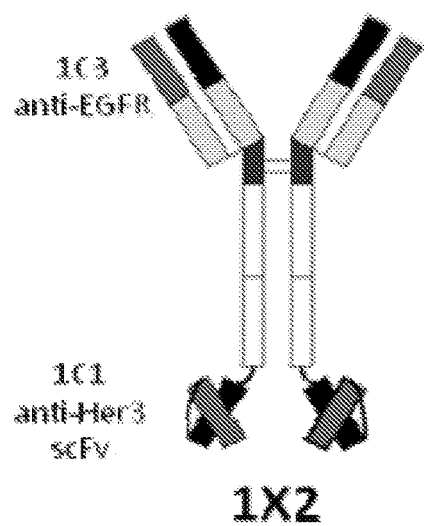
Figure 3:
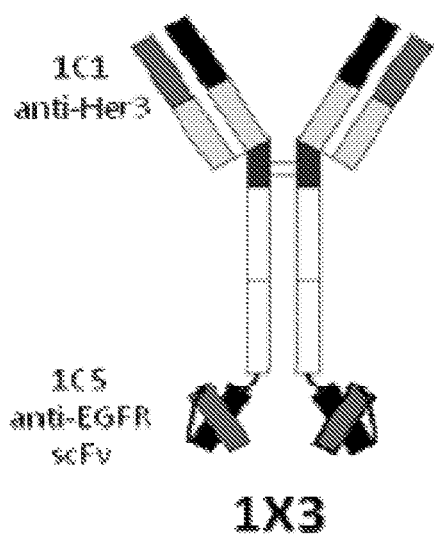
Figure 3:
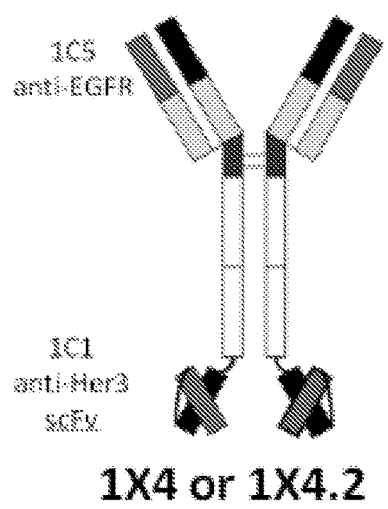
Figure 3:
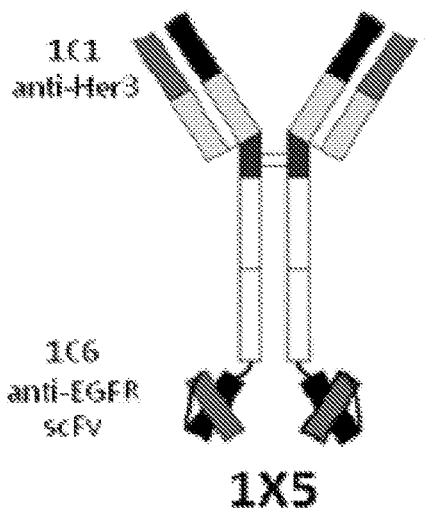
Figure 3:
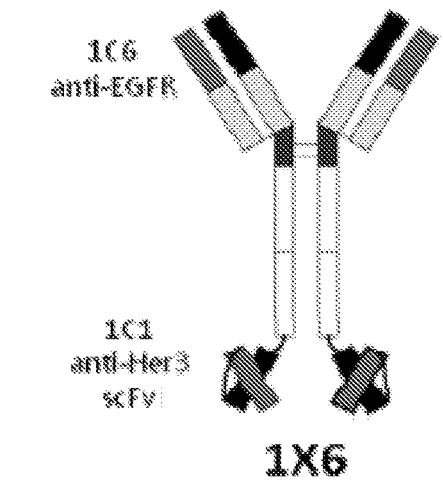
Figure 4:
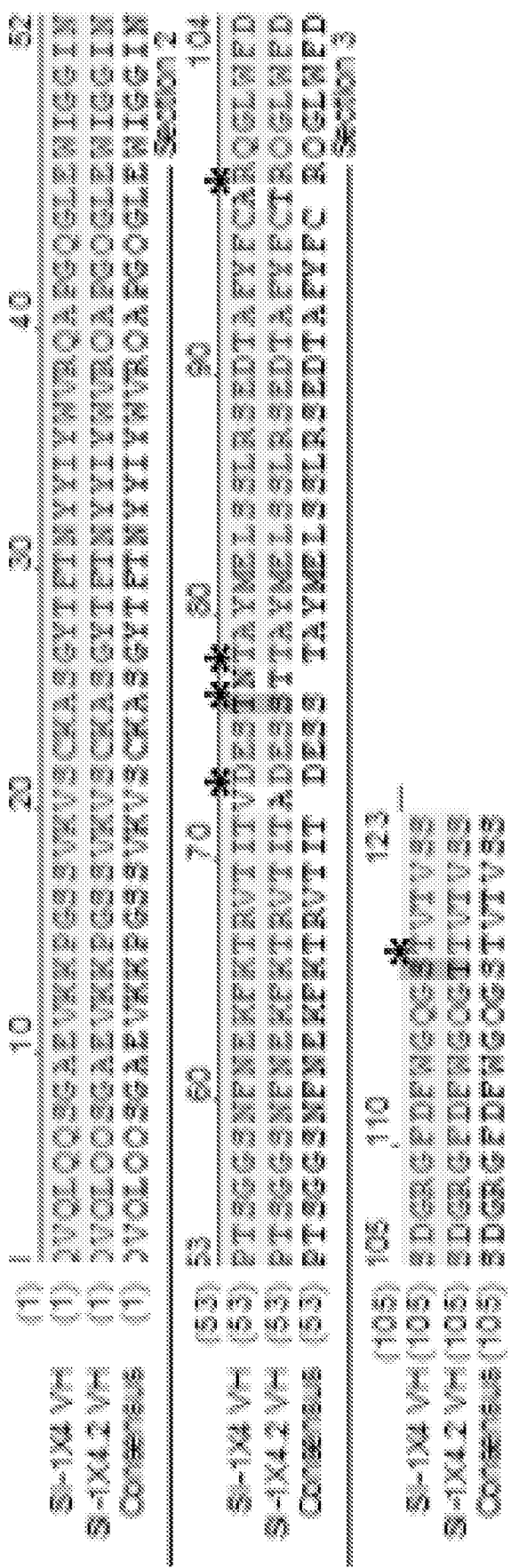
FIG. 4 shows the VH domain sequence comparison between SI-1X4 and SI-1X4.2 showing the 5 amino acid differences.

A diagram of the representative structure of the bispecific tetravalent antibodies according to some embodiments is shown in FIG. 2. In this example, the bispecific tetravalent antibody includes two human IgG1 heavy chains, two human kappa light chains, and two single chain Fv (scFv) domains. The two human IgG1 heavy chains and human kappa light chains form an IgG moiety with a binding specificity to one member of the EGFR family, and each of the two scFv domains is connected to the C-terminal residue of either of the human IgG1 heavy chains by a connector with an amino acid sequence of gly-gly-gly-gly-ser-gly-gly-gly-gly-ser ($(G_4S)_2$). Each scFv domain is in the order: N terminus—variable heavy—linker—variable light—C terminus. The linker is comprised of amino acid sequence of gly-gly-gly-gly-ser-gly-gly-gly-gly-ser-gly-gly-gly-gly-ser, also known as $(G_4S)_3$. For some embodiments of the bispecific tetravalent antibodies, the CH1, CH2, CH3, CL, Connector and Linker amino acid sequences are identical. Each bispecific tetravalent antibody has a bivalent anti-HER3 binding specificity on one end of the antibody and a bivalent anti-EGFR binding specificity on the other end. One pair of anti-HER3 variable heavy chain and variable light chain is designated as 1C1, and four pairs of anti-EGFR variable heavy chains and variable light chains are designated as 1C3, 1C5, 1C5.2, 1C6 and 1C6.4, respectively. The bispecific tetravalent antibodies are designated as 1X1, 1X2, 1X3, 1X4, 1X4.2, 1X5, 1X5.2, 1X6, and 1X6.4

In addition, a control molecule 1C4 (also designated as SI-1C4) was used in some of the studies. 1C4 is a bispecific antibody against EGFR and HER3 built on the two-in-one platform described by Schaefer et.al., 2011 (Schaefer et al., *Cancer Cell.* 2011 Oct. 18; 20(4):472-86). IC4 has a similar structure to a monoclonal antibody. The molecule can bind to either EGFR or HER3 on each Fab arm, but cannot engage both targets simultaneously on each Fab arm.

Variable light chain, variable heavy chain and single chain Fv (scFv) DNA fragments were generated by gene synthesis through an outside vendor. Human Gamma-1 heavy chain and human kappa light chain DNA fragments were generated by gene synthesis through an outside vendor. The fragments were assembled together by DNA ligation using restriction sites and cloned into a vector that is designed for transient expression in mammalian cells. The vector contains a strong CMV-derived promoter, and other upstream and downstream elements required for transient expression. The resulting IgG expression plasmids were verified as containing the expected DNA sequences by DNA sequencing.

Transient expression of the antibody constructs was achieved using transfection of suspension-adapted HEK293F cells with linear PEI as described elsewhere (see CSH Protocols; 2008; doi:10.1101/pdb.prot4977). Antibodies were purified from the resulting transfection supernatants using protein affinity chromatography and size exclusion chromatography if needed. Protein quality is analysed by Superdex 200 column. Protein used for all the assays have a purity of greater than 90%.

The bispecific antibody may be used for the treatment of cancer types with EGFR and HER3 co-expressions, including without limitation colon cancer, head and neck squamous cell carcinoma, lung cancer, glioma, pancreatic cancer, nasopharyngeal cancer and other cancer types.

The bispecific antibody is of tetravalent dual specificity. The example antibody may include an IgG and two scFv, which provides two different binding specificities compared to mono-specific antibody IgG. The IgG component provides stability and improved serum half-life over other bispecific antibodies that used only scFv such as BiTE technology (Lutterbuese et al., *Proceedings of the National Academy of Sciences of the United States of America* 107.28 (2010): 12605-12610. PMC. Web. 2 Dec. 2014) and others (for example, U.S. Pat. No. 7,332,585B2). It is also capable of mediating ADCC while those without Fc component cannot (for example, U.S. Pat. No. 7,332,585B2). The tetravalent dual specificity nature provides the bispecific antibody a simultaneous binding capability over some other bispecific antibodies, which may only bind one antigen at a time (Schanzer et al, *Antimicrob. Agents Chemother.* 2011, 55(5):2369; EP272942A1).

For the convenient of narration, the sequences of or related to the bispecific antibodies are summarized in TABLE 1 herein below.

TABLE 1

Summary of nucleotide and amino acid sequences of or related to the bispecific antibodies.

| SI-1C1 SEQUENCES | |
|---|---|
| SEQ ID NO 1 | SI-1C1 LIGHT CHAIN FULL-LENGTH NUCLEOTIDE SEQUENCE |
| SEQ ID NO 2 | SI-1C1 LIGHT CHAIN VARIABLE LIGHT CHAIN NUCLEOTIDE SEQUENCE |
| SEQ ID NO 3 | SI-1C1 LIGHT CHAIN FULL-LENGTH AMINO ACID SEQUENCE. HUMAN KAPPA CONSTANT DOMAIN IS UNDERLINED |
| SEQ ID NO 4 | SI-1C1 LIGHT CHAIN VARIABLE LIGHT CHAIN AMINO ACID SEQUENCE. COMPLEMENTARITY DETERMINING REGIONS ARE UNDERLINED |
| SEQ ID NO 5 | SI-1C1 HEAVY CHAIN FULL-LENGTH NUCLEOTIDE SEQUENCE |
| SEQ ID NO 6 | SI-1C1 HEAVY CHAIN VARIABLE HEAVY CHAIN NUCLEOTIDE SEQUENCE |
| SEQ ID NO 7 | SI-1C1 HEAVY CHAIN FULL-LENGTH AMINO ACID SEQUENCE. HUMAN GAMMA-1 DOMAIN IS UNDERLINED |
| SEQ ID NO 8 | SI-1C1 HEAVY CHAIN VARIABLE HEAVY CHAIN AMINO ACID SEQUENCE. COMPLEMENTARITY DETERMINING REGIONS ARE UNDERLINED |
| SI-1C3 SEQUENCES | |
| SEQ ID NO 9 | SI-1C3 LIGHT CHAIN FULL-LENGTH NUCLEOTIDE SEQUENCE |
| SEQ ID NO 10 | SI-1C3 LIGHT CHAIN VARIABLE LIGHT CHAIN NUCLEOTIDE SEQUENCE |
| SEQ ID NO 11 | SI-1C3 LIGHT CHAIN FULL-LENGTH AMINO ACID SEQUENCE. HUMAN KAPPA CONSTANT DOMAIN IS UNDERLINED |
| SEQ ID NO 12 | SI-1C3 LIGHT CHAIN VARIABLE LIGHT CHAIN AMINO ACID SEQUENCE. COMPLEMENTARITY DETERMINING REGIONS ARE UNDERLINED |
| SEQ ID NO 13 | SI-1C3 HEAVY CHAIN FULL-LENGTH NUCLEOTIDE SEQUENCE |
| SEQ ID NO 14 | SI-1C3 HEAVY CHAIN VARIABLE HEAVY CHAIN NUCLEOTIDE SEQUENCE |

TABLE 1-continued

Summary of nucleotide and amino acid sequences
of or related to the bispecific antibodies.

| | |
|---|---|
| SEQ ID NO 15 | SI-1C3 HEAVY CHAIN FULL-LENGTH AMINO ACID SEQUENCE. HUMAN GAMMA-1 DOMAIN IS UNDERLINED |
| SEQ ID NO 16 | SI-1C3 HEAVY CHAIN VARIABLE HEAVY CHAIN AMINO ACID SEQUENCE. COMPLEMENTARITY DETERMINING REGIONS ARE UNDERLINED |
| SI-1C4 SEQUENCES | |
| SEQ ID NO 17 | SI-1C4 LIGHT CHAIN FULL-LENGTH NUCLEOTIDE SEQUENCE |
| SEQ ID NO 18 | SI-1C4 LIGHT CHAIN VARIABLE LIGHT CHAIN NUCLEOTIDE SEQUENCE |
| SEQ ID NO 19 | SI-1C4 LIGHT CHAIN FULL-LENGTH AMINO ACID SEQUENCE. HUMAN KAPPA CONSTANT DOMAIN IS UNDERLINED |
| SEQ ID NO 20 | SI-1C4 LIGHT CHAIN VARIABLE LIGHT CHAIN AMINO ACID SEQUENCE. COMPLEMENTARITY DETERMINING REGIONS ARE UNDERLINED |
| SEQ ID NO 21 | SI-1C4 HEAVY CHAIN FULL-LENGTH NUCLEOTIDE SEQUENCE |
| SEQ ID NO 22 | SI-1C4 HEAVY CHAIN VARIABLE HEAVY CHAIN NUCLEOTIDE SEQUENCE |
| SEQ ID NO 23 | SI-1C4 HEAVY CHAIN FULL-LENGTH AMINO ACID SEQUENCE. HUMAN GAMMA-1 DOMAIN IS UNDERLINED |
| SEQ ID NO 24 | SI-1C4 HEAVY CHAIN VARIABLE HEAVY CHAIN AMINO ACID SEQUENCE. COMPLEMENTARITY DETERMINING REGIONS ARE UNDERLINED |
| SI-1C5 SEQUENCES | |
| SEQ ID NO 25 | SI-1C5 LIGHT CHAIN FULL-LENGTH NUCLEOTIDE SEQUENCE |
| SEQ ID NO 26 | SI-1C5 LIGHT CHAIN VARIABLE LIGHT CHAIN NUCLEOTIDE SEQUENCE |
| SEQ ID NO 27 | SI-1C5 LIGHT CHAIN FULL-LENGTH AMINO ACID SEQUENCE. HUMAN KAPPA CONSTANT DOMAIN IS UNDERLINED |
| SEQ ID NO 28 | SI-1C5 LIGHT CHAIN VARIABLE LIGHT CHAIN AMINO ACID SEQUENCE. COMPLEMENTARITY DETERMINING REGIONS ARE UNDERLINED |
| SEQ ID NO 29 | SI-1C5 HEAVY CHAIN FULL-LENGTH NUCLEOTIDE SEQUENCE |
| SEQ ID NO 30 | SI-1C5 HEAVY CHAIN VARIABLE HEAVY CHAIN NUCLEOTIDE SEQUENCE |
| SEQ ID NO 31 | SI-1C5 HEAVY CHAIN FULL-LENGTH AMINO ACID SEQUENCE. HUMAN GAMMA-1 DOMAIN IS UNDERLINED |
| SEQ ID NO 32 | SI-1C5 HEAVY CHAIN VARIABLE HEAVY CHAIN AMINO ACID SEQUENCE. COMPLEMENTARITY DETERMINING REGIONS ARE UNDERLINED |
| SI-1C5.2 SEQUENCES | |
| SEQ ID NO 33 | SI1C5.2 LIGHT CHAIN FULL-LENGTH NUCLEOTIDE SEQUENCE |
| SEQ ID NO 34 | SI-1C5.2 LIGHT CHAIN VARIABLE LIGHT CHAIN NUCLEOTIDE SEQUENCE |
| SEQ ID NO 35 | SI-1C5.2 LIGHT CHAIN FULL-LENGTH AMINO ACID SEQUENCE. HUMAN KAPPA CONSTANT DOMAIN IS UNDERLINED |
| SEQ ID NO 36 | SI-1C5.2 LIGHT CHAIN VARIABLE LIGHT CHAIN AMINO ACID SEQUENCE. COMPLEMENTARITY DETERMINING REGIONS ARE UNDERLINED |
| SEQ ID NO 37 | SI-1C5.2 HEAVY CHAIN FULL-LENGTH NUCLEOTIDE SEQUENCE |
| SEQ ID NO 38 | SI-1C5.2 HEAVY CHAIN VARIABLE HEAVY CHAIN NUCLEOTIDE SEQUENCE |
| SEQ ID NO 39 | SI-1C5.2 HEAVY CHAIN FULL-LENGTH AMINO ACID SEQUENCE. HUMAN GAMMA-1 DOMAIN IS UNDERLINED |
| SEQ ID NO 40 | SI-1C5.2 HEAVY CHAIN VARIABLE HEAVY CHAIN AMINO ACID SEQUENCE. COMPLEMENTARITY DETERMINING REGIONS ARE UNDERLINED |
| SI-1C6 SEQUENCES | |
| SEQ ID NO 41 | SI-1C6 LIGHT CHAIN FULL-LENGTH NUCLEOTIDE SEQUENCE |

TABLE 1-continued

Summary of nucleotide and amino acid sequences
of or related to the bispecific antibodies.

| | |
|---|---|
| SEQ ID NO 42 | SI-1C6 LIGHT CHAIN VARIABLE LIGHT CHAIN NUCLEOTIDE SEQUENCE |
| SEQ ID NO 43 | SI-1C6 LIGHT CHAIN FULL-LENGTH AMINO ACID SEQUENCE. HUMAN KAPPA CONSTANT DOMAIN IS UNDERLINED |
| SEQ ID NO 44 | SI-1C6 LIGHT CHAIN VARIABLE LIGHT CHAIN AMINO ACID SEQUENCE. COMPLEMENTARITY DETERMINING REGIONS ARE UNDERLINED |
| SEQ ID NO 45 | SI-1C6 HEAVY CHAIN FULL-LENGTH NUCLEOTIDE SEQUENCE |
| SEQ ID NO 46 | SI-1C6 HEAVY CHAIN VARIABLE HEAVY CHAIN NUCLEOTIDE SEQUENCE |
| SEQ ID NO 47 | SI-1C6 HEAVY CHAIN FULL-LENGTH AMINO ACID SEQUENCE. HUMAN GAMMA-1 DOMAIN IS UNDERLINED |
| SEQ ID NO 48 | SI-1C6 HEAVY CHAIN VARIABLE HEAVY CHAIN AMINO ACID SEQUENCE. COMPLEMENTARITY DETERMINING REGIONS ARE UNDERLINED |
| SI-1X1 SEQUENCES | |
| SEQ ID NO 49 | SI1X1 LIGHT CHAIN FULL-LENGTH NUCLEOTIDE SEQUENCE |
| SEQ ID NO 50 | SI-1X1 LIGHT CHAIN VARIABLE LIGHT CHAIN NUCLEOTIDE SEQUENCE |
| SEQ ID NO 51 | SI-1X1 LIGHT CHAIN FULL-LENGTH AMINO ACID SEQUENCE. HUMAN KAPPA CONSTANT DOMAIN IS UNDERLINED |
| SEQ ID NO 52 | SI-1X1 LIGHT CHAIN VARIABLE LIGHT CHAIN AMINO ACID SEQUENCE. COMPLEMENTARITY DETERMINING REGIONS ARE UNDERLINED |
| SEQ ID NO 53 | SI1X1 BISPECIFIC HEAVY CHAIN FULL-LENGTH NUCLEOTIDE SEQUENCE |
| SEQ ID NO 54 | SI-1X1 BISPECIFIC HEAVY CHAIN VARIABLE HEAVY CHAIN NUCLEOTIDE SEQUENCE |
| SEQ ID NO 55 | SI-1X1 BISPECIFIC HEAVY CHAIN SCFV NUCLEOTIDE SEQUENCE |
| SEQ ID NO 56 | SI-1X1 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 57 | SI-1X1 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 58 | SI1X1 BISPECIFIC HEAVY CHAIN SCFV AMINO ACID SEQUENCE. ORDER: VH - LINKER - VL. COMPLEMENTARITY DETERMINING REGIONS ARE UNDERLINED. LINKER IS IN BOLD ITALICS |
| SI-1X2 SEQUENCES | |
| SEQ ID NO 59 | SI-1X2 LIGHT CHAIN FULL-LENGTH NUCLEOTIDE SEQUENCE |
| SEQ ID NO 60 | SI-1X2 LIGHT CHAIN VARIABLE LIGHT CHAIN NUCLEOTIDE SEQUENCE |
| SEQ ID NO 61 | SI-1X2 LIGHT CHAIN FULL-LENGTH AMINO ACID SEQUENCE. HUMAN KAPPA CONSTANT DOMAIN IS UNDERLINED |
| SEQ ID NO 62 | SI-1X2 LIGHT CHAIN VARIABLE LIGHT CHAIN AMINO ACID SEQUENCE. COMPLEMENTARITY DETERMINING REGIONS ARE UNDERLINED |
| SEQ ID NO 63 | SI-1X2 BISPECIFIC HEAVY CHAIN FULL-LENGTH NUCLEOTIDE SEQUENCE |
| SEQ ID NO 64 | SI-1X2 BISPECIFIC HEAVY CHAIN VARIABLE HEAVY CHAIN NUCLEOTIDE SEQUENCE |
| SEQ ID NO 65 | SI-1X2 BISPECIFIC HEAVY CHAIN SCFV NUCLEOTIDE SEQUENCE |
| SEQ ID NO 66 | SI-1X2 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 67 | SI-1X2 BISPECIFIC HEAVY CHAIN VARIABLE HEAVY CHAIN AMINO ACID SEQUENCE. COMPLEMENTARITY DETERMINING REGIONS ARE UNDERLINED |

TABLE 1-continued

Summary of nucleotide and amino acid sequences of or related to the bispecific antibodies.

| | |
|---|---|
| SEQ ID NO 68 | SI-1X2 BISPECIFIC HEAVY CHAIN SCFV AMINO ACID SEQUENCE. ORDER: VH - LINKER - VL. COMPLEMENTARITY DETERMINING REGIONS ARE UNDERLINED. LINKER IS IN BOLD ITALICS |
| SI-1X3 SEQUENCES | |
| SEQ ID NO 69 | SI-1X3 LIGHT CHAIN FULL-LENGTH NUCLEOTIDE SEQUENCE |
| SEQ ID NO 70 | SI-1X3 LIGHT CHAIN VARIABLE LIGHT CHAIN NUCLEOTIDE SEQUENCE |
| SEQ ID NO 71 | SI-1X3 LIGHT CHAIN FULL-LENGTH AMINO ACID SEQUENCE. HUMAN KAPPA CONSTANT DOMAIN IS UNDERLINED |
| SEQ ID NO 72 | SI-1X3 LIGHT CHAIN VARIABLE LIGHT CHAIN AMINO ACID SEQUENCE. COMPLEMENTARITY DETERMINING REGIONS ARE UNDERLINED |
| SEQ ID NO 73 | SI-1X3 BISPECIFIC HEAVY CHAIN FULL-LENGTH NUCLEOTIDE SEQUENCE |
| SEQ ID NO 74 | SI-1X3 BISPECIFIC HEAVY CHAIN VARIABLE HEAVY CHAIN NUCLEOTIDE SEQUENCE |
| SEQ ID NO 75 | SI-1X3 BISPECIFIC HEAVY CHAIN SCFV NUCLEOTIDE SEQUENCE |
| SEQ ID NO 76 | SI-1X3 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 77 | SI-1X3 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 78 | SI-1X3 BISPECIFIC HEAVY CHAIN SCFV AMINO ACID SEQUENCE. ORDER: VH - LINKER - VL. COMPLEMENTARITY DETERMINING REGIONS ARE UNDERLINED. LINKER IS IN BOLD ITALICS |
| SI-1X4 SEQUENCES | |
| SEQ ID NO 79 | SI-1X4 LIGHT CHAIN FULL-LENGTH NUCLEOTIDE SEQUENCE |
| SEQ ID NO 80 | SI-1X4 LIGHT CHAIN VARIABLE LIGHT CHAIN NUCLEOTIDE SEQUENCE |
| SEQ ID NO 81 | SI-1X4 LIGHT CHAIN FULL-LENGTH AMINO ACID SEQUENCE. HUMAN KAPPA CONSTANT DOMAIN IS UNDERLINED |
| SEQ ID NO 82 | SI-1X4 LIGHT CHAIN VARIABLE LIGHT CHAIN AMINO ACID SEQUENCE. COMPLEMENTARITY DETERMINING REGIONS ARE UNDERLINED |
| SEQ ID NO 83 | SI-1X4 BISPECIFIC HEAVY CHAIN FULL-LENGTH NUCLEOTIDE SEQUENCE |
| SEQ ID NO 84 | SI-1X4 BISPECIFIC HEAVY CHAIN VARIABLE HEAVY CHAIN NUCLEOTIDE SEQUENCE |
| SEQ ID NO 85 | SI-1X4 BISPECIFIC HEAVY CHAIN SCFV NUCLEOTIDE SEQUENCE |
| SEQ ID NO 86 | SI-1X4 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 87 | SI-1X4 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 88 | SI-1X4 BISPECIFIC HEAVY CHAIN SCFV AMINO ACID SEQUENCE. ORDER: VH - LINKER - VL. COMPLEMENTARITY DETERMINING REGIONS ARE UNDERLINED. LINKER IS IN BOLD ITALICS |
| SI-1X4.2 SEQUENCES | |
| SEQ ID NO 89 | SI-1X4.2 LIGHT CHAIN FULL-LENGTH NUCLEOTIDE SEQUENCE |
| SEQ ID NO 90 | SI-1X4.2 LIGHT CHAIN VARIABLE LIGHT CHAIN NUCLEOTIDE SEQUENCE |
| SEQ ID NO 91 | SI-1X4.2 LIGHT CHAIN VARIABLE LIGHT CHAIN NUCLEOTIDE SEQUENCE CODON OPTIMIZED FOR CHO EXPRESSION |
| SEQ ID NO 92 | SI-1X4.2 LIGHT CHAIN FULL-LENGTH AMINO ACID SEQUENCE. HUMAN KAPPA CONSTANT DOMAIN IS UNDERLINED |

TABLE 1-continued

Summary of nucleotide and amino acid sequences
of or related to the bispecific antibodies.

| | |
|---|---|
| SEQ ID NO 93 | SI-1X4.2 LIGHT CHAIN VARIABLE LIGHT CHAIN AMINO ACID SEQUENCE. COMPLEMENTARITY DETERMINING REGIONS ARE UNDERLINED |
| SEQ ID NO 94 | SI-1X4.2 BISPECIFIC HEAVY CHAIN FULL-LENGTH NUCLEOTIDE SEQUENCE |
| SEQ ID NO 95 | SI-1X4.2 BISPECIFIC HEAVY CHAIN VARIABLE HEAVY CHAIN NUCLEOTIDE SEQUENCE |
| SEQ ID NO 96 | SI-1X4.2 BISPECIFIC HEAVY CHAIN VARIABLE HEAVY CHAIN NUCLEOTIDE SEQUENCE CODON OPTIMIZED FOR CHO EXPRESSION |
| SEQ ID NO 97 | SI-1X4.2 BISPECIFIC HEAVY CHAIN SCFV NUCLEOTIDE SEQUENCE |
| SEQ ID NO 98 | SI-1X4.2 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 99 | SI-1X4.2 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 100 | SI-1X4.2 BISPECIFIC HEAVY CHAIN SCFV AMINO ACID SEQUENCE. ORDER: VH - LINKER - VL. COMPLEMENTARITY DETERMINING REGIONS ARE UNDERLINED. LINKER IS IN BOLD ITALICS |
| SI-1X5 SEQUENCES | |
| SEQ ID NO 101 | SI-1X5 LIGHT CHAIN FULL-LENGTH NUCLEOTIDE SEQUENCE |
| SEQ ID NO 102 | SI-1X5 LIGHT CHAIN VARIABLE LIGHT CHAIN NUCLEOTIDE SEQUENCE |
| SEQ ID NO 103 | SI-1X5 LIGHT CHAIN FULL-LENGTH AMINO ACID SEQUENCE. HUMAN KAPPA CONSTANT DOMAIN IS UNDERLINED |
| SEQ ID NO 104 | SI-1X5 LIGHT CHAIN VARIABLE LIGHT CHAIN AMINO ACID SEQUENCE. COMPLEMENTARITY DETERMINING REGIONS ARE UNDERLINED |
| SEQ ID NO 105 | SI-1X5 BISPECIFIC HEAVY CHAIN FULL-LENGTH NUCLEOTIDE SEQUENCE |
| SEQ ID NO 106 | SI-1X5 BISPECIFIC HEAVY CHAIN VARIABLE HEAVY CHAIN NUCLEOTIDE SEQUENCE |
| SEQ ID NO 107 | SI-1X5 BISPECIFIC HEAVY CHAIN SCFV NUCLEOTIDE SEQUENCE |
| SEQ ID NO 108 | SI-1X5 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |
| SEQ ID NO 109 | SI-1X5 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 110 | SI-1X5 BISPECIFIC HEAVY CHAIN SCFV AMINO ACID SEQUENCE. ORDER: VH - LINKER - VL. COMPLEMENTARITY DETERMINING REGIONS ARE UNDERLINED. LINKER IS IN BOLD ITALICS |
| SI-1X6 SEQUENCES | |
| SEQ ID NO 111 | SI-1X6 LIGHT CHAIN FULL-LENGTH NUCLEOTIDE SEQUENCE |
| SEQ ID NO 112 | SI-1X6 LIGHT CHAIN VARIABLE LIGHT CHAIN NUCLEOTIDE SEQUENCE |
| SEQ ID NO 113 | SI-1X6 LIGHT CHAIN FULL-LENGTH AMINO ACID SEQUENCE. HUMAN KAPPA CONSTANT DOMAIN IS UNDERLINED |
| SEQ ID NO 114 | SI-1X6 LIGHT CHAIN VARIABLE LIGHT CHAIN AMINO ACID SEQUENCE. COMPLEMENTARITY DETERMINING REGIONS ARE UNDERLINED |
| SEQ ID NO 115 | SI-1X6 BISPECIFIC HEAVY CHAIN FULL-LENGTH NUCLEOTIDE SEQUENCE |
| SEQ ID NO 116 | SI-1X6 BISPECIFIC HEAVY CHAIN VARIABLE HEAVY CHAIN NUCLEOTIDE SEQUENCE |
| SEQ ID NO 117 | SI-1X6 BISPECIFIC HEAVY CHAIN SCFV NUCLEOTIDE SEQUENCE |
| SEQ ID NO 118 | SI-1X6 BISPECIFIC HEAVY CHAIN FULL-LENGTH AMINO ACID SEQUENCE. HUMAN GAMMA-1 DOMAIN IS UNDERLINED, CONNECTOR IS IN ITALICS, SCFV IS IN BOLD |

TABLE 1-continued

Summary of nucleotide and amino acid sequences of or related to the bispecific antibodies.

| | |
|---|---|
| SEQ ID NO 119 | SI-1X6 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 120 | SI-1X6 BISPECIFIC HEAVY CHAIN SCFV AMINO ACID SEQUENCE. ORDER: VH - LINKER - VL. COMPLEMENTARITY DETERMINING REGIONS ARE UNDERLINED. LINKER IS IN BOLD ITALICS |
| SI-1C6.2 SEQUENCES | |
| SEQ ID NO 121 | SI-1C6.2 LIGHT CHAIN FULL-LENGTH NUCLEOTIDE SEQUENCE |
| SEQ ID NO 122 | SI-1C6.2 LIGHT CHAIN VARIABLE LIGHT CHAIN NUCLEOTIDE SEQUENCE |
| SEQ ID NO 123 | SI-1C6.2 LIGHT CHAIN FULL-LENGTH AMINO ACID SEQUENCE. HUMAN KAPPA CONSTANT DOMAIN IS UNDERLINED |
| SEQ ID NO 124 | SI-1C6.2 LIGHT CHAIN VARIABLE LIGHT CHAIN AMINO ACID SEQUENCE. COMPLEMENTARITY DETERMINING REGIONS ARE UNDERLINED |
| SEQ ID NO 125 | SI-1C6.2 HEAVY CHAIN FULL-LENGTH NUCLEOTIDE SEQUENCE |
| SEQ ID NO 126 | SI-1C6.2 HEAVY CHAIN VARIABLE HEAVY CHAIN NUCLEOTIDE SEQUENCE |
| SEQ ID NO 127 | SI-1C6.2 HEAVY CHAIN FULL-LENGTH AMINO ACID SEQUENCE. HUMAN GAMMA-1 DOMAIN IS UNDERLINED |
| SEQ ID NO 128 | SI-1C6.2 HEAVY CHAIN VARIABLE HEAVY CHAIN AMINO ACID SEQUENCE. COMPLEMENTARITY DETERMINING REGIONS ARE UNDERLINED |
| SI-1X6.4 SEQUENCES | |
| SEQ ID NO 129 | SI-1X6.4 LIGHT CHAIN FULL-LENGTH NUCLEOTIDE SEQUENCE |
| SEQ ID NO 130 | SI-1X6.4 LIGHT CHAIN VARIABLE LIGHT CHAIN NUCLEOTIDE SEQUENCE |
| SEQ ID NO 131 | SI-1X6.4 LIGHT CHAIN FULL-LENGTH AMINO ACID SEQUENCE. HUMAN KAPPA CONSTANT DOMAIN IS UNDERLINED |
| SEQ ID NO 132 | SI-1X6.4 LIGHT CHAIN VARIABLE LIGHT CHAIN AMINO ACID SEQUENCE. COMPLEMENTARITY DETERMINING REGIONS ARE UNDERLINED |
| SEQ ID NO 133 | SI-1X6.4 BISPECIFIC HEAVY CHAIN FULL-LENGTH NUCLEOTIDE SEQUENCE |
| SEQ ID NO 134 | SI-1X6.4 BISPECIFIC HEAVY CHAIN VARIABLE HEAVY CHAIN NUCLEOTIDE SEQUENCE |
| SEQ ID NO 135 | SI-1X6.4 BISPECIFIC HEAVY CHAIN SCFV NUCLEOTIDE SEQUENCE |
| SEQ ID NO 136 | SI-1X6.4 BISPECIFIC HEAVY CHAIN FULL-LENGTH AMINO ACID SEQUENCE. HUMAN GAMMA-1 DOMAIN IS UNDERLINED. CONNECTOR IS IN ITALICS. SCFV IS IN BOLD |
| SEQ ID NO 137 | SI-1X6.4 BISPECIFIC HEAVY CHAIN VARIABLE HEAVY CHAIN AMINO ACID SEQUENCE. COMPLEMENTARITY DETERMINING REGIONS ARE UNDERLINED |
| SEQ ID NO 138 | SI-1X6.4 BISPECIFIC HEAVY CHAIN SCFV AMINO ACID SEQUENCE. ORDER: VH - LINKER - VL. COMPLEMENTARITY DETERMINING REGIONS ARE UNDERLINED. LINKER IS IN BOLD ITALICS |

EXAMPLES

While The following examples are provided by way of illustration only and not by way of limitation. Those of skill in the art will readily recognize a variety of non-critical parameters that could be changed or modified to yield essentially the same or similar results.

Example 1

Sequence Differences Between SI-1X4 and SI-1X4.2

Figure 5:
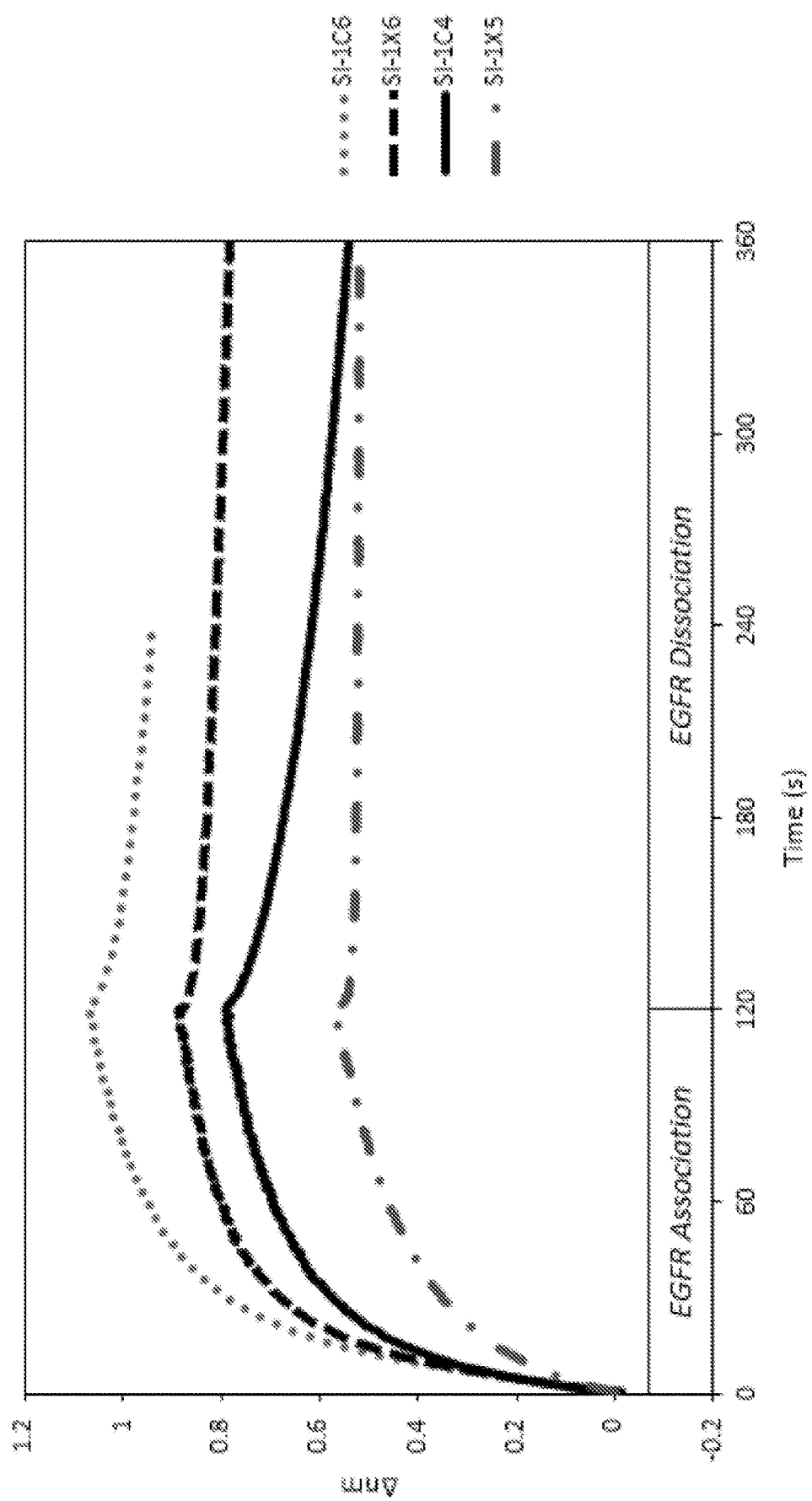
FIGS. 5 and 6 are graphs showing monomeric EGFR binding by BLI.
Figure 6:
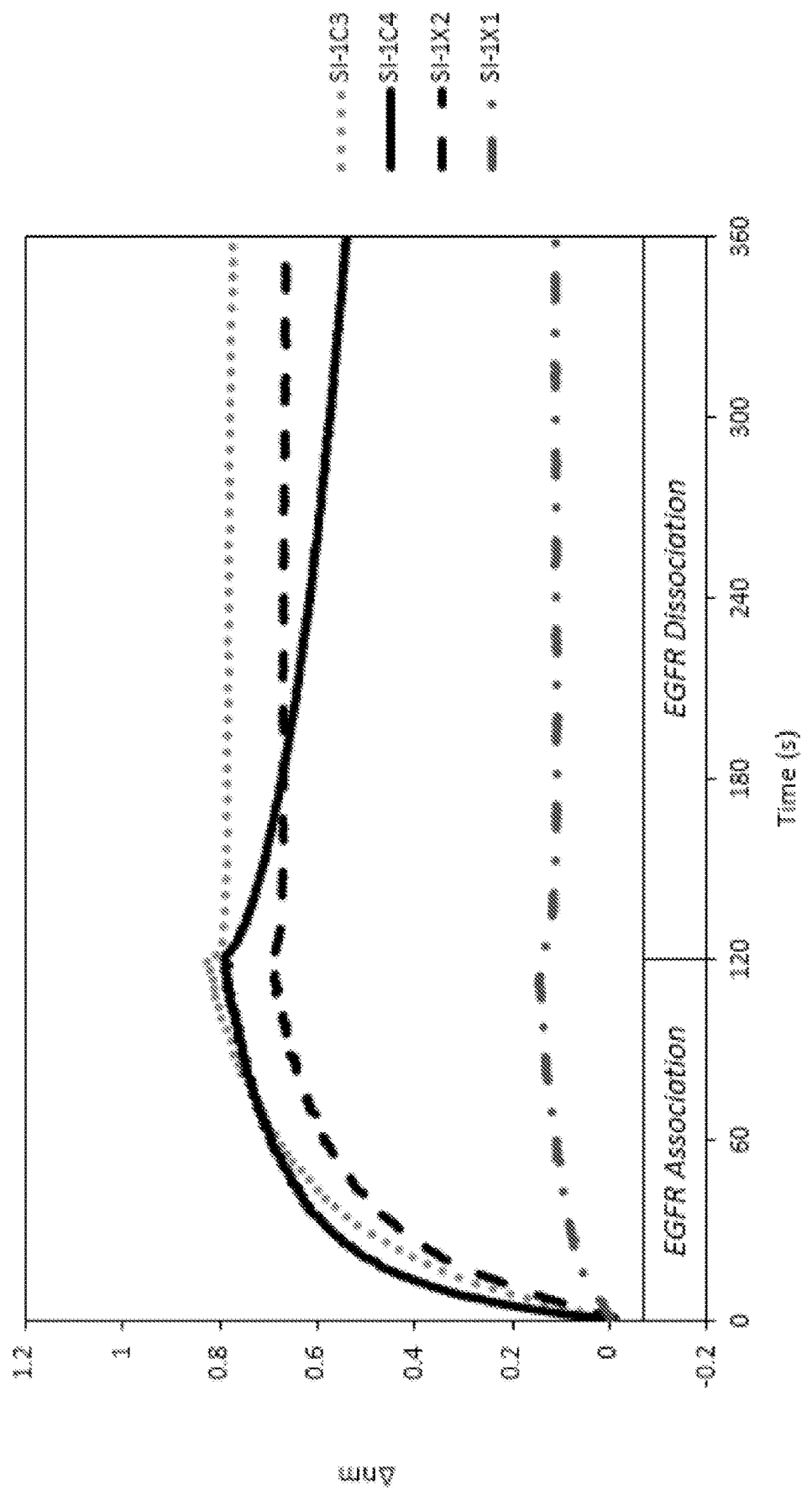
Figure 7:
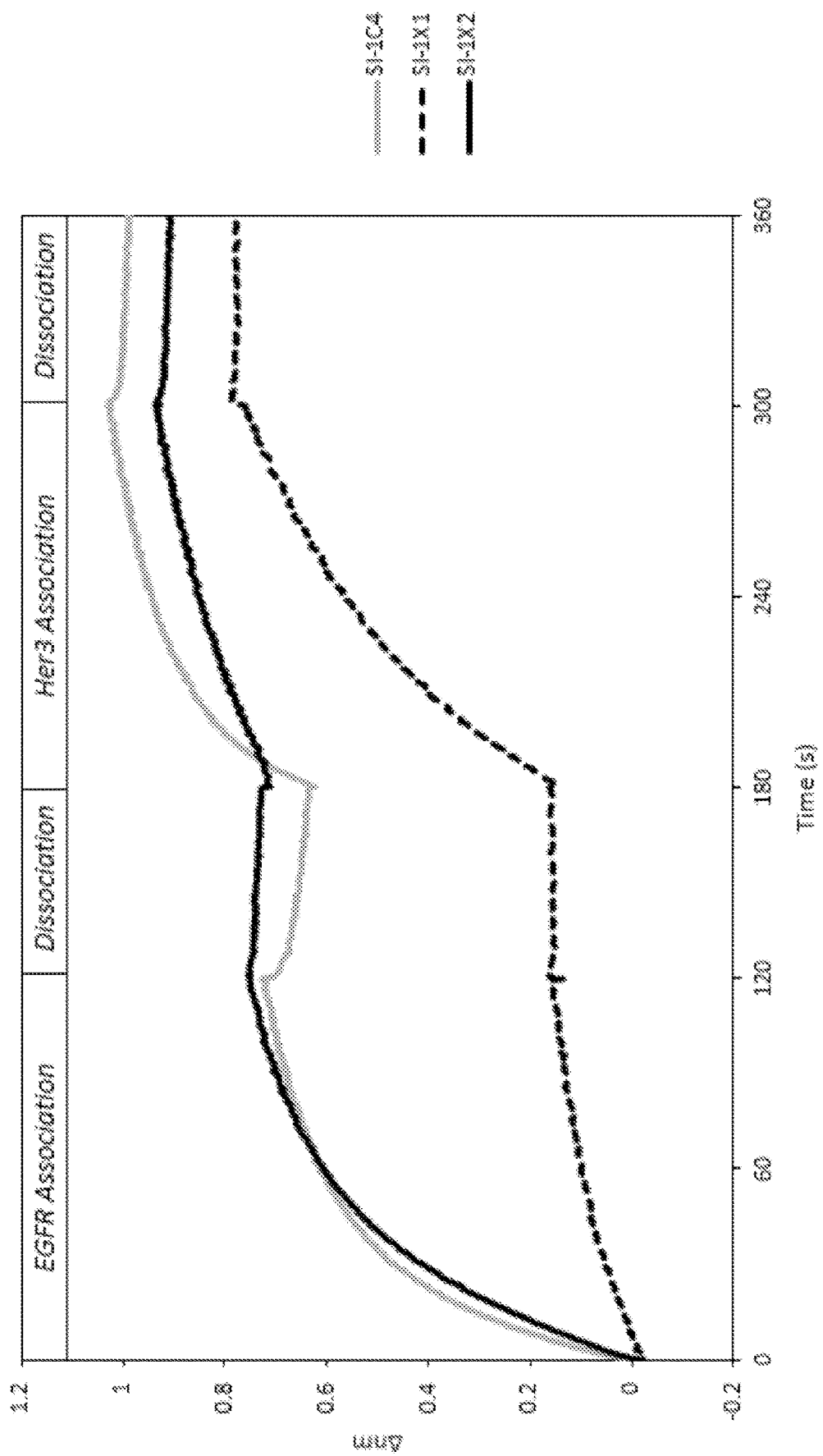
FIGS. 7, 8, and 9 are graphs showing bispecific ELI binding.
Figure 8:
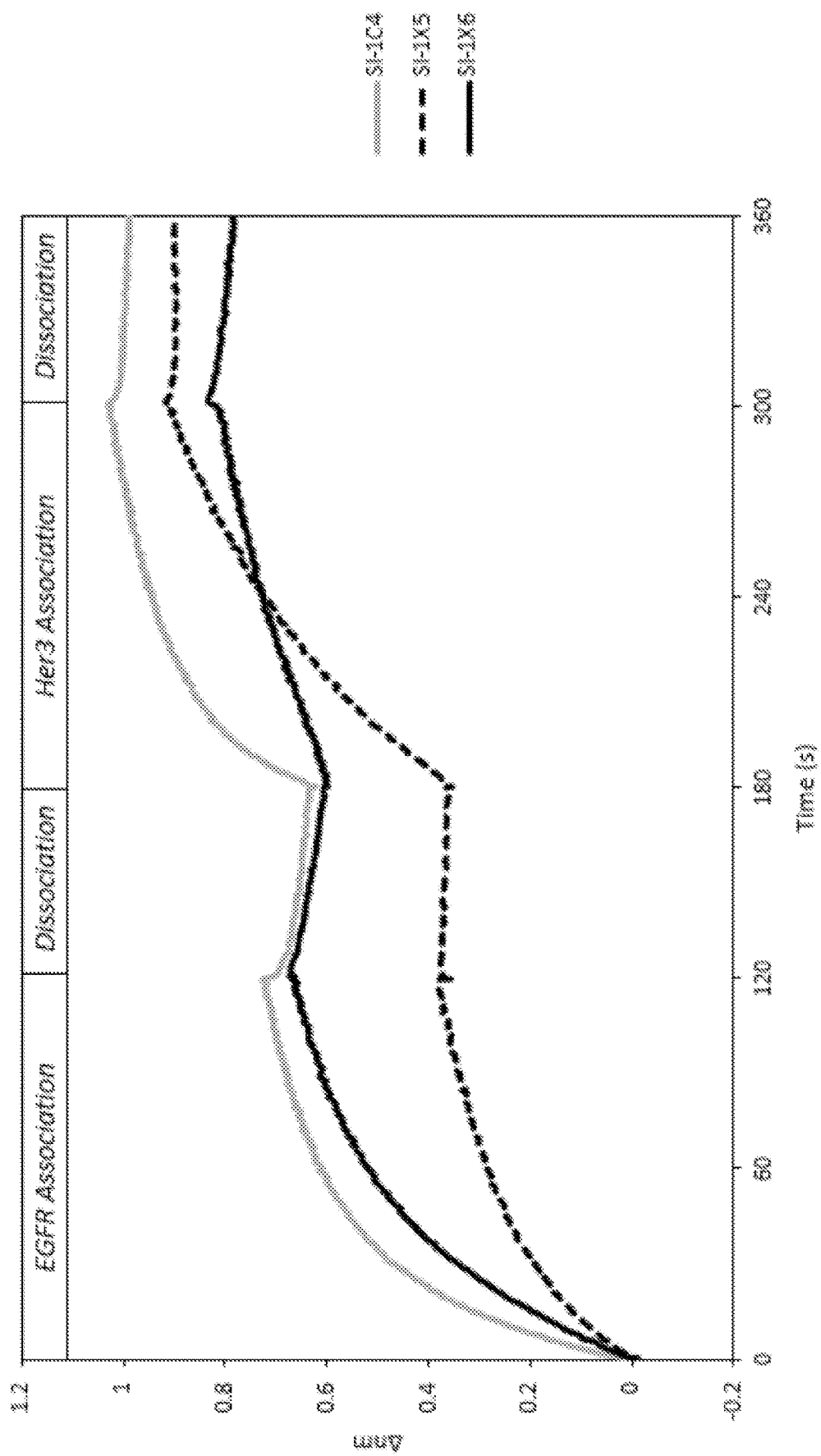

SI-1X4.2 is a modification of SI-1X4 molecule and contained 5 amino acid changes as follows: V71A, T75S, N76S, A93T and S107T using the Kabat numbering system. Some of these changes especially positions 75, 76 and 93 potentially made interaction with antigen even though these are not in the CDR loops and are essential for binding and activity. FIG. 4 shows the 5 amino acid differences between SI-1X4.2 and SI-1X4.

Example 2

Characterization of Antibodies Against Epidermal Growth Factor Receptor Using BLI Monomeric EGFR extracellular domain binding was measured in a biolayer interferometry (BLI) binding assay on a BLItz instrument (ForteBio, Inc.). 25 µg/mL of SI-1C3, SI-1C4, SI-1C6, SI-1X1, SI-1X2, SI-1X5, and SI-1X6 were diluted in PBS and captured on anti-huIgG Fc BLItz biosensor tips for 120 seconds. Tips were washed for 30 seconds in PBS and moved to an EGFR (ProSpec Bio, PKA-344) sample for binding at 588 nM. Binding of EGFR ECD to the tips was recorded as biolayer interferometry signals (Δnm) over an association time of 120 seconds. Tips were moved to PBS and dissociation was observed for 240 seconds (*SI-1C6 dissociation time of only 120 seconds observed). FIGS. 5 and 6 report data starting at the association step of EGFR to the antibody-loaded biosensor. Each Figure shows comparison to SI-1C4 as a benchmark antibody.

Since SI-1C3 and SI-1X2 share their EGFR binding domain displayed as a Fab, their binding profiles are similar and stronger than the scFv form displayed on SI-1X1 (FIG. 6). Each has a very slow off-rate to EGFR compared to SI-1C4 and is not affected by their on-rate. SI-1X1 may show weaker on-rate binding to EGFR, but stays bound very strongly. The same trend is observed in FIG. 5, where the Fab versions of the EGFR binding domains displayed on SI-1C6 and SI-1X6 bind at a faster rate than their representative scFv displayed on SI-1X5. Having the EGFR binding domain on the Fab side of the bispecifics antibody appears to bind with faster on-rates than the scFv versions, yet exhibit similar off-rates. SI-1X3 and SI-1X4 do not exhibit monomeric EGFR binding in this assay (data not shown) and dimeric EGFR binding is investigated in an ELISA below.

Example 3

Characterization of Antibodies Against EGFR and Her3 Using BL1

Bispecific binding to EGFR and Her3 extracellular domains was measured in a biolayer interferometry (BLI) binding assay on a BLItz instrument (ForteBio, Inc.). 200 nM of SI-1C1, SI-1C3, SI-1C4, SI-1C6, SI-1X1, SI-1X2, SI-1X3, SI-1X4, SI-1X5, and SI-1X6 were diluted in 1× Kinetics Buffer (ForteBio, Inc.) and captured on anti-huIgG Fc BLItz biosensor tips for 120 seconds. Tips were washed in KB for 30 seconds and moved to an EGFR sample (ProSpec Bio, PKA-344) for binding at 200 nM. Binding of EGFR ECD to the tips was recorded as biolayer interferometry signals (Δnm) over an association time of 120 seconds. Tips were moved to KB and dissociation was observed for 60 seconds. The process was repeated with Her3 ECD sample (Sino Biological, 10201-H08H-10) at 200 nM for 120 seconds and a similar dissociation step of 60 seconds in KB. FIGS. 8-10 7-9 report data starting at the association step of EGFR to the antibody-loaded biosensor. Antibodies are able to exhibit simultaneous bispecific binding of EGFR and Her3 while being bound by the Fc to the sensor. As observed in FIG. 7 and FIG. 8, the display of the EGFR binding domain as Fab (SI-1X2, SI-1X6) has stronger on-rate binding than their scFv forms (SI-1X1, SI-1X5, respectively). Here, both EGFR and Her3 exhibit the same Fab>>scFv on-rate trend. SI-1X3 and SI-1X4 do not exhibit binding to monomeric EGFR, however each has the ability to bind Her3, as expected since each molecule uses the same αHer3 binding domain as SI-1X1, SI-1X2, SI-1X5, and SI-1X6. SI-1X3 and SI-1X4 are investigated for dimeric EGFR binding in an ELISA below.

Example 4

Dimeric EGFR ELISA Assay

Figure 9:
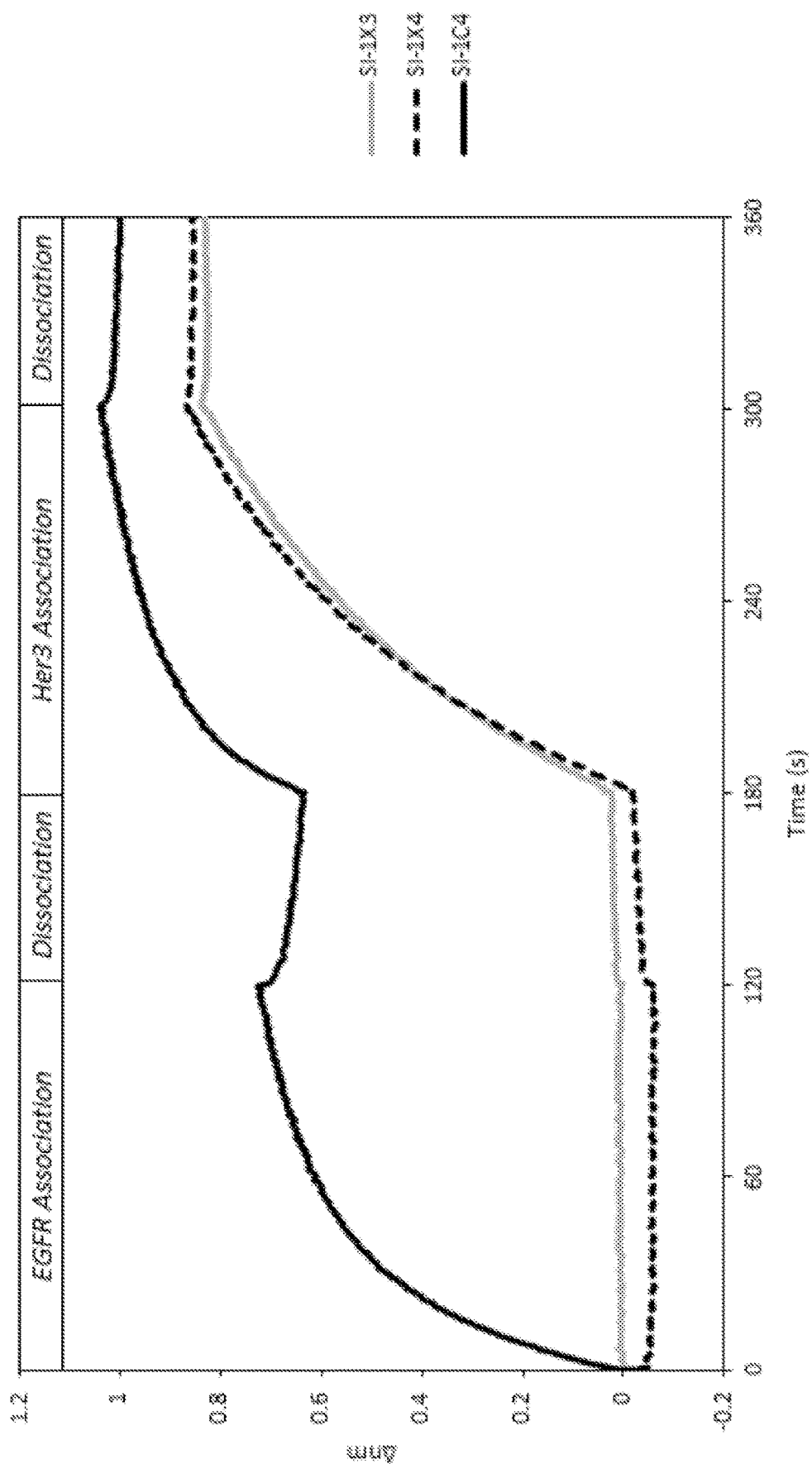

As observed earlier, SI-1X3 and SI-1X4 were unable to bind a monomeric form of EGFR in a BLI assay (FIG. 9). It has been suggested that in order for the αEGFR binding domain used in SI-1C5, SI-1X3, and SI-1X4 to bind to EGFR in vitro, bivalent binding is required (Perez et al, *Chin Clin Oncol* 2014;3(1):5). To observe this, we utilized ELISA for antibody binding relative to other EGFR binding antibodies using a dimeric form of EGFR.

Figure 10:
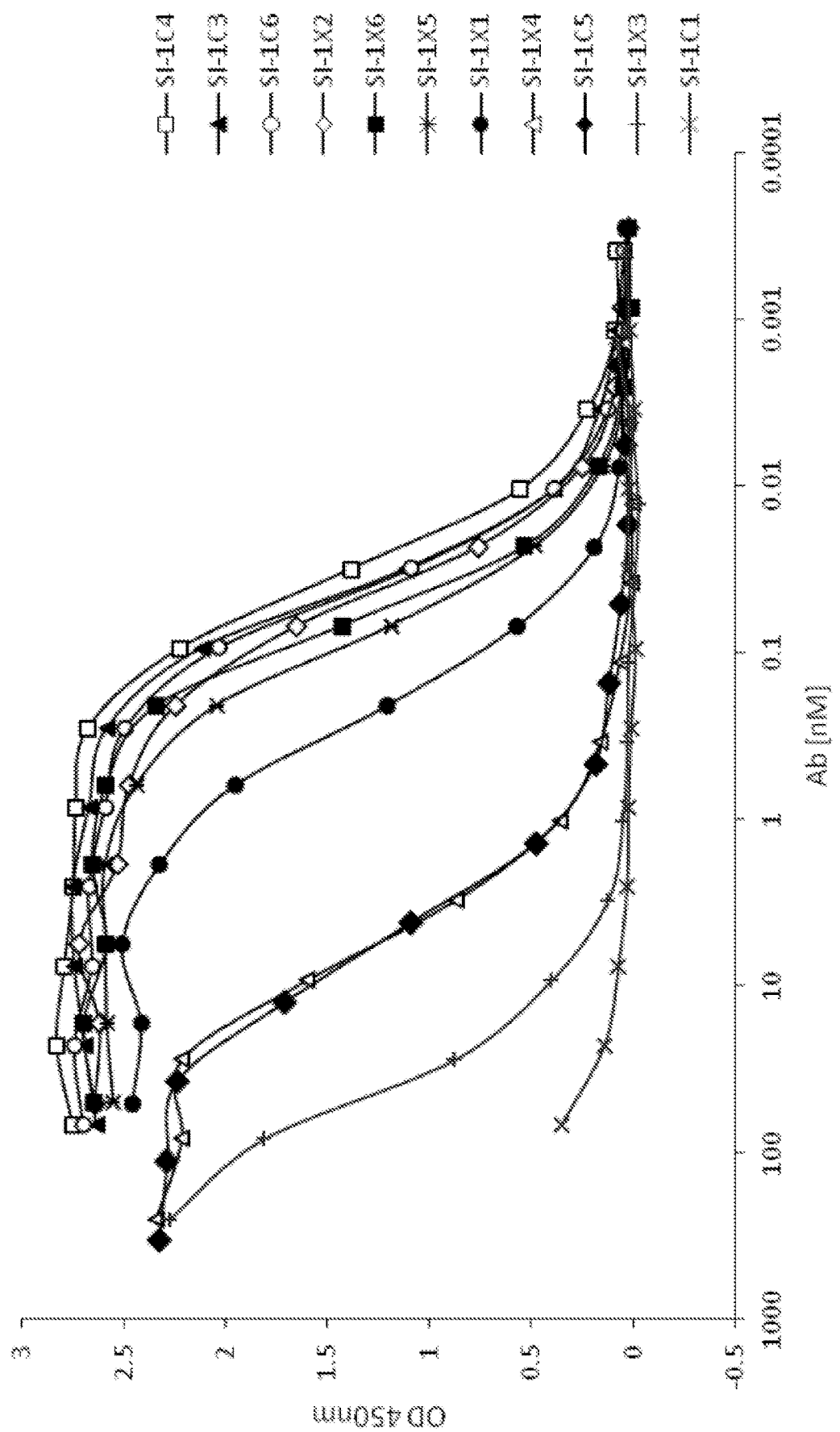
FIG. 10 is a graph showing dimeric EGFR ELISA.

ELISA was performed using dimeric EGFR ECD reagent, SI-2C1, fused to rabbit Fc created in house. EGFR was coated onto Maxisorp immunoplates (Nunc) at 3 µg/mL in PBS at 4° C. overnight. Plates were blocked in PBS with 3% BSA and 0.05% Tween20 for 2 hours at room temperature. Antibodies were captured at starting at 10 ug/mL except for SI-1C5, SI-1X3, and SI-1X4 which started at 50 µg/mL for (reported in nM), all with 3× dilutions in PBST (1% BSA) for 1 hour at room temperature. Goat αhuman IgG-HRP antibody (Jackson ImmunoResearch, 109-035-098) was used for detection of the Fc portion of the antibodies at 1:2000 dilution in PBST (1% BSA) and developed in TMB (Thermo Scientific) for 5 minutes with 2 M $H_2SO_4$ as a stop solution. 3 washes with PBST (1% BSA) were performed between each step. All data points were performed in triplicate and collected at 450 nm (FIG. 10). SI-1C5, SI-1X3, and SI-1X4 all bound to the dimeric EGFR ECD in this ELISA format at high concentrations as compared to the other molecules.

Example 5

Binding Kinetics of 1C5.2 and 1X4.2 Using Octet

Figure 11:
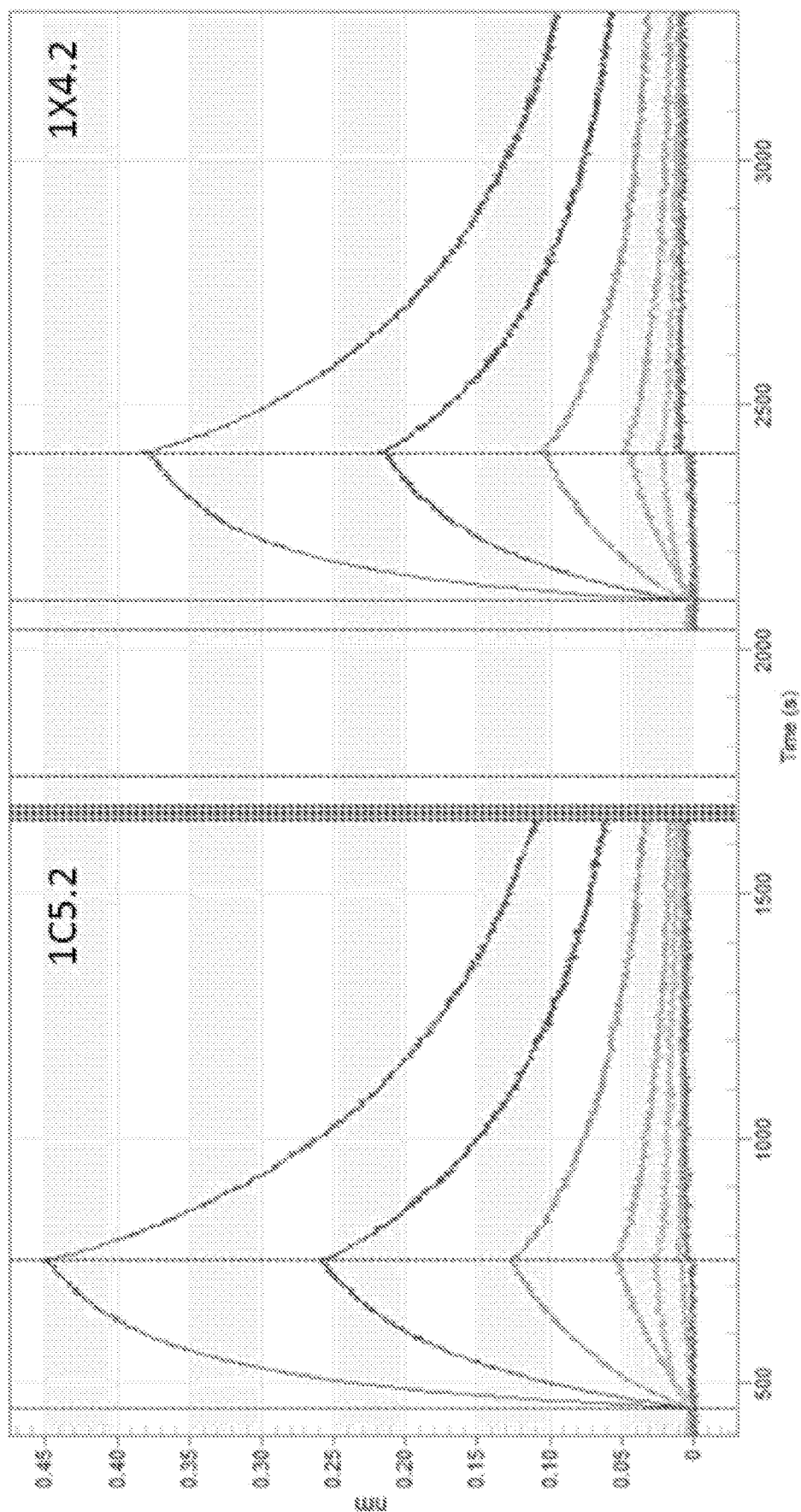
FIG. 11 shows binding kinetics of SI-1C5.2 and SI-1X4.2 with monomeric EGFR as analyzed by Octet.

Kinetics determined using ForteBio Octet Red96 instrument with anti-human Fc sensors (ForteBio, AHC #18-5060). Binding experiments performed at 30° C. with 1000 RPM mixing. EGFR protein is extracellular domain (Met 1-Ser 645) of human EGFR with a C-terminal polyhistidine tag. All samples diluted in 10× Kinetics Buffer (ForteBio #18-5032). 1C5.2, 1X6 and 1X4.2 were loaded onto 8 sensors at 10 µg/ml each for 300 seconds followed by a Baseline for 60 seconds in 10× Kinetics Buffer. Association with EGFR protein was performed for 300 seconds with each sensor in a single concentration of EGFR protein (300, 100, 33.33, 11.11, 3.705, 1.235, 0.4116 and 0 nM). Dissociation was then performed in 10× Kinetics Buffer for 900 seconds. A typical association and dissociation trace for 1C5.2 and 1X4.2 is shown in FIG. 11.

Data analysis was performed using ForteBio Data Analysis Software v9.0. Software curve-fitting was performed and the four most optimal curve fits for each 1C5.2 (TABLE 2), 1X4.2 (TABLE 3) and 1X6 (TABLE 4) were used and averaged to determine KD, k(on) and k(dis). The average KD for SI-1C5.2 and SI-1X4.2 were 19.2 nM and 18.4 nM respectively. The average KD for SI-1C6 was 3.04 nM 1C5.2 and 1X4.2 contained five amino acid changes as compared to 1C5 and 1X4 as described in example 1. These changes accounted for improved binding to EGFR ECD when compared to data generated for 1C5 and 1X4 in FIG. 10.

TABLE 2

Summary of KD, KON and KDIS for 1C5.2

|          | EGFR (NM) | KD (M)   | KON (1/MS) | KDIS (1/S) |
|----------|-----------|----------|------------|------------|
| SI-1C5.2 | 300       | 3.74E-08 | 4.61E+04   | 1.72E-03   |
| SI-1C5.2 | 100       | 2.23E-08 | 7.89E+04   | 1.76E-03   |
| SI-1C5.2 | 33.3      | 9.94E-09 | 1.60E+05   | 1.59E-03   |
| SI-1C5.2 | 11.1      | 7.08E-09 | 2.12E+05   | 1.50E-03   |
| AVERAGES |           | 1.92E-08 | 1.24E+05   | 1.64E-03   |

TABLE 3

Summary of KD, KON and KDIS for 1X4.2

|          | EGFR (NM) | KD (M)   | KON (1/MS) | KDIS (1/S) |
|----------|-----------|----------|------------|------------|
| SI-1X4.2 | 300       | 3.69E-08 | 4.63E+04   | 1.71E-03   |
| SI-1X4.2 | 100       | 2.10E-08 | 7.88E+04   | 1.65E-03   |
| SI-1X4.2 | 33.3      | 9.44E-09 | 1.58E+05   | 1.49E-03   |
| SI-1X4.2 | 11.1      | 6.19E-09 | 2.18E+05   | 1.35E-03   |
| AVERAGES |           | 1.84E-08 | 1.25E+05   | 1.55E-03   |

TABLE 4

Summary of KD, KON and KDIS for 1X6

|          | EGFR (NM) | KD (M)   | KON (1/MS) | KDIS (1/S) |
|----------|-----------|----------|------------|------------|
| SI-1C6   | 300       | 3.04E-09 | 4.11E+05   | 1.25E-03   |
| SI-1C6   | 100       | 3.04E-09 | 4.11E+05   | 1.25E-03   |
| SI-1C6   | 33.3      | 3.04E-09 | 4.11E+05   | 1.25E-03   |
| SI-1C6   | 11.1      | 3.04E-09 | 4.11E+05   | 1.25E-03   |
| AVERAGES |           | 3.04E-09 | 4.11E+05   | 1.25E-03   |

Example 6

Binding Tests of Example Bispecific Antibodies to Tumor Cell Lines

Figure 12:
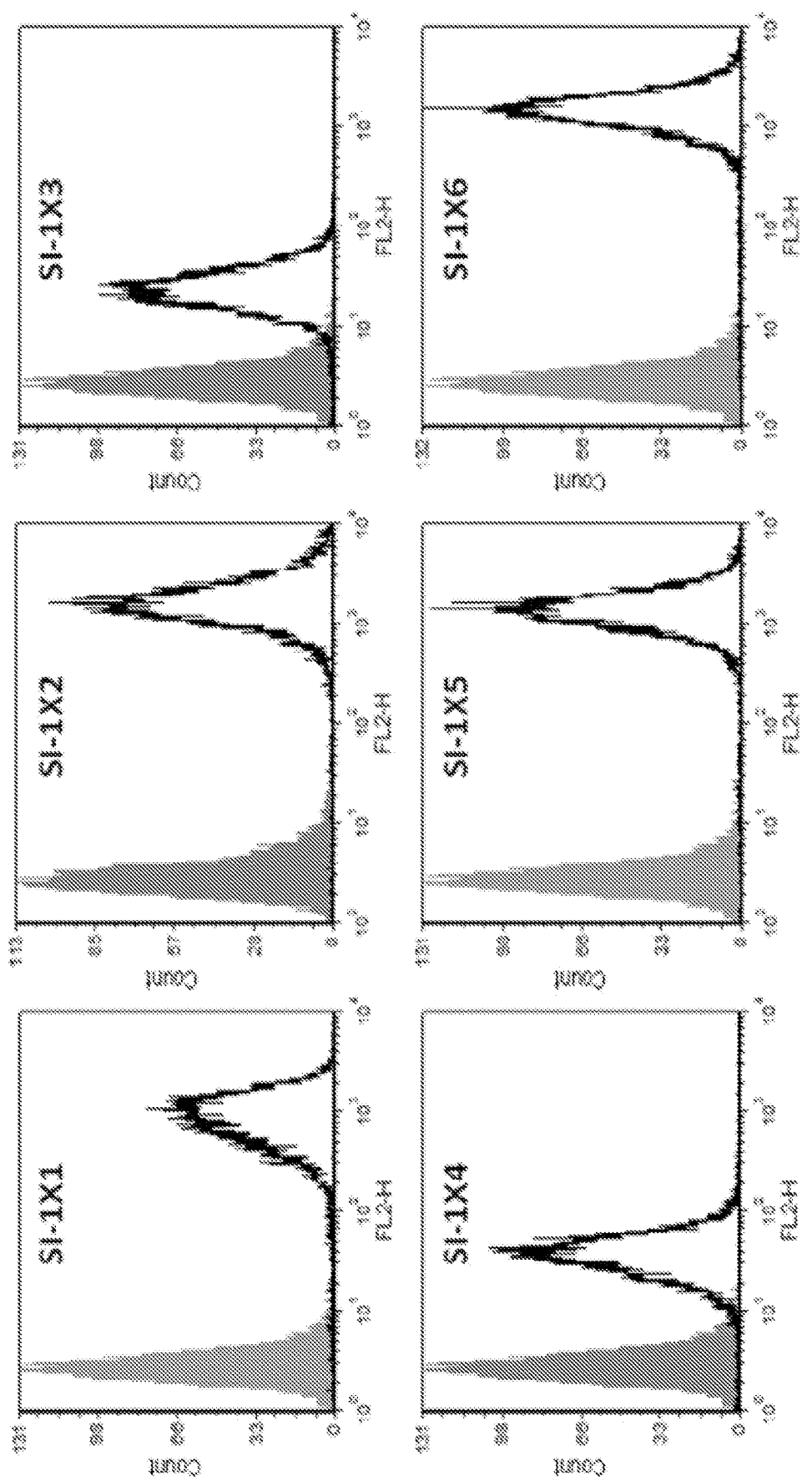
FIG. 12 shows flow cytometric analysis of SI-1X antibodies binding to A431 cells.
Figure 13:
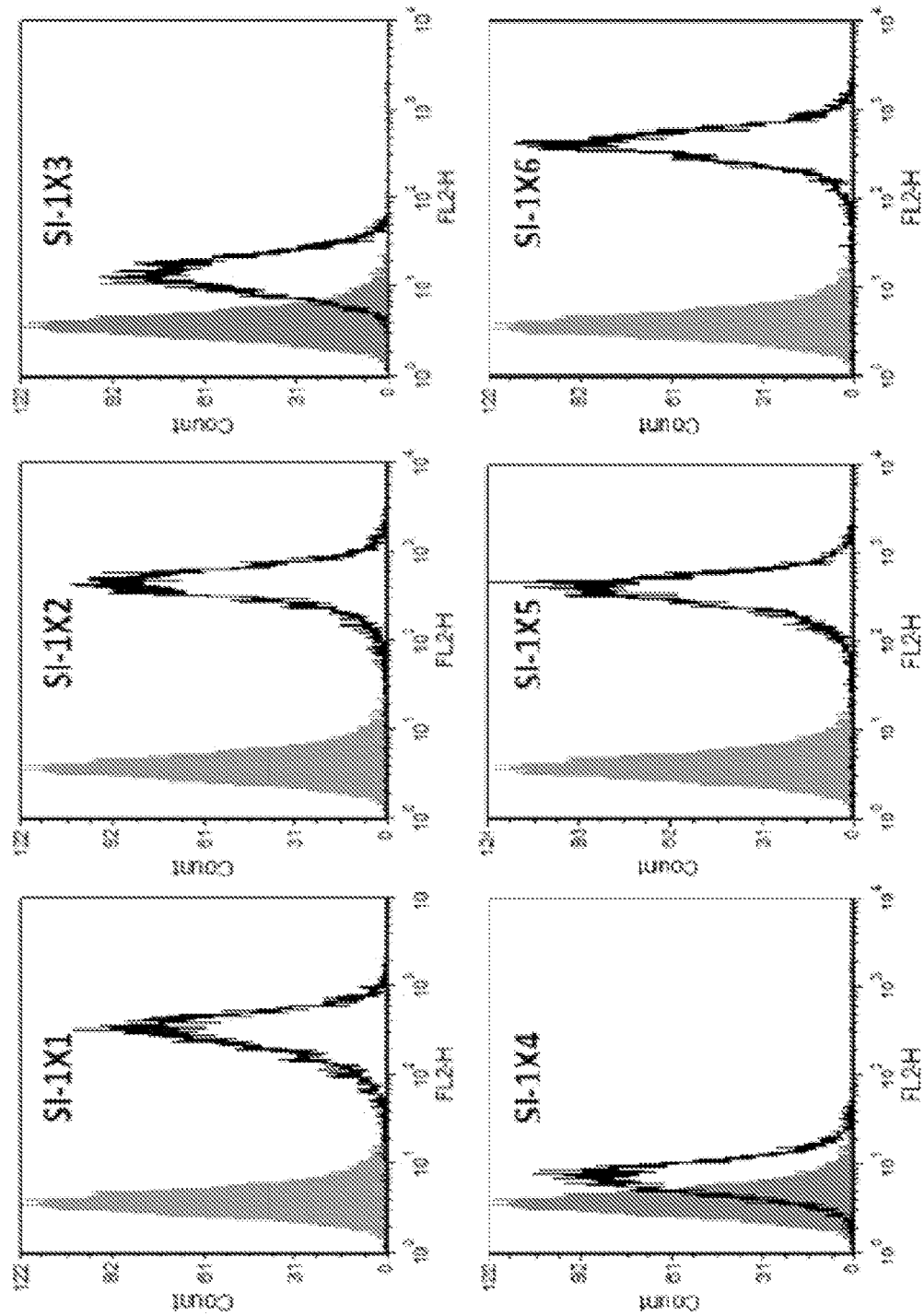
FIG. 13 shows flow cytometric analysis of SI-1X antibodies binding to BxPC3 cells.

The bispecific antibodies SI-1X1, SI-1X2, SI-1X3, SI-1X4, SI-1X5, and SI-1X6, as well as an isotype control were tested for binding to the tumor cell lines, A431 (epidermoid carcinoma, ATCC CRL-1555) and BxPC3 (pancreatic adenocarcinoma, ATCC CRL-1687) by flow cytometry. Cells were grown in RPMI-1640 medium containing 10% fetal bovine serum and were harvested for analysis while in exponential growth phase. Aliquots of $5 \times 10^6$ cells were washed once in PBS, then resuspended in 250 µl of PBS+1% bovine serum albumin (BSA) and incubated at 4° C. for 15 minutes to block membranes from non-specific binding. 250 µl of antibody, diluted to 10 µg/ml in PBS/1% BSA, was added to each sample for a final antibody concentration of 5 µg/ml. Cells were incubated in primary antibody for 1 hour at 4° C. with mixing. Cells were then washed twice with 1 ml PBS/1% BSA and then resuspended in 500 µl of PE-conjugated mouse-anti-human IgG-Fc and incubated at 4° C. with mixing for 45 minutes. Samples were again washed twice with 1 ml PBS/1% BSA, resuspended in 300 ml PBS and analyzed using a FACScalibur flow cytometer. For each sample, 10000 events were collected in the FL-2 channel. Histograms were generated using FCS Express software and SI-1X histograms were overlaid with histograms from the isotype control staining. All six bispecific antibodies displayed histogram shifts with respect to control staining indicating cell binding. This data is displayed in FIG. 12 (A431 cell binding) and FIG. 13 (BxPC3 cell binding).

Example 7

Characterization of SI-1C5.2 and SI-1X4.2 by Cell Binding Assays

Figure 14:
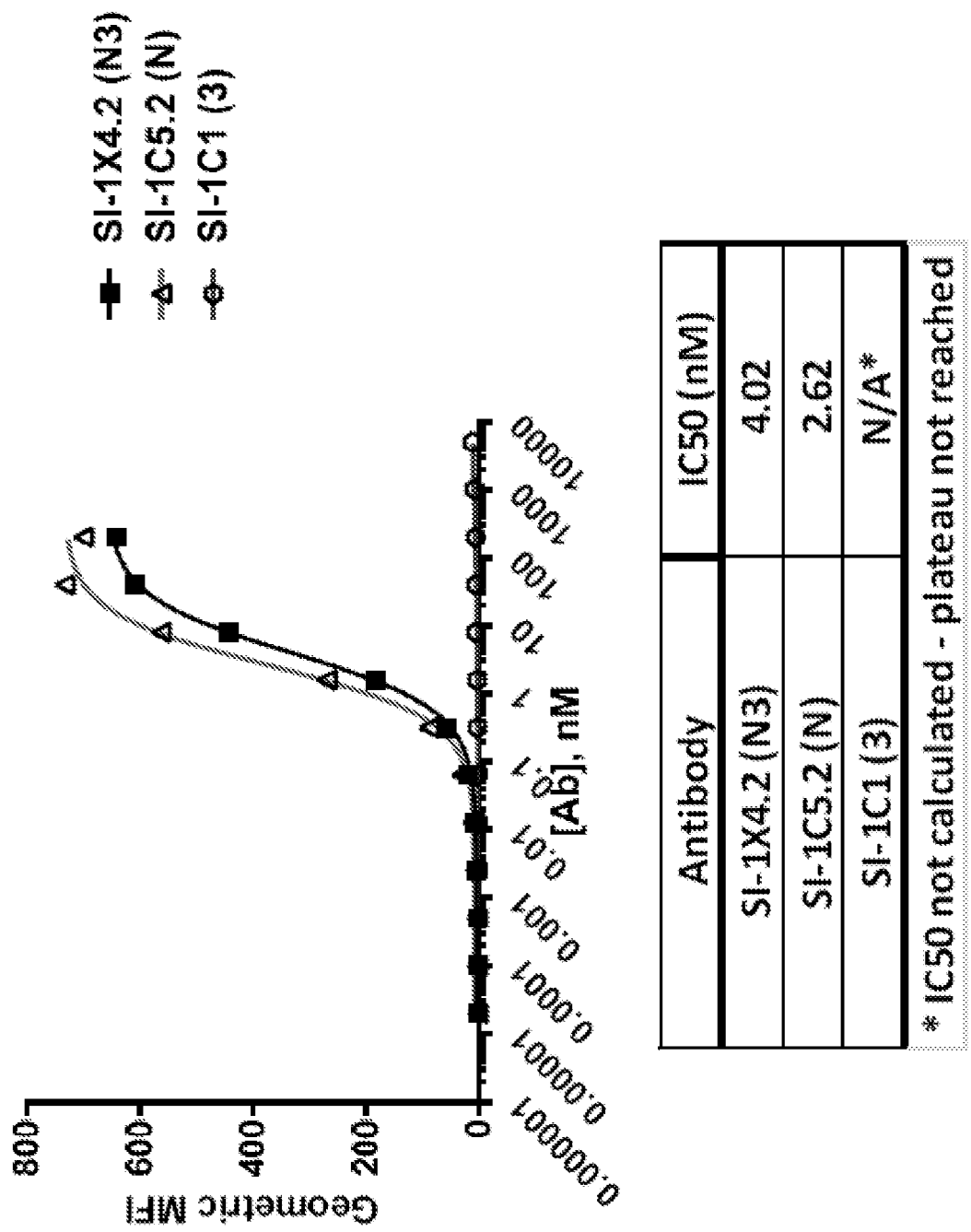
FIG. 14 shows flow cytometric analysis of SI-1X4.2 antibody binding to Fadu cells.
Figure 15:
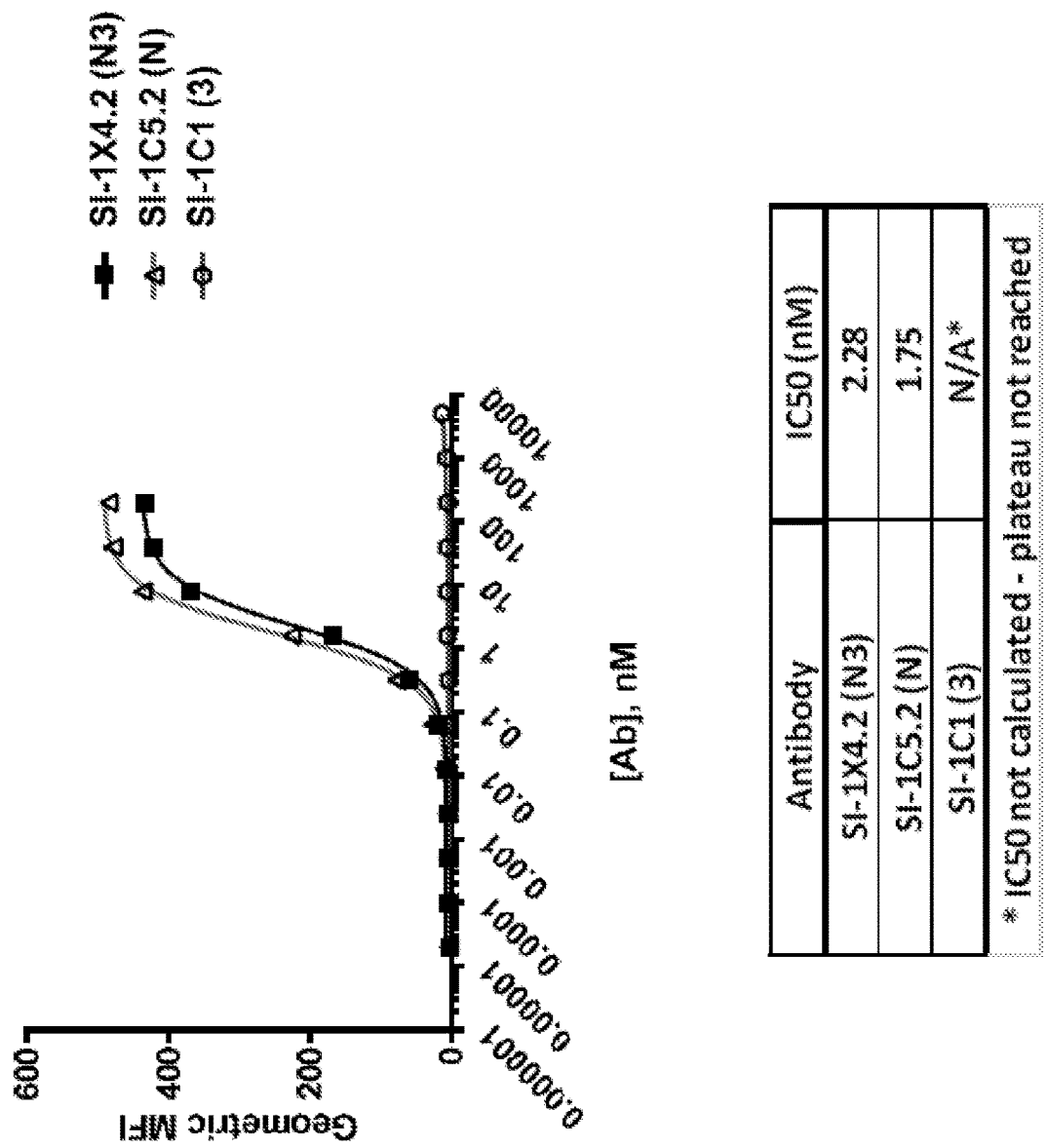
FIG. 15 shows flow cytometric analysis of SI-1X4.2 antibody binding to A431 cells.

The bispecific antibody, SI-1X4.2, monospecific antibodies, SI-1C5.2 and SI-1C1, as well as an isotype control were tested for binding to the tumor cell lines, A431 (epidermoid carcinoma, ATCC CRL-1555) (FIG. 14) and FaDu (hypopharyngeal squamous cell carcinoma, ATCC HTB-43) (FIG. 15) by flow cytometry. Cells were grown in RPMI-1640 medium containing 10% fetal bovine serum and were harvested for analysis while in exponential growth phase. Cells were washed once in PBS, then resuspended in PBS+5% fetal bovine serum albumin (FBS) at a concentration of $5 \times 10^6$ cells/ml and incubated at 4° C. for 15 minutes to block membranes from non-specific binding. 100 µl aliquots of cells were added to 100 µl aliquots of antibody (also diluted in PBS+5% FBS) in a 96-well plate. Samples were incubated in primary antibody for 45 minutes on ice. Cells were then washed twice with 200 µl of PBS+5% FBS and then resuspended in 100 µl of PE-conjugated mouse-anti-human IgG-Fc and incubated on ice 30 minutes. Samples were again washed twice with 200 µl of PBS+5% FBS, resuspended in 200 µl PBS and analyzed using a FACScalibur flow cytometer. For each sample, 10000 events were collected in the FL-2 channel. Histograms were analyzed using FCS Express software and the geometric mean fluorescence intensity (GMFI) was determined for each data set. EC50 binding values were determined by plotting the GMFI versus antibody concentration using Graphpad Prism software. The bispecific antibody, SI-1X4.2 displayed similar binding profile as the monospecific anti-EGFR antibody, SI-1C5.2 with similar EC50 in both cell lines. The other monospecific anti-Her3 antibody, SI-1C1 binds weakly to the two cell lines probably due to low level of expression of Her3 on the surface of the cells. 1C5.2 and 1X4.2 contained five amino acid changes as compared to 1C5 and 1X4 as described in example 1. These changes accounted for improved binding to target cells when compared to the parental molecule, 1X4.

Example 8

Anti-Proliferative Effect of SI-1X Antibodies on Tumor Cell Lines

To assess the growth inhibitory potential of anti-Her3/EGFR bispecific antibodies, the effect on proliferation of A431 cells (ATCC CRL-1555, Manassas, Va.) which are an epidermoid carcinoma tumor line was tested. The effect on proliferation of BxPC3 (ATCC CRL-1687, Manassas, Va.), a pancreatic adenocarcinoma tumor line was also tested. For each line, cells were seeded into 96-well tissue culture plates at a density of 6000 cells/well in 100 µl RPMI-1640 medium containing 1% fetal bovine serum. After 4 hours, test antibodies were added at various concentrations, ranging from 0.0015 nM to 100 nM. Cells were cultured in the presence of test antibodies for 72 hours. To each well, 20 µl of MTS reagent (Promega, Madison, Wis.) was added and cells were incubated at 37° C. for 2 hours. MTS is readily taken up by actively proliferating cells, reduced into formazan (which readily absorbs light at 490 nm), and then secreted into the culture medium. Following incubation, OD490 values were measured using a BioTek (Winooski, Vt.) ELx800 absorbance reader. OD490 values for control cells (treated with medium only) were also obtained in this manner at the time of antibody addition in order to establish baseline metabolic activity. Proliferation may be calculated by subtracting the control baseline OD490 from the 72 hour OD490. Data from antibody titrations was expressed at % of control population according to the following formula: % of control proliferation=(test proliferation/control proliferation)*100.

Figure 16:
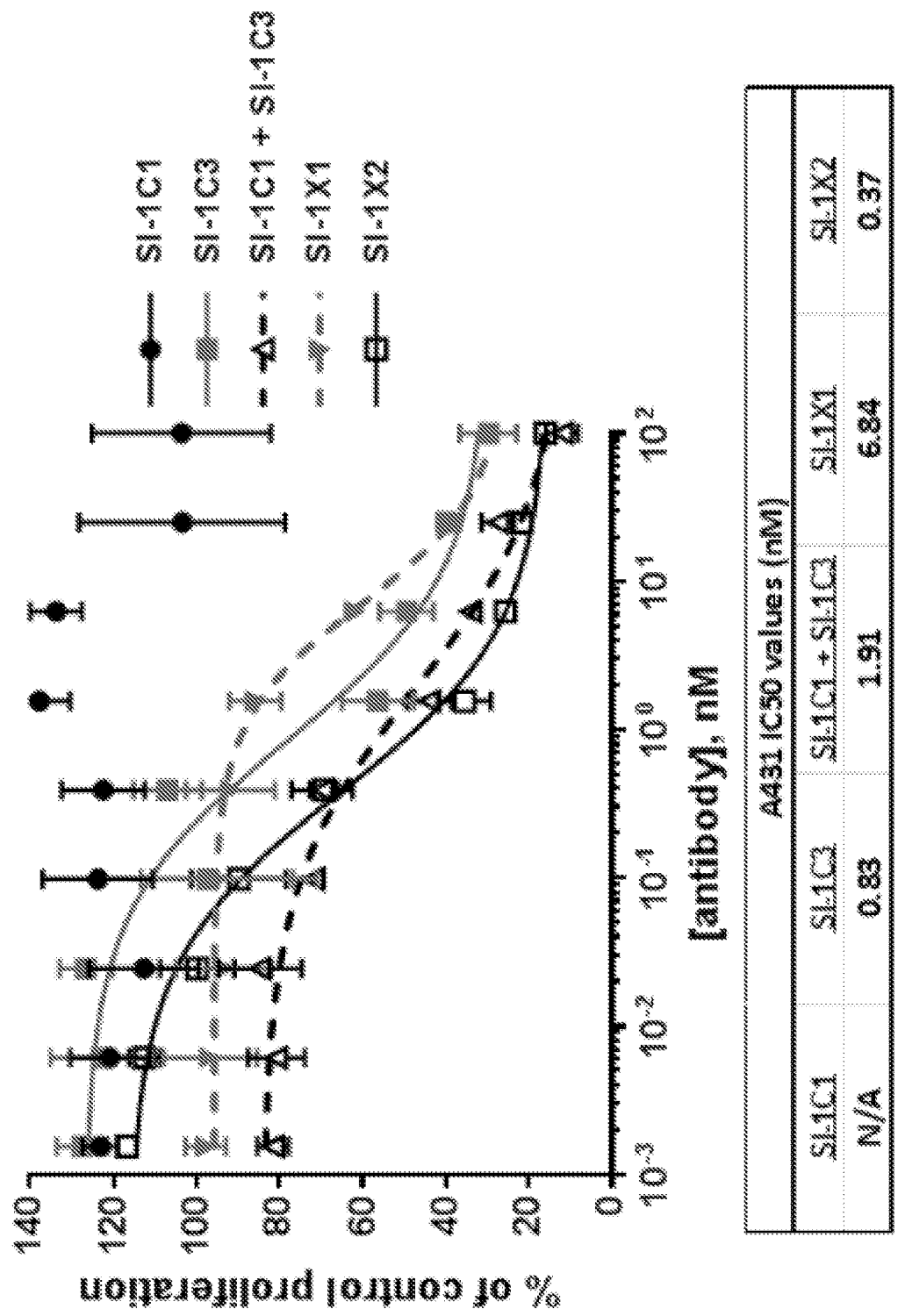
FIG. 16 shows effect of SI-1X antibodies on A431 cell proliferation.
Figure 17:
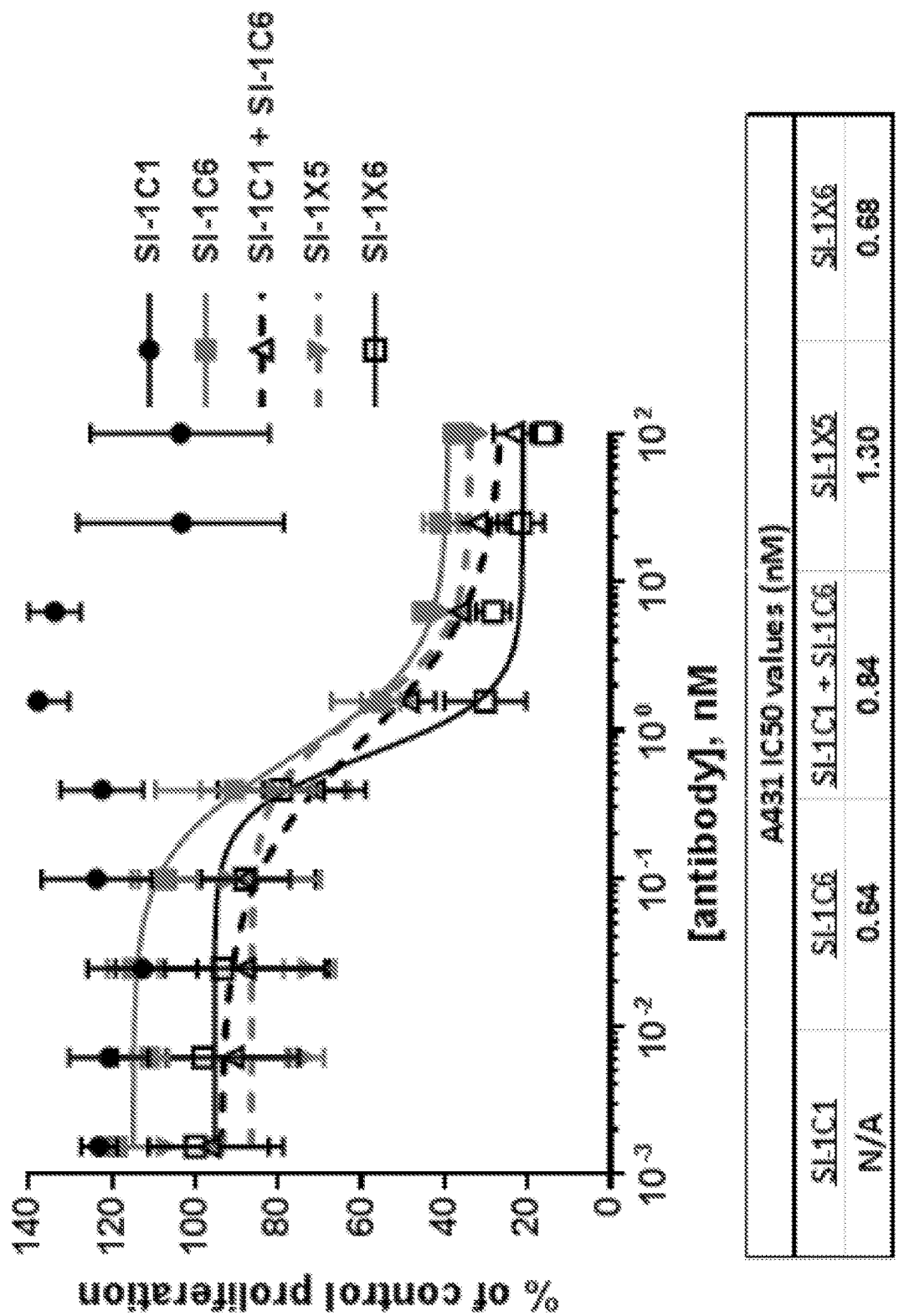
FIG. 17 shows effect of SI-1X antibodies on A431 cell proliferation.

The effects of various bispecific anti-Her3/anti-EGFR antibodies on A431 cell proliferation are shown in FIG. 16 and FIG. 17. SI-1X2 demonstrated more efficacious antiproliferative effect than the control antibodies SI-1C1 (anti-Her3), SI-1C3 (anti-EGFR), or SI-1C1 and SI-1C3 applied together. SI-1X1 exhibited antiproliferative effects, although not to the degree seen with SI-1C3 and the combination of SI-1C1 and SI-1C3. Inhibition plots as well as IC50 values are shown in FIG. 17. Similar results were observed for SI-1X5 and SI-1X6, where SI-1X6 is more potent than SI-1X5 and the control antibody SI-1C1 (anti-Her3), however it displayed similar antiproliferative potential as the control antibody SI-1C6 (anti-EGFR) and the combination of SI-1C1 and SI-1C6. This may be seen along with IC50 values in FIG. 17.

Figure 18:
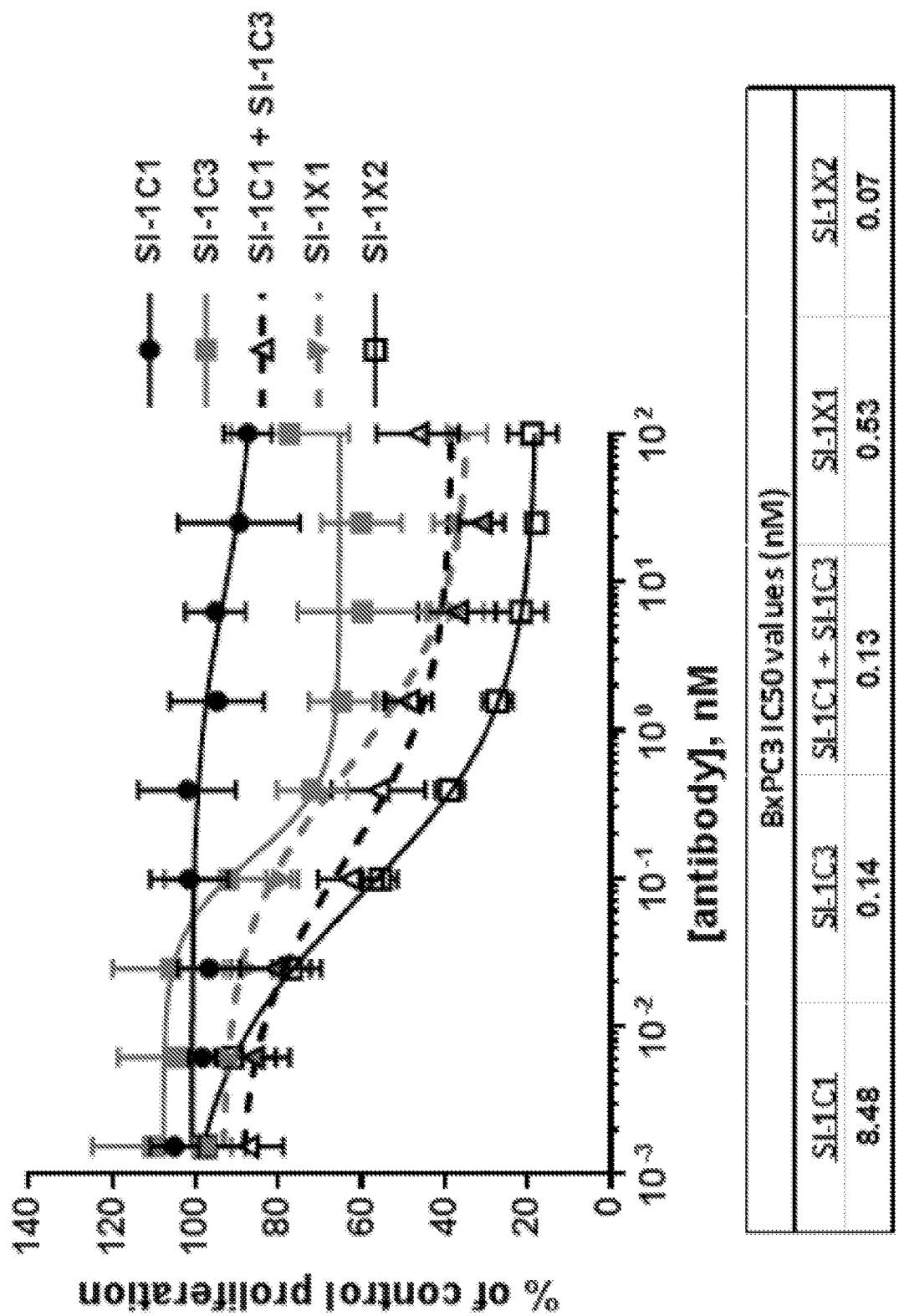
FIG. 18 shows effect of SI-1X antibodies on BxPC3 cell proliferation.
Figure 19:
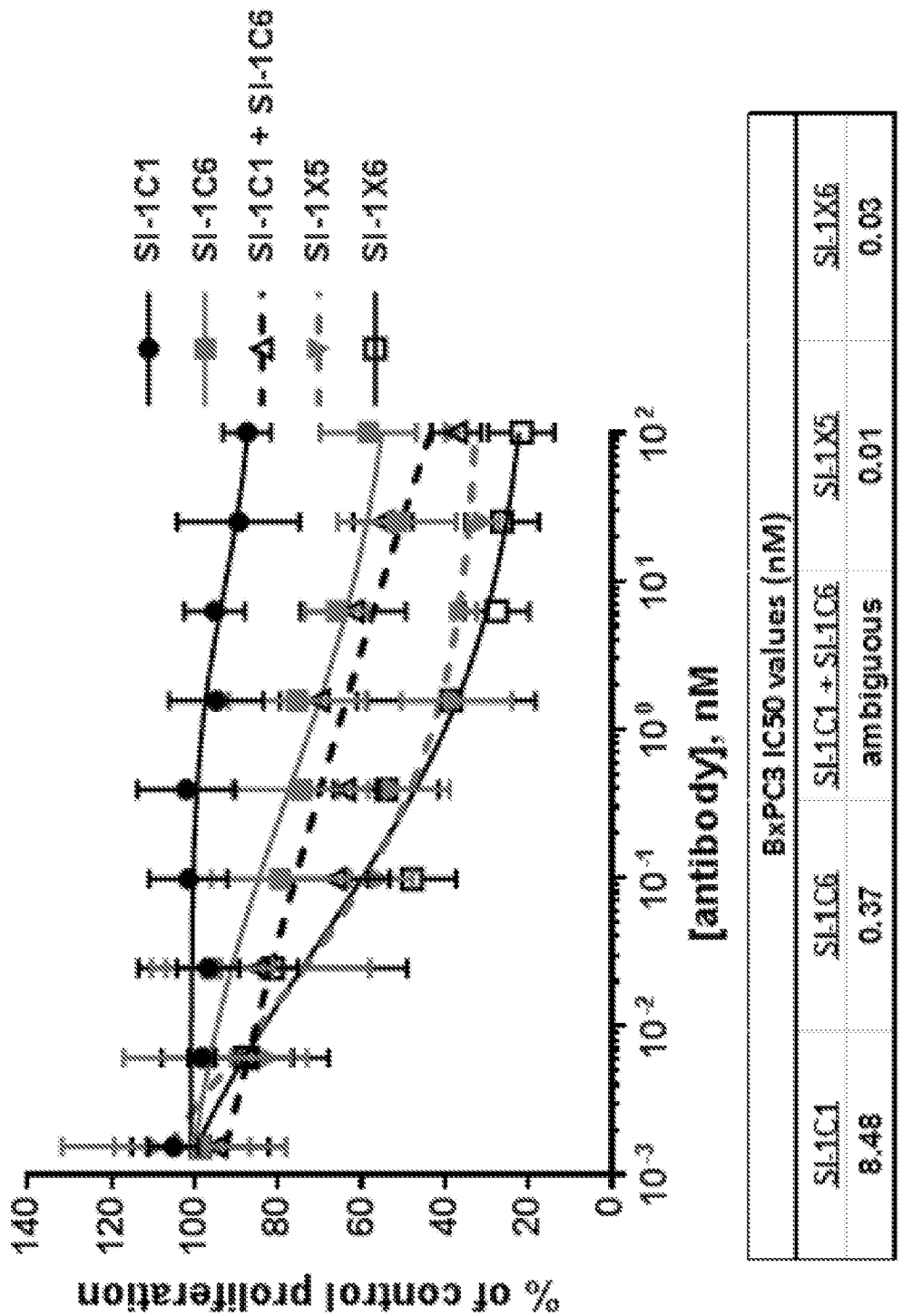
FIG. 19 shows effect of SI-1X antibodies on BxPC3 cell proliferation.

These molecules were also tested for antiproliferative effects in the BxPC3 cell line (FIG. 18 and FIG. 19). Again, SI-1X2 demonstrated more efficacious antiproliferative effect than the control antibodies SI-1C1 (anti-Her3), SI-1C3 (anti-EGFR), or SI-1C1 and SI-1C3 applied together. SI-1X1 was more efficacious than SI-1C1, but weaker than SI-1C3 and the combination of SI-1C1 and SI-1C3. Inhibition curves and IC50 values are displayed in FIG. 19. BxPC3 proliferation was more strongly inhibited by both SI-1X5 and SI-1X6 than with the control antibodies SI-1C1 (anti-Her3), SI-1C6 (anti-EGFR), or SI-1C1 and SI-1C6 in combination. This data along with IC50 values is shown in FIG. 19.

Example 9

Anti-Proliferative Effect of SI-1C5.2 and SI-1X4.2 on Tumor Cell Lines

To assess the growth inhibitory potential of anti-Her3/EGFR bispecific antibodies, the effect on proliferation of FaDu (nasopharyngeal squamous cell carcinoma line, ATCC HTB-43) and A431 (epidermoid carcinoma, ATCC CRL-1555) cells were tested. Cells were seeded into 96-well tissue culture plates at a density of 6000 cells/well in 100 µl RPMI-1640 medium containing 1% fetal bovine serum. After 4 hours, test antibodies were added at various concentrations, ranging from 0.0015 nM to 100 nM. Cells were cultured in the presence of test antibodies for 72 hours. To each well, 11 µl of alamar blue reagent (Thermo Scientific) was added and cells were incubated at 37° C. for 2 hours. Alamar blue is readily taken up by actively proliferating cells, reduced, and then secreted into the culture medium. The reduced form of alamar blue is strongly fluorescent. Following incubation, fluorescence was measured using a Molecular Devices (Sunnyvale, Calif.) FilterMax F5 multimode plate reader using an excitation wavelength of 535 nm and an emission wavelength of 595 nm. Fluorescence values for control cells (treated with medium only) were also obtained in this manner at the time of antibody addition in order to establish baseline metabolic activity. Proliferation may be calculated by subtracting the control baseline fluorescence from the 72-hour fluorescence values. Data from antibody titrations was expressed at % of control population according to the following formula: % of control proliferation=(test proliferation/control proliferation)*100.

Figure 20:
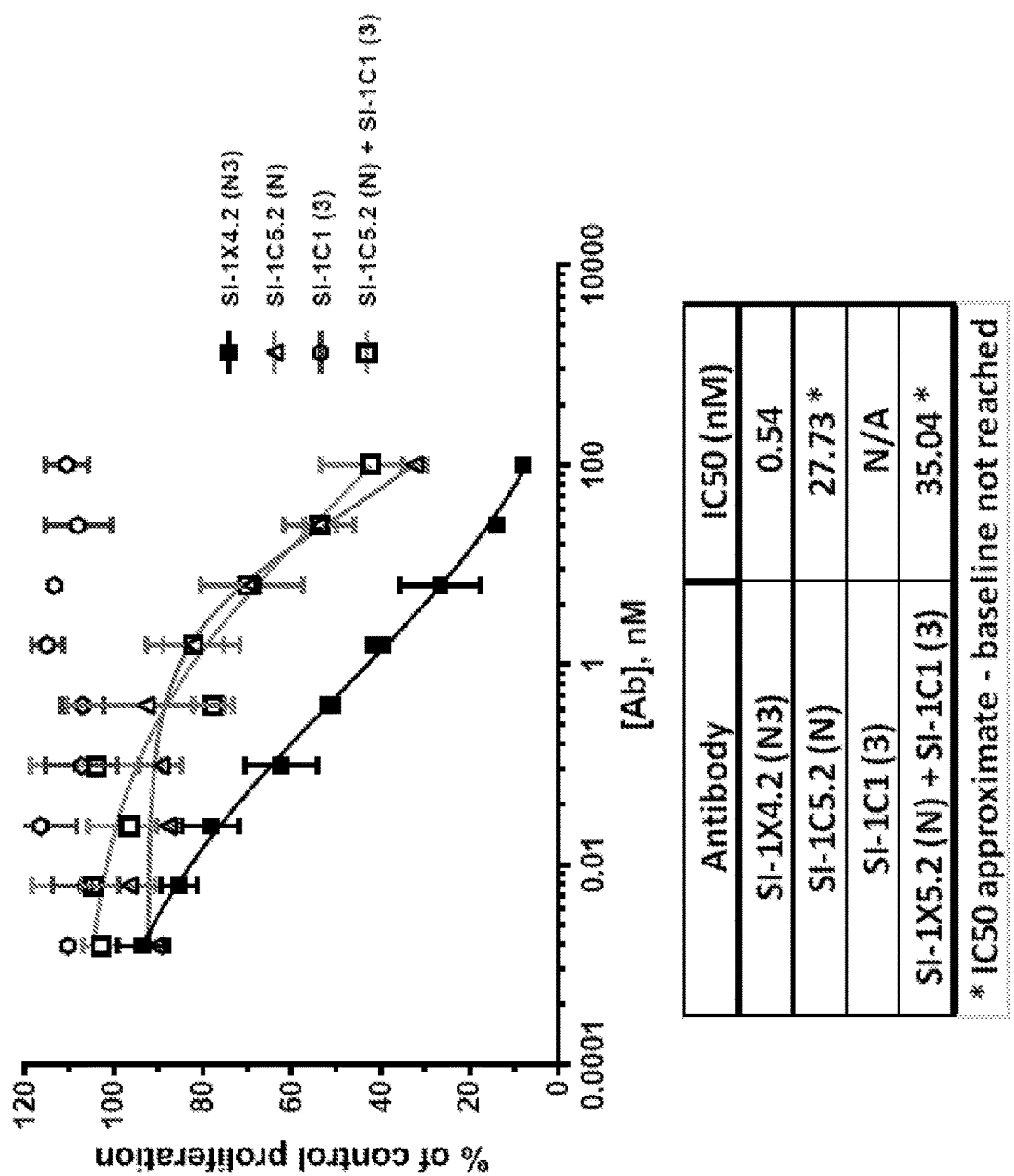
FIG. 20 shows effect of SI-1X4.2 antibodies on Fadu cell proliferation.
Figure 21:
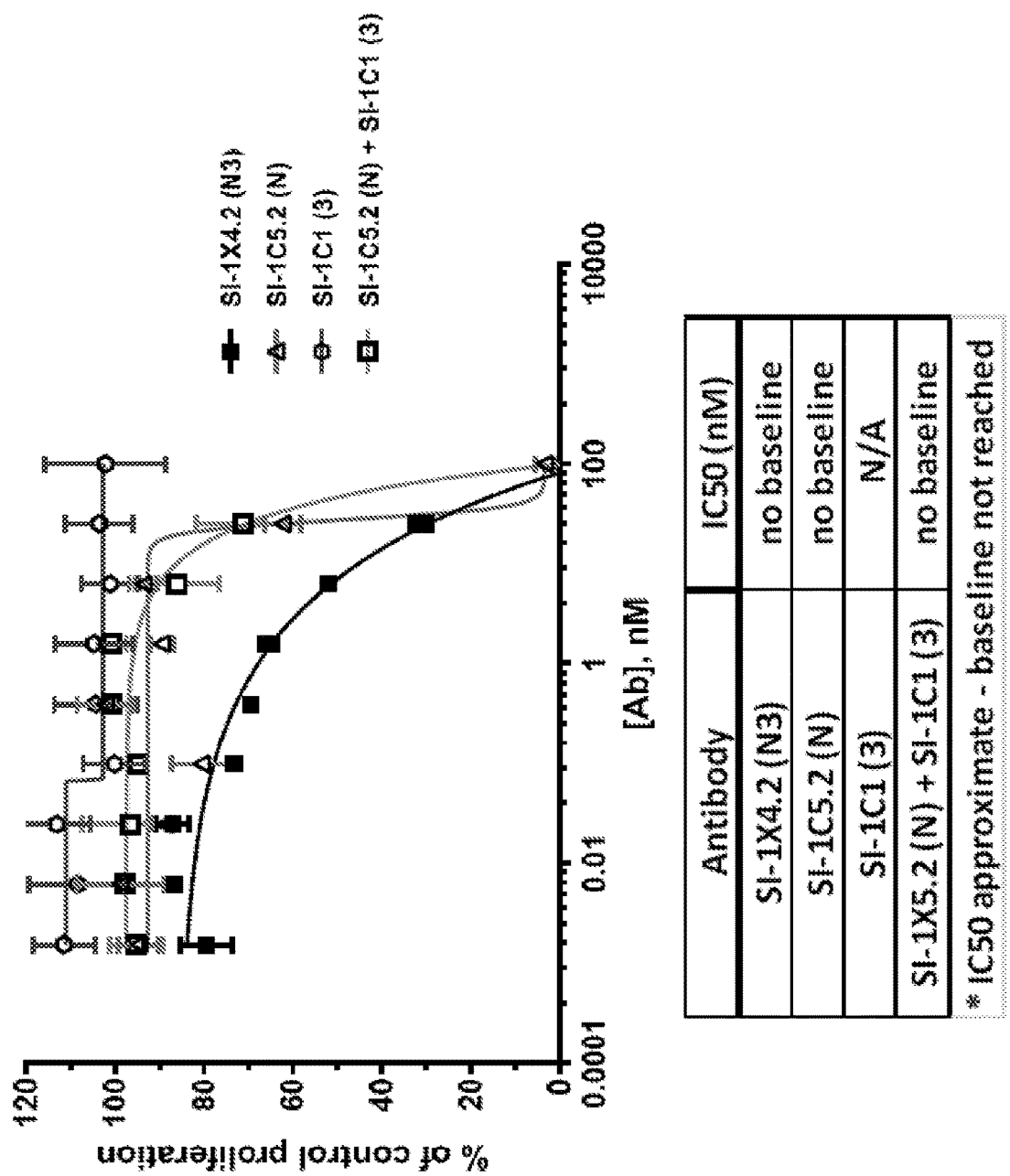
FIG. 21 shows effect of SI-1X4.2 antibodies on A431 cell proliferation.

The effects of SI-1C5.2 and SI-1X4.2 on Fadu and A431 cell proliferation are shown in FIG. 20 and FIG. 21 respectively. In both cell lines, SI-1X4.2 demonstrated improved efficacious anti-proliferative effect than the control antibodies, SI-1C5.2 (anti-EGFR Mab), SI-1C1 (anti-Her3 Mab) or SI-1C1 and SI-1C7 applied together.

Example 10

ADCC Activities of SI-1X Bispecific Antibodies

The ability of SI-1X antibodies to mediate cellular cytotoxicity against several tumor cell lines was tested. Whole blood was obtained from normal, healthy volunteers. Blood was diluted with an equal volume of phosphate buffered saline (PBS). 20 ml aliquots of diluted blood were carefully layered over 15 ml Ficol Pacque PLUS (GE Life Sciences cat #17-1440-02; Pittsburgh, Pa.). Tubes were centrifuged at 300 g for 40 minutes with no brake. Following centrifugation most of the plasma layer was carefully aspirated and the buffy coat (containing PBMC) was carefully removed with a pipet in the smallest possible volume. PBMCs were pooled in 50 ml tubes and PBS added to bring each tube up to 50 ml. Tubes were centrifuged at 1300 RPM for 10 minutes and the supernatant was carefully aspirated. Cells were resuspended in 40 ml PBS and centrifuged again. The process was repeated for a total of 2 washes. Following the final wash, cells were resuspended in 30 ml RPMI-1630+10% FBS and incubated overnight at 37° C., 5% $CO_2$.

Target cells tested were the head and neck squamous cell carcinoma line, FaDu (ATCC HTB-43, Manassus, Va.) and the non-small cell lung adenocarcinoma cell line, NCI-H1975 (ATCC CRL-5908, Manassus, Va.). Target cells were labeled with calcein as follows. Cells were grown as monolayers and were detached by incubation with accutase. Cells were washed twice in RPMI with no serum. 1 ml of cells at $4 \times 10^6$ cells/ml was mixed with 1 ml RPMI (no serum)+20 µM calcein AM (Sigma cat #C1359; St. Louis, Mo.). Cells were incubated at 37° C. for 30 minutes, with gentle mixing every 10 minutes. Following labeling, cells were washed twice with 14 ml RPMI+10% FBS+2.5 mM probenecid (assay medium). Probenecid (Sigma cat #P8761; St. Louis, Mo.) is an anionic transporter inhibitor and is known to reduce spontaneous release of intracellular calcein. Cells were resuspended in 20 ml assay medium and allowed to recover for 2 hours at 37° C., 5% $CO_2$. Cells were then washed once with assay medium and diluted to 200,000 cells/ml. Aliquots of 50 µl (10,000 cells) calcein-labeled cells were aliquoted to 96-well round-bottom plates. 50 µl of antibody (at 3x final concentration) was added to cells and allowed to bind for 40 minutes on ice. PBMCs from the previous day were centrifuged at 300 g for 5 minutes, resuspended in 20 ml fresh assay medium, counted, and diluted to $6 \times 10^6$ cells/ml. 50 µl PBMC (300,000) were added to each well and plates incubated at 37° C., 5% $CO_2$ for 4 hours. Each antibody was titrated in triplicate via 10-fold serial dilutions, starting at 50 nM and going down to 0.00005 nM. Control wells were also set up containing labeled target cells in the absence of antibody and effector cells in order to measure maximal and spontaneous calcein release.

At the end of the 4-hour incubation, 50 µl of assay medium containing 8% IGEPAL CA-630 (Sigma cat #I8896; St. Louis, Mo.) was added to control wells containing labeled target cells only (to measure the maximal calcein release). 50 µl of assay medium was added to all the other wells to bring the total volume to 200 µl per well. Plates were centrifuged at 2000 RPM for 10 minutes and 150 µl supernatant was carefully transferred to V-bottom 96-well plates. These plates were centrifuged at 2000 RPM for an additional 10 minutes and 100 ml supernatant was carefully transferred to black, clear-bottom 96-well plates. Calcein in the supernatant was quantitated by measuring the fluorescence of each sample using an excitation wavelength of 485 nM and an emission wavelength of 535 nM. The percentage of specific lysis was calculated as follows:

% specific lysis=[(test sample value−spontaneous release)/(maximal release−spontaneous release)]*100

Figure 22A:
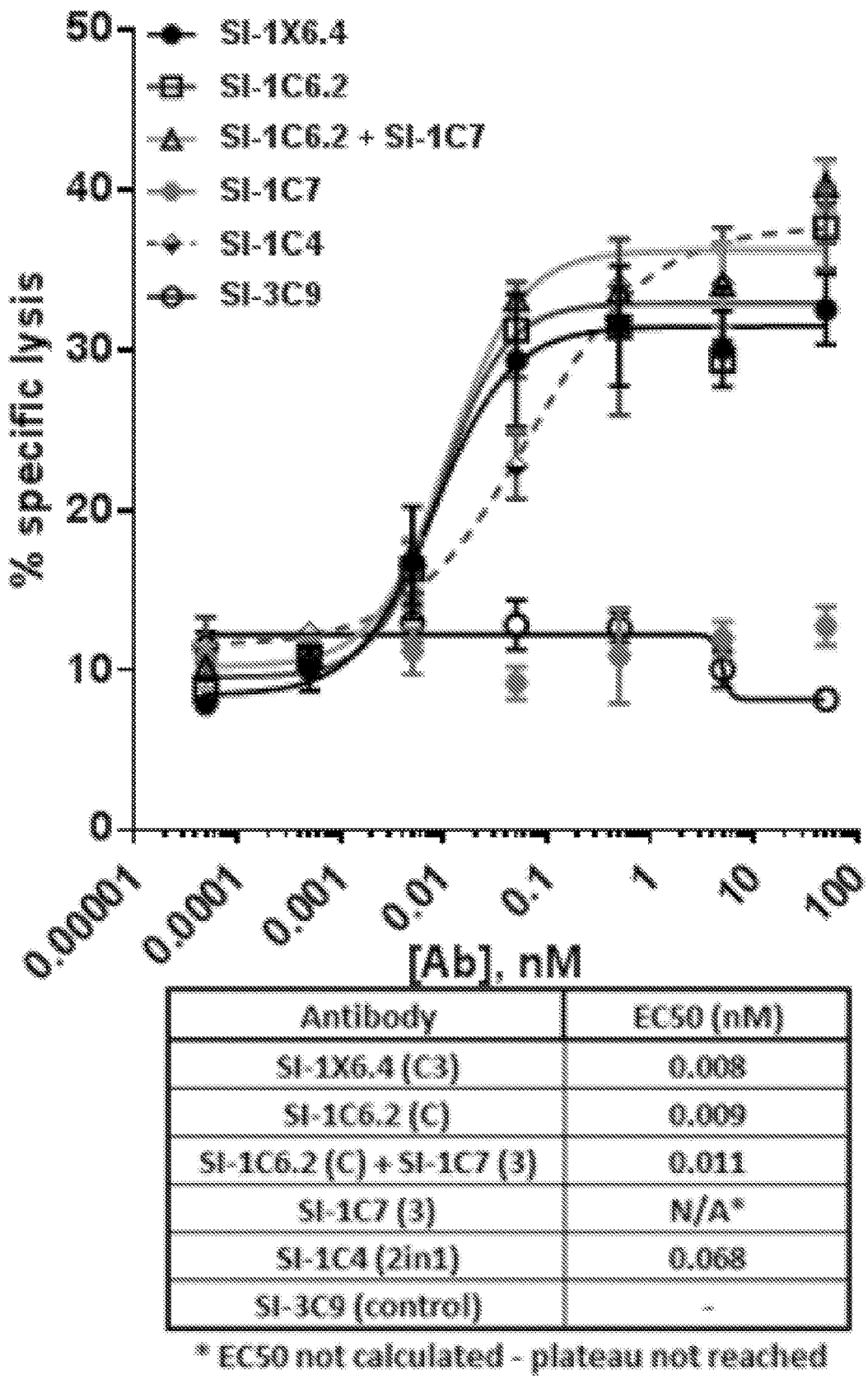
FIG. 22 shows ADCC activity of SI-1X antibodies on Fadu cell.
Figure 22B:
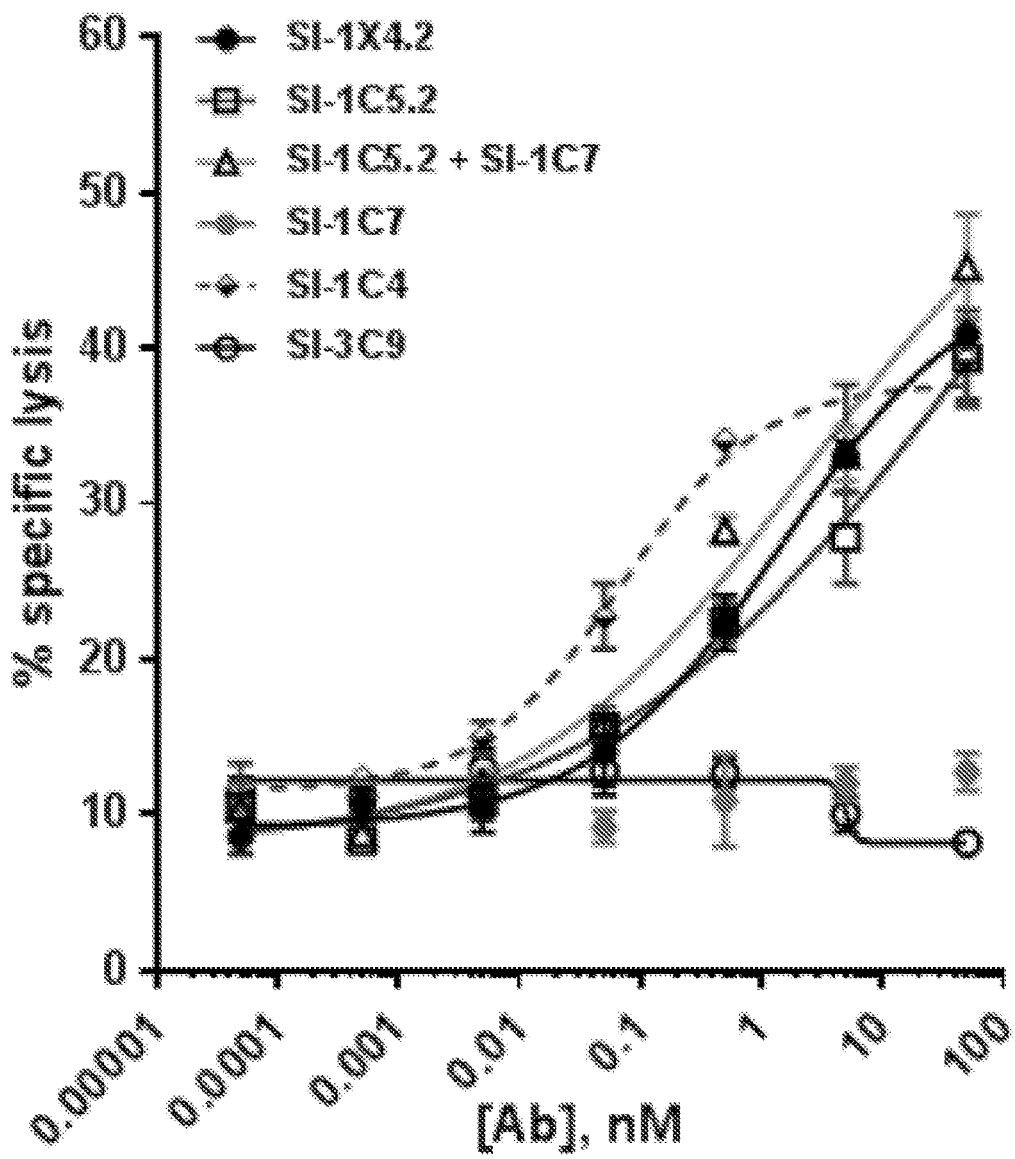
Figure 23A:
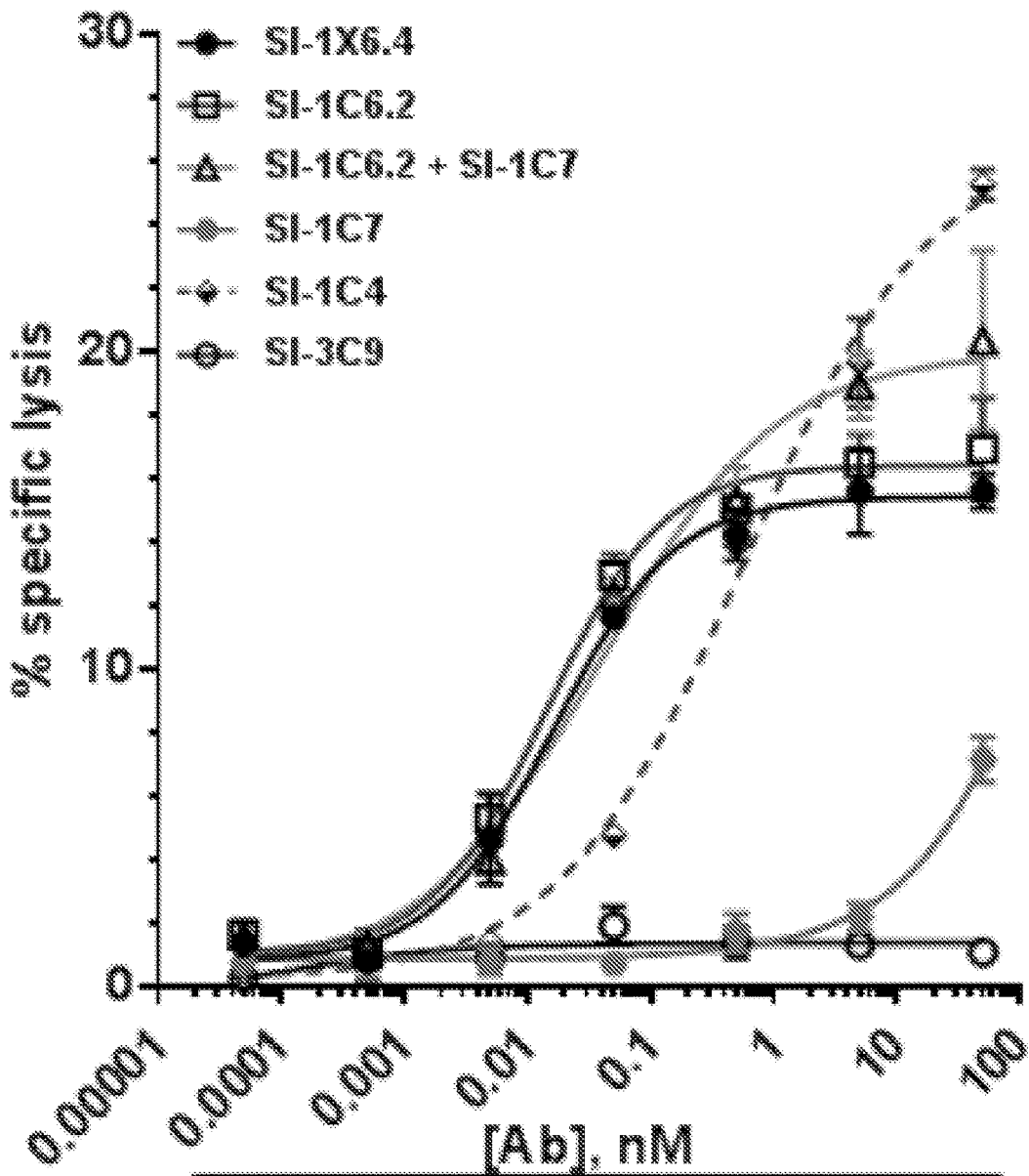
FIG. 23 shows ADCC activity of SI-1X antibodies on NCI-H1975 cells.
Figure 23B:
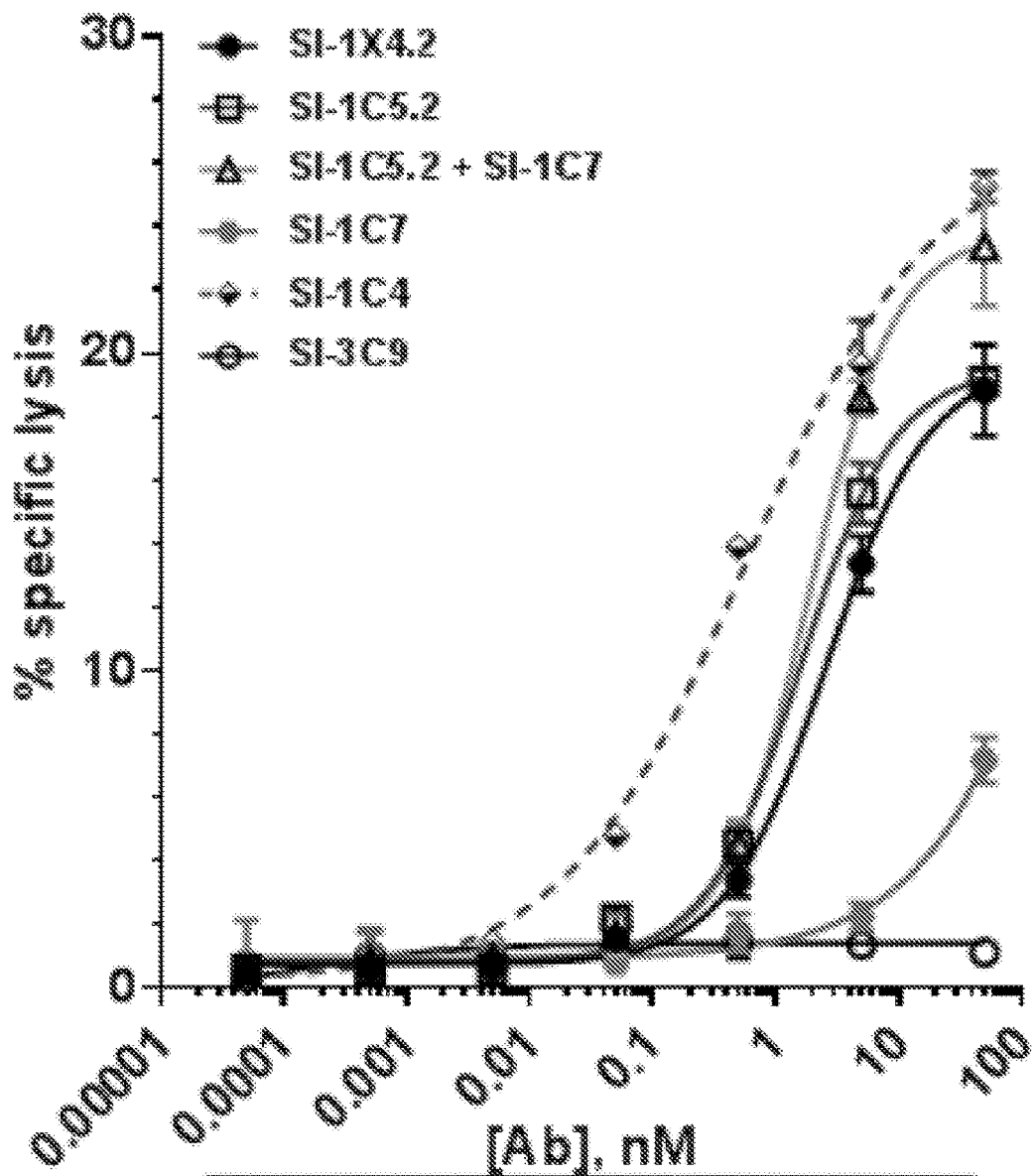

The data is shown in FIG. 22 and FIG. 23. For both cell lines, SI-1X6.4 mediated cellular cytotoxicity, but was not particularly more effective than the control antibodies, SI-1C6.2, SI-1C7, or the combination of SI-1C6.2+SI-1C7. SI-1X6.4 did mediate cytotoxicity with a lower EC50 than our benchmark antibody, SI-1C4. For both cell lines, SI-1X4.2 mediated cellular cytotoxicity at about the same degree as the control antibodies. However, it was not as effective as mediating cellular cytotoxicity as the benchmark, SI-1C4. This is likely due to the lower affinity of SI-1X4.2.

Example 11

Thermal Stability of SI-1X Bispecific Antibodies

Figure 24:
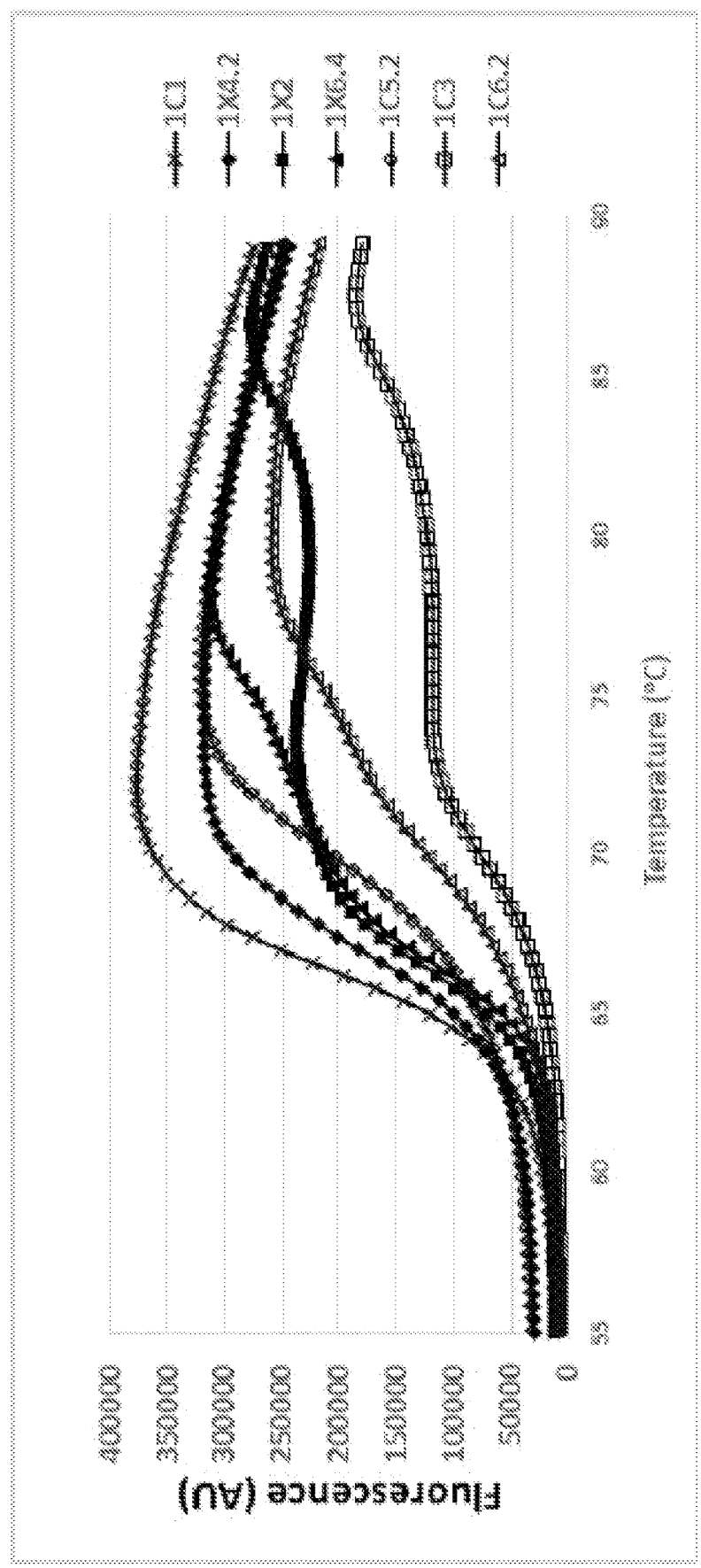
FIG. 24 shows the thermal melting of SI-1X antibodies to demonstrate their stability.
Figure 25A:
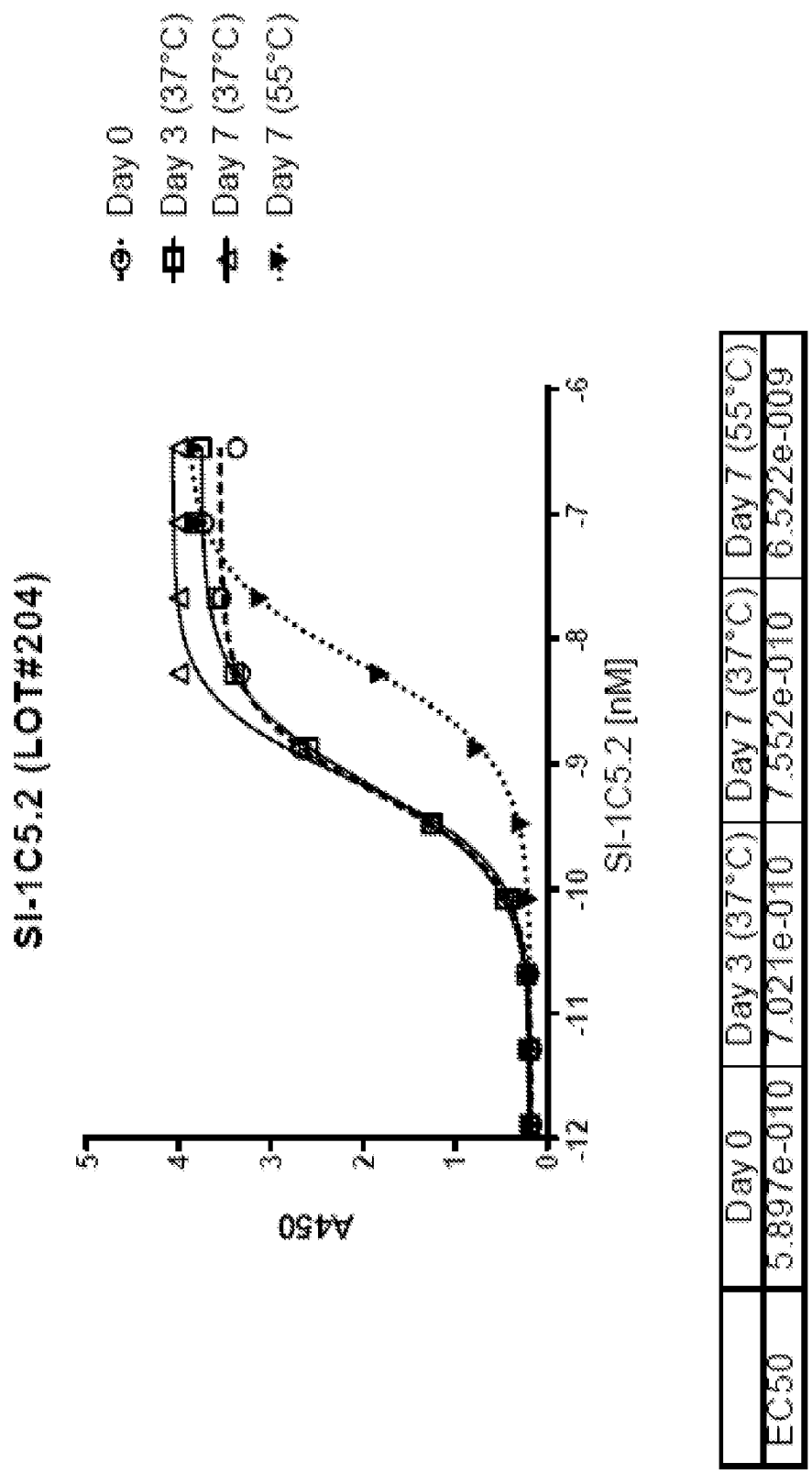
FIG. 25 shows the serum stability of SI-1X antibodies over 7 days period.
Figure 25B:
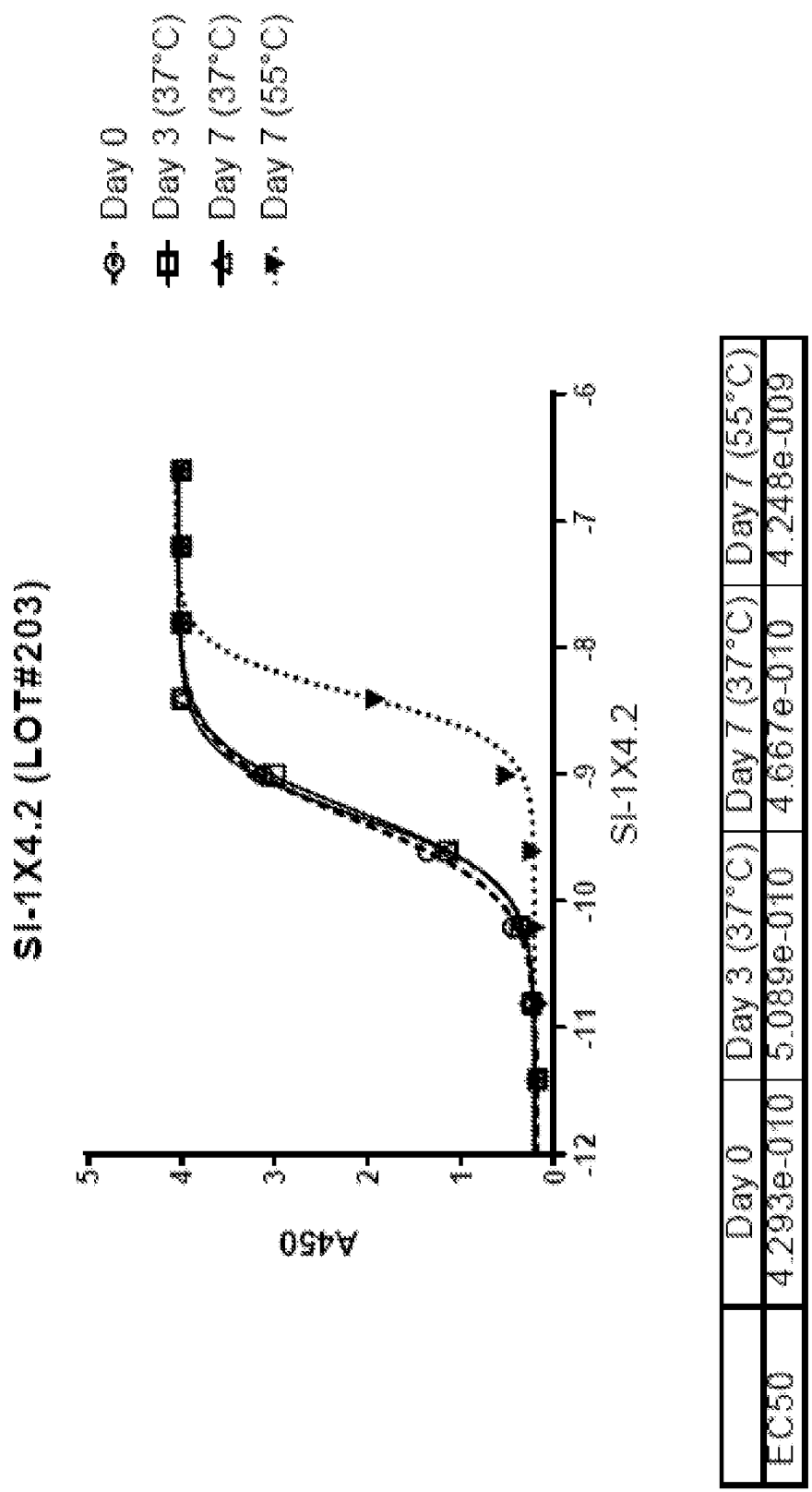
Figure 25C:
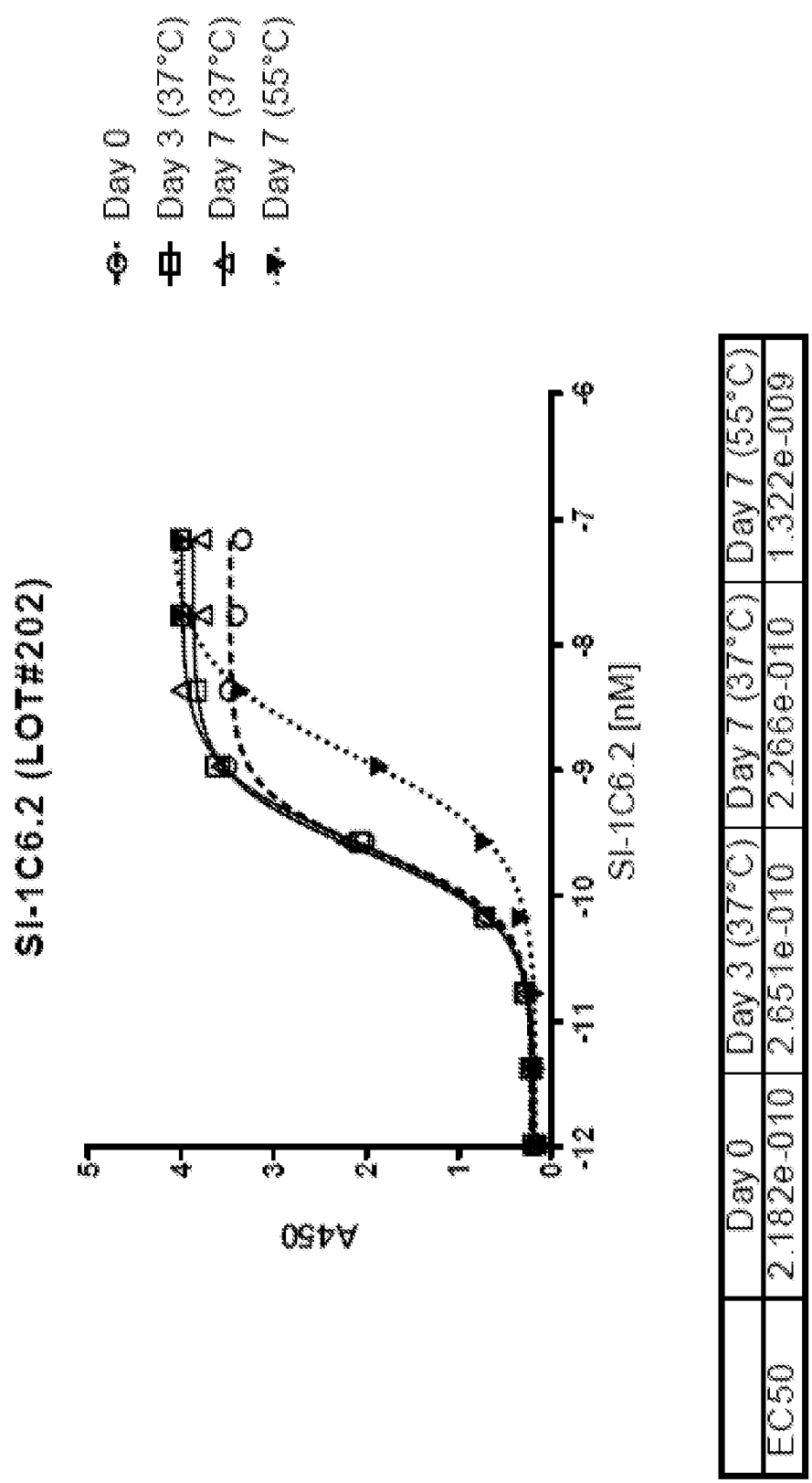
Figure 25D:
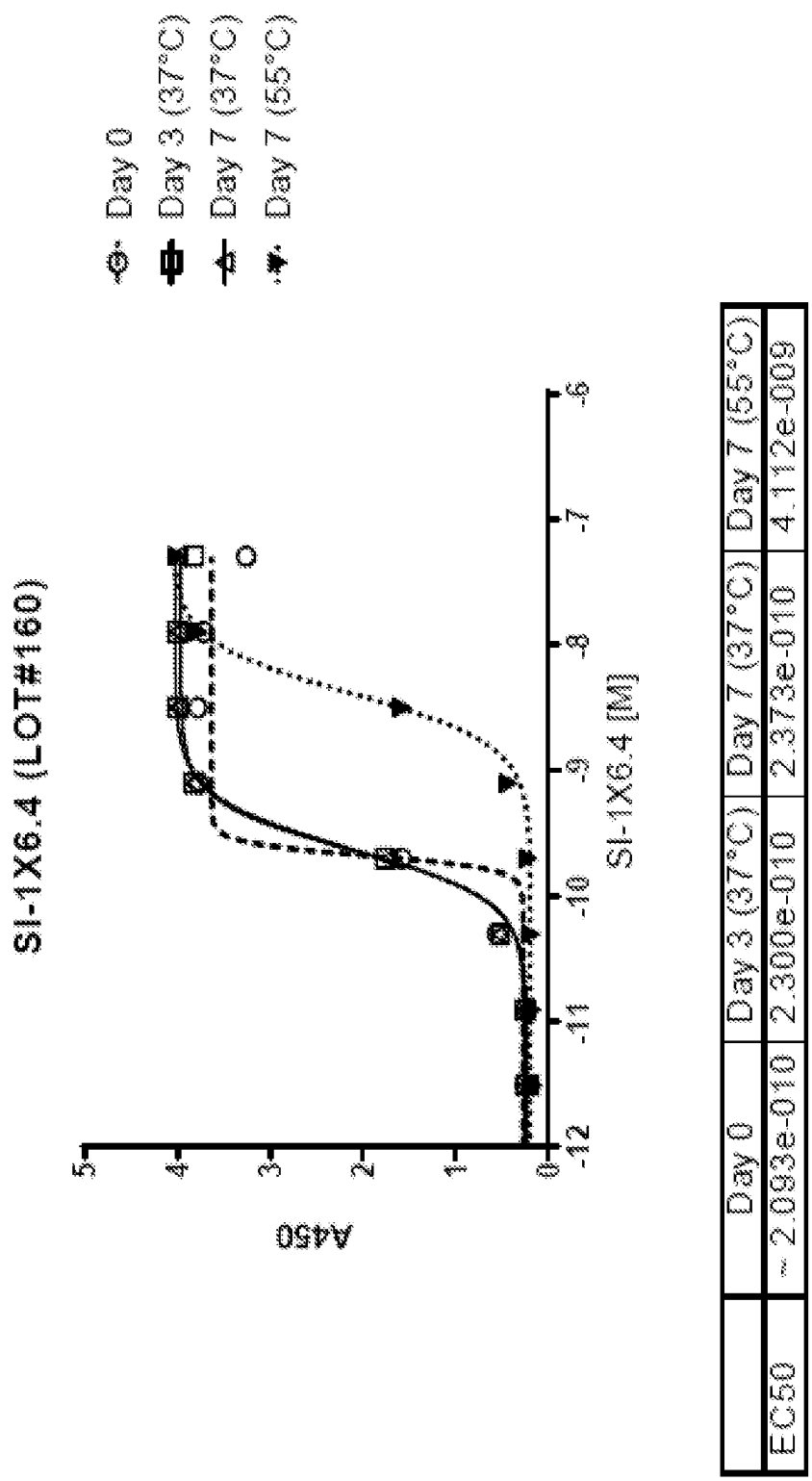

Protein Thermal Shift Study was performed for protein thermal stability analysis. Protein melt reactions were set up using Protein Thermal Shift Buffer™ and the Protein Thermal Shift Dye™ (Applied Biosystems). In brief, the 20 µl reaction mixture contains 5 µg protein, 5 µl Protein Thermal Shift Buffer™ and 2.5µ 8× diluted Protein Thermal Shift™ Dye. For the negative control, PBS was used instead. The reaction mixture was added into MicroAmp Optical Reaction Plate and sealed with MicroAmp Optical Adhesive Film. Each sample consisted of 4 repeats. The protein melt reactions were run on Applied Biosystem Real-Time PCR System from 25-90° C. in 1% increment and then analyzed by Protein Thermal Shift Software™. FIG. 24 shows the thermal curve of SI-1X2, SI-1X4.2, SI-1X6.4, SI-1C3, SI-1C3, SI-1C6.2, SI-1C5.2 and SI-1C7. TABLE 5 shows Tm for these molecules. Tm is defined as the temperature needed to unfold 50% of the protein. The bispecific molecules, 1X2, 1X4.2 and 1X6 all have Tm around 66° C. which are comparable to all the MAbs (1C3, 1C6.2, 1C5.2) and the Fc-scFv (1C7) molecules.

TABLE 5

| Protein Name | Tm (° C.) |
| --- | --- |
| SI-1X2 | 66.52 |
| SI-1C3 | 70.06 |
| SI-1X4.2 | 66.94 |
| SI-1C5.2 | 70.26 |
| SI-1X6.4 | 66.50 |
| SI-1C6.2 | 70.12 |
| SI-1C7 | 66.40 |

Example 12

Serum Stability of SI-1X Bispecific Antibodies

Serum stability of the molecules SI-1C5.2, SI-1C6.2, SI-1X4.2, and SI-1X6.4 was determined by comparative binding to monomeric EGFR ECD by ELISA after incubation at 100 µg/mL in 95% human serum (Atlanta Biologics, S40110) at 37° C. for Days 0, 3, and 7 time points with an extra time point of 55° C. on Day 7 to provide a known condition where degradation occurs. ELISA plates were coated with monomeric EGFR ECD (SI-2R4) at 3 µg/mL in PBS at 4° C. overnight. Coated ELISA plates were blocked with 3% BSA PBST for 2 hours at 25° C. and then washed 3 times with PBST. SI-1C6.2 and SI-1X6.4 were diluted 1:10 with 1% BSA PBST and diluted 4× across the plate. SI-1C5.2 and SI-1X4.2 were diluted 1:2 with 1% BSA PBST and diluted 4× across the plate and incubated at 25° C. for 1 hour. 3 more washes with PBST were performed before antigen capture with 1 µg/mL Her3 ECD Rabbit IgG1 (SI-1R1) for 1 hour at 25° C. in 1% BSA PBST. 3 more washes with PBST were performed before goat anti-rabbit IgG-HRP (Bio-Rad 172-1019) secondary antibody was applied at 1:5000 dilution in 1% BSA PBST at 25° C. for 1 hour. 3 final washes with PBST before development with 100 µl Pierce 1-step Ultra TMB ELISA (Pierce, 34028) for 10 minutes with a final quench of 100 µl 2 M $H_2SO_4$. Plates were read at 450 nm. ELISA data was plotted and curves created using GraphPad Prism 6.

Results of the ELISA are reported by EC50 on FIG. 25 and indicate a favorable profile of minor degradation when held at 37° C. When placed in 55° C., the EC50 shifts roughly a log as the molecules are subjected to degradation conditions. EC50 values for SI-1C5.2 shift from 589.7 pM on Day 0 to 755.2 pM on Day 7 at 37° C. (Δ165.5 pM) with a shift to 6.522 nM on Day 7 at 55° C. (Δ5932.3 pM). EC50 values for SI-1C6 shift from 218.2 pM on Day 0 to 226.6 pM on Day 7 at 37° C. (Δ8.4 pM) with a shift to 1.322 nM on Day 7 at 55° C. (Δ1103 pM). EC50 values for SI-1X4.2 shift from 429.3 pM on Day 0 to 466.7 pM on Day 7 at 37° C. (Δ37.4 pM) with a shift to 4.248 nM on Day 7 at 55° C. (Δ3818.7 pM). EC50 values for SI-1X6 shift from 209.3 pM on Day 0 to 237.3 pM on Day 7 at 37° C. (Δ28 pM) with a shift to 4.112 nM on Day 7 at 55° C. (Δ3902.7 pM).

Example 13

PK Half-Life of SI-1X Molecules

To test their half-life in vivo, pharmacokinetic experiments were performed in SD rats. A single, intravenous tail vein injection of bispecific Abs (1C6 10 mg/kg, 1X6 10 mg/kg, 1X2 10 mg/kg, 1X4 32 mg/kg) were given to groups of 4 female rats randomized by body weight (190-212 g range). Blood (~150 µL) was drawn from the orbital plexus at each time point, processed for serum, and stored at −80° C. until analysis. Study durations were 28 days.

Antibody concentrations were determined using three ELISA assays. In assay 1 (EGFR ECD coated ELISA), recombinant EGFR-rabbit Fc was coated to the plate, wells were washed with PBST (phosphate buffered saline with 0.05% Tween) and blocked with 1% BSA in PBST. Serum or serum diluted standards were then added, followed by PBST washing, addition of HRP labeled rabbit-anti-human IgG (BOSTER), and additional PBST washing. TMB was then added and the plates were incubated 2.5 minutes in the dark. Color reaction was stopped by adding 2 M sulfuric acid. Plate was read at 450 nm wavelength. For assay 2 (Her3 coated ELISA), serum was detected using a similar ELISA, but recombinant HER3-His was used as capture reagent. For assay 3 (Sandwich ELISA), recombinant HER3-His was coated, serum or serum diluted standard were added, followed by PBST washing, addition of EGFR-rabbit Fc in PBST, and additional PBST washing. HRP labeled goat-anti-rabbit IgG (BOSTER) was then added. PK parameters were determined with a non-compartmental model.

Figure 26:
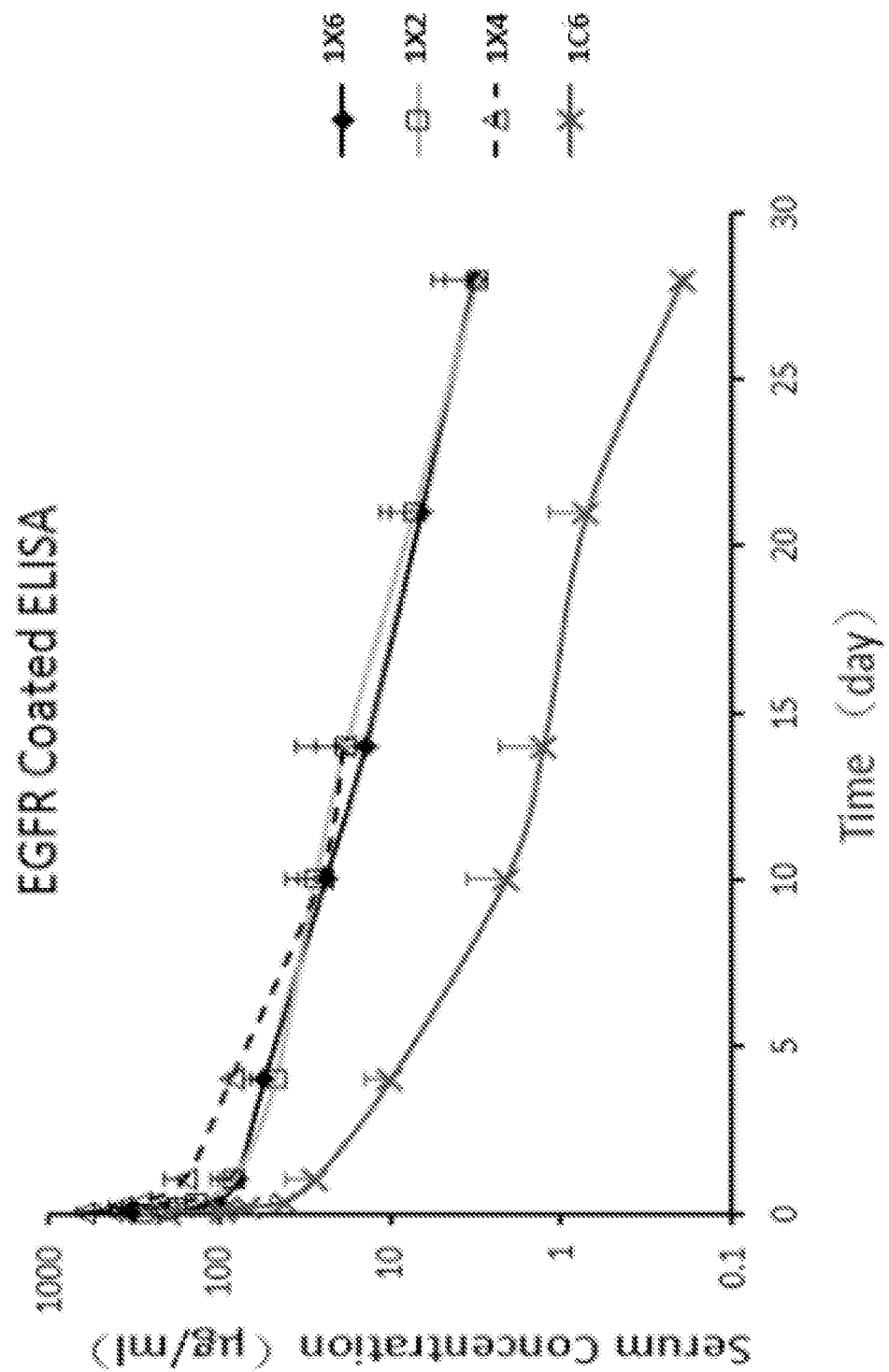
FIG. 26 is a graph showing the results of EGFR coated ELISA for the PK study in rat.
Figure 27:
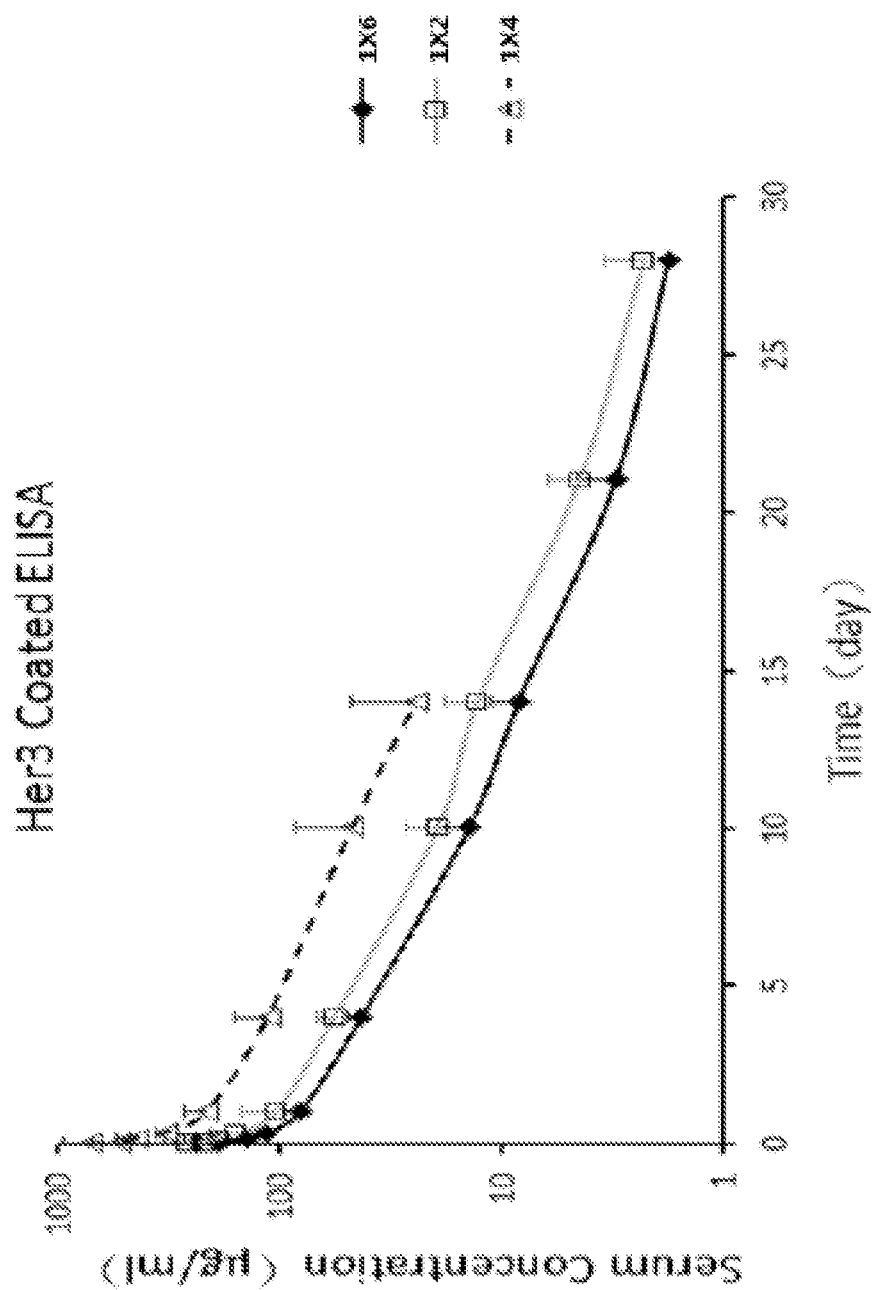
FIG. 27 is a graph showing the results of HER3 coated ELISA for the PK study in rat.
Figure 28:
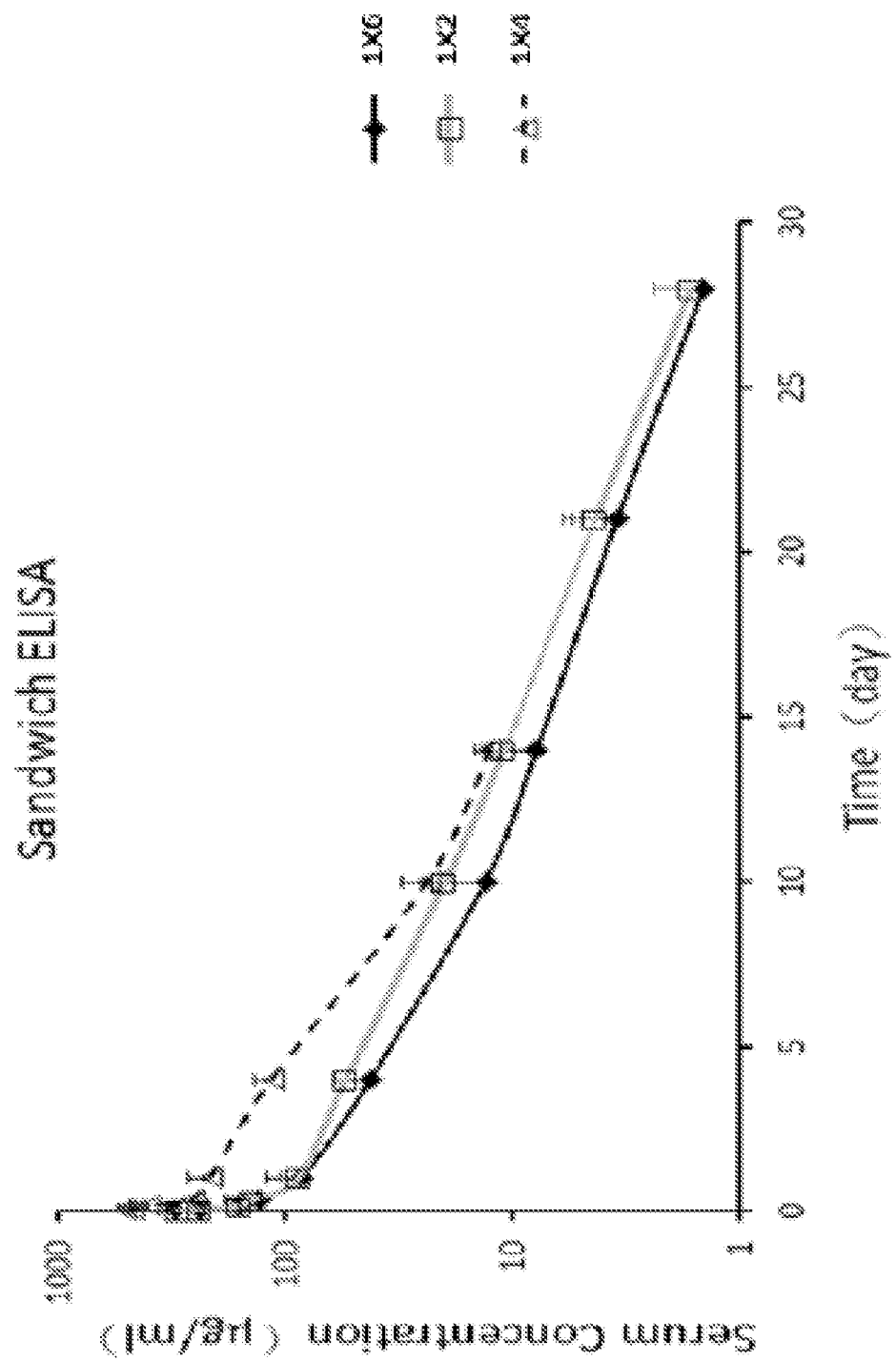
FIG. 28 is a graph showing the results of sandwich ELISA for the PK study in rat.

FIGS. 26-28 show serum concentration data for four antibodies with three different assays respectively. Fitted PK parameters from in vivo PK studies are provided in TABLE 6. PK data include half-life, which represents the beta phase that characterizes elimination of antibody from serum and Cmax, which represents the maximal observed serum concentration, AUC, which represents the area under the concentration time curve.

TABLE 6

| Assay | Sample | Half-Life (h) | Cmax (μg/ml) | AUC (μg/ml*h) |
|---|---|---|---|---|
| EGFR Coated ELISA | SI-1X6 | 159 | 325.5 | 18250.6 |
| | SI-1X2 | 130 | 280.3 | 18889.8 |
| | SI-1X4.2 | 146 | 627.8 | 31317.0 |
| | SI-1C6 | 130 | 196.4 | 3790.3 |
| Her3 Coated ELISA | SI-1X6 | 142 | 236.7 | 14213.6 |
| | SI-1X2 | 136 | 264.8 | 19012.2 |
| | SI-1X4.2 | 124 | 715.6 | 40063.4 |
| Sandwich ELISA | SI-1X6 | 136 | 301.6 | 14182.6 |
| | SI-1X2 | 123 | 297.6 | 17203.9 |
| | SI-1X4.2 | 211 | 518.9 | 34874.6 |

Example 14

Mouse Xenograft Studies

The example tested the activity of SI-1X2, SI-1X4.2 and SI-1X6 of concomitant blockade of EGFR, HER3 in preclinical models of Fadu (head and neck squamous cell carcinoma xenograft model) and compared their potency with cetuximab and cetuximab in combination with an anti-HER3 antibody.

All mouse studies were conducted through Institutional Animal care and used committee-approved animal protocols in accordance with institutional guidelines. Six-week-old female Balb/c Nude mice were purchased from Beijing Vital River Laboratories and housed in air-filtered laminar flow cabinets with a 12-hour light cycle and food and water ad libitum. The size of the animal groups was calculated to measure means difference between placebo and treatment groups of 25% with a power of 80% and a P value of 0.01. Host mice carrying xenografts were randomly and equally assigned to either control or treatment groups. Animal experiments were conducted in a controlled and non-blinded manner. For cell line-derived xenograft studies, mice were injected subcutaneously with 2×106 Fadu suspended 150 μl of culture medium per mouse.

Once tumors reached an average volume of 100-250 mm3, mice were randomized into 9 groups, with 6 mice per group. Vehicle Control, 1C6 (25 mg/kg), 1C4 (25 mg/kg), 1C6+1C1 (25 mg/kg+50 mg/kg), SI-1X2 (25 mg/kg), SI-1X6 (10 mg/kg), SI-1X6 (25 mg/kg), and SI-1X4.2 (10 mg/kg), SI-1X4 (25 mg/kg). All test articles were administered once weekly via intravenous injection. Tumors were measured by digital caliper over the entire treatment period every 3 days and the volume was determined using the following formula: ½×lenth×width2. The body weight of mice were recorded before the first dose and followed by every week during the treatment period and recovery period.

Figure 29:
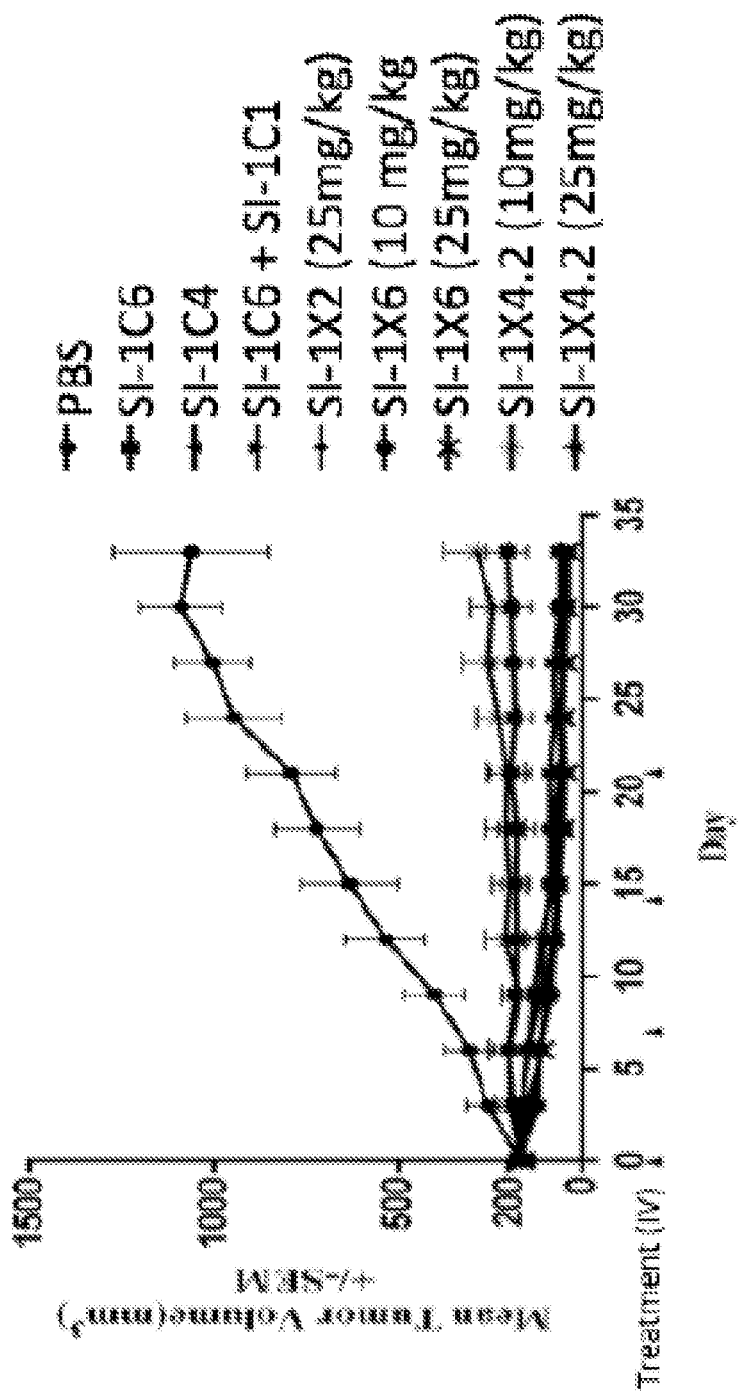
FIG. 29 is a graph showing a plot of mean tumor volume vs days in the mouse xenograft study
Figure 30:
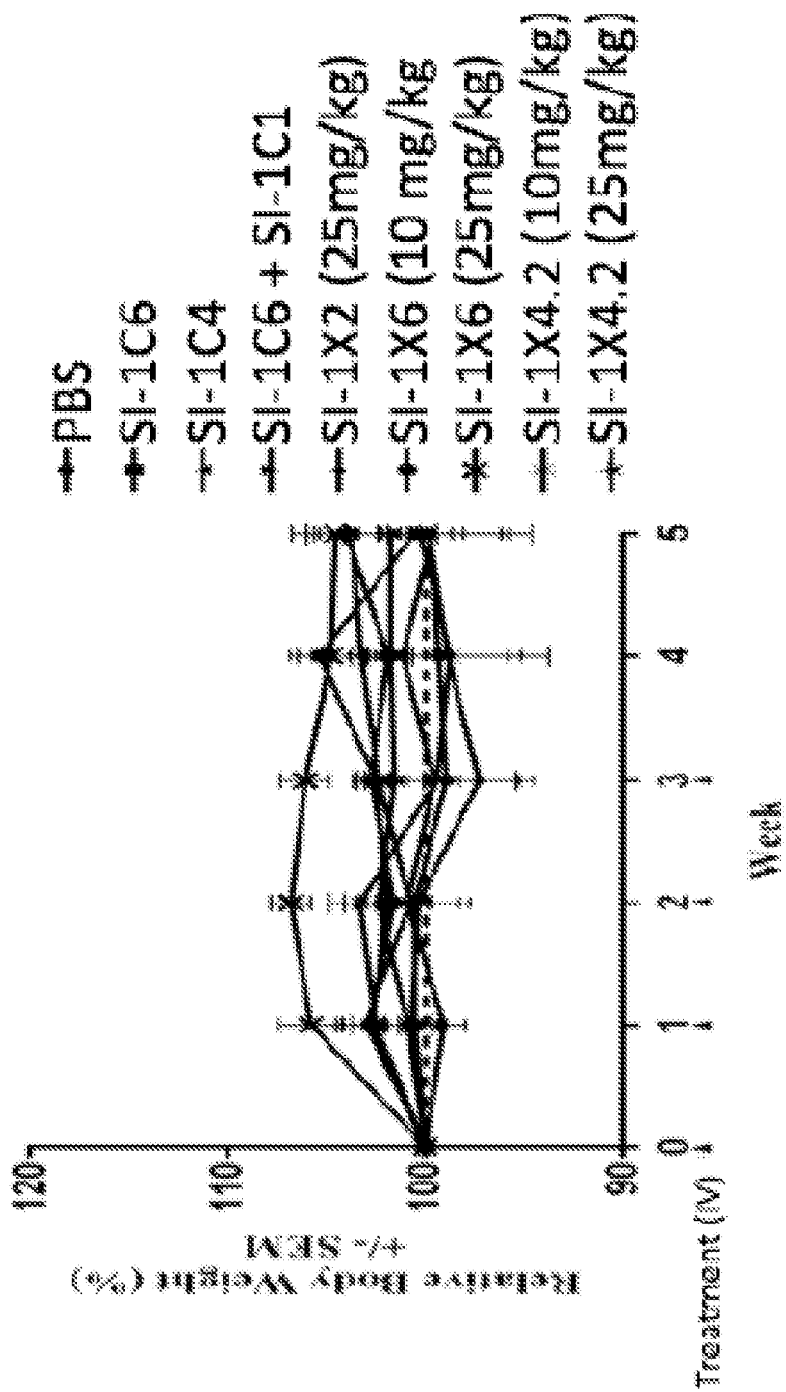
FIG. 30 is a graph showing a plot relative body weight vs weeks in the mouse xenograft study.

All the test groups of SI-1X2, SI-1X6 and SI-1X4.2 and SI-1X6 combination yielded significantly tumor growth inhibition compared to positive control of SI-1C6 excluding the low dose SI-1X4.2 10 mg/kg group (FIGS. 29-30). Moreover, no relapses were observed 2 weeks after treatment cessation excluding the low dose SI-1X4.2 10 mg/kg group.

Pharmaceutical Compositions

The term "effective amount" refers to an amount of a drug effective to achieve a desired effect, e.g., to ameliorate disease in a subject. Where the disease is a caner, the effective amount of the drug may inhibit (for example, slow to some extent, inhibit or stop) one or more of the following example characteristics including, without limitation, cancer cell growth, cancer cell proliferation, cancer cell motility, cancer cell infiltration into peripheral organs, tumor metastasis, and tumor growth. Wherein the disease is a cancer, the effective amount of the drug may alternatively do one or more of the following when administered to a subject: slow or stop tumor growth, reduce tumor size (for example, volume or mass), relieve to some extent one or more of the symptoms associated with the cancer, extend progression free survival, result in an objective response (including, for example, a partial response or a complete response), and increase overall survival time. To the extent the drug may prevent growth and/or kill existing cancer cells, it is cytostatic and/or cytotoxic.

With respect to the formulation of suitable compositions for administration to a subject such as a human patient in need of treatment, the antibodies disclosed herein may be mixed or combined with pharmaceutically acceptable carriers known in the art dependent upon the chosen route of administration. There are no particular limitations to the modes of application of the antibodies disclosed herein, and the choice of suitable administration routes and suitable compositions are known in the art without undue experimentation.

Although many forms of administration are possible, an example administration form would be a solution for injection, in particular for intravenous or intra-arterial injection. Usually, a suitable pharmaceutical composition for injection may include pharmaceutically suitable carriers or excipients such as, without limitation, a buffer, a surfactant, or a stabilizer agent. Example buffers may include, without limitation, acetate, phosphate or citrate buffer. Example surfactants may include, without limitation, polysorbate. Example stabilizer may include, without limitation, human albumin.

Similarly, persons skilled in the art have the ability to determine the effective amount or concentration of the antibodies disclosed therein to effective treat a condition such as a cancer. Other parameters such as the proportions of the various components in the pharmaceutical composition, administration does and frequency may be obtained by person skilled in the art without undue experimentation. For example, a suitable solution for injection may contain, without limitation, from about 1 to about 20, from about 1 to about 10 mg antibodies per ml. The example dose may be, without limitation, from about 0.1 to about 20, from about 1 to about 5 mg/Kg body weight. The example administration frequency could be, without limitation, once per day or three times per week.

While the present disclosure has been described with reference to particular embodiments or examples, it may be understood that the embodiments are illustrative and that the disclosure scope is not so limited.

Alternative embodiments of the present disclosure may become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description.

What is claimed is:

1. A bispecific tetravalent antibody, said bispecific tetravalent antibody comprising:
two IgG1 heavy chains;
two kappa light chains; and
two single chain Fv (scFv) domains;
wherein the two IgG1 heavy chains and kappa light chains form an IgG moiety with a binding specificity to a first member of the EGFR family;
wherein the two scFv domains have a binding specificity to a second member of the EGFR family, and each scFv domain is connected to the C-terminus of either of the IgG1 heavy chains by a connector with an amino acid sequence of (gly-gly-gly-gly-ser)$_n$, to provide a IgG1-connector connection, wherein n is an integral of at least 1;
wherein each scFv domain has a structure order of N terminus—variable heavy chain—linker—variable light chain—C terminus or N-terminus—variable light chain—linker—variable heavy chain—C-terminus, and wherein the linker is comprised of amino acid sequence of (gly-gly-gly-gly-ser)$_m$, wherein m is an integral of at least 3;
wherein at least one of the IgG1 heavy chain, connector, and scFv domain has an amino acid sequence comprising SEQ ID NO 136; and
wherein the kappa light chains comprising an amino acid sequence selected from SEQ ID NO 131 and 132.

2. The bispecific tetravalent antibody of claim 1, wherein the antibody inhibits cancer cell growth.

3. The bispecific tetravalent antibody of claim 1, wherein the antibody binds to EGFR and HER3 with a Kd less than 50 nM.

4. The bispecific tetravalent antibody of claim 1, wherein the antibody simultaneously binds to EGFR with a Kd less than 50 nM and binds to HER3 with a Kd less than 50 nM.

5. An isolated nucleic acid encoding the antibody of claim 1.

6. An expression vector comprising the isolated nucleic acid of claim 5.

7. The expression vector of claim 6, wherein the vector is expressible in a cell.

8. A host cell comprising the nucleic acid of claim 5.

9. A host cell comprising the expression vector of claim 8.

10. The host cell of claim 9, wherein the host cell is a prokaryotic cell or a eukaryotic cell.

11. An immunoconjugate comprising the antibody of claim 1 and a cytotoxic agent.

12. A pharmaceutical composition, comprising the bispecific tetravalent antibody of claim 1 and a pharmaceutically acceptable carrier.

13. The pharmaceutical composition of claim 12, further comprising radioisotope, radionuclide, a toxin, a therapeutic agent, a chemotherapeutic agent or a combination thereof.

14. A pharmaceutical composition, comprising the immunoconjugate of claim 11 and a pharmaceutically acceptable carrier.

15. A method of treating a subject with a cancer that comprises cells that express EGFR and/or HER3, comprising administering to the subject an effective amount of the bispecific tetravalent antibody of claim 1.

16. The method of claim 15, wherein the cancer comprises breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer.

17. The method of claim 15, further comprising co-administering an effective amount of a therapeutic agent.

18. The method of claim 17, wherein the therapeutic agent comprises an antibody, a chemotherapy agent, an enzyme, or a combination thereof.

19. The method of claim 17, wherein the therapeutic agent comprises an anti-estrogen agent, a receptor tyrosine inhibitor, or a combination thereof.

20. The method of claim 17, wherein the therapeutic agent comprises capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, a derivative or a combination thereof.

21. The method of claim 17, wherein the therapeutic agent comprises a check point inhibitor.

22. The method of claim 17, wherein the therapeutic agent comprises PD1, PDL1, CTLA4, 4-1BB, OX40, GITR, TIM3, LAG3, TIGIT, CD40, CD27, HVEM, BTLA, VISTA, B7H4, a derivative or a combination thereof.

23. The method of claim 15, wherein the subject is a human.

24. A method of inhibiting the biological activity of a HER receptor in a subject, comprising administering to the subject an effective amount of the antibody of claim 1 to inhibit a biological activity of said HER receptor, wherein said HER receptor is EGFR and/or HER3.

25. The bispecific tetravalent antibody of claim 1, wherein one of the IgG1 heavy chains is a humanized IgG1 heavy chain.

26. The bispecific tetravalent antibody of claim 1, wherein both IgG1 heavy chains are human IgG1 heavy chains.

27. The bispecific tetravalent antibody of claim 1, wherein one of kappa lights chains is a humanized kappa light chain.

28. The bispecific tetravalent antibody of claim 1, wherein both kappa light chains are human kappa light chains.

29. The bispecific tetravalent antibody of claim 1, wherein the IgG1-connector connection is resistant to protease activity.

* * * * *